US007989457B2

(12) United States Patent
Chappell et al.

(10) Patent No.: US 7,989,457 B2
(45) Date of Patent: Aug. 2, 2011

(54) GLUCAGON RECEPTOR ANTAGONISTS, PREPARATION AND THERAPEUTIC USES

(75) Inventors: Mark Donald Chappell, Noblesville, IN (US); Scott Eugene Conner, Indianapolis, IN (US); Isabel Cristina Gonzalez Valcarcel, Indianapolis, IN (US); Jason Eric Lamar, Indianapolis, IN (US); Jianke Li, Indianapolis, IN (US); Julie Sue Moyers, Indianapolis, IN (US); Rebecca Anne Owens, Beech Grove, IN (US); Allie Edward Tripp, Indianapolis, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1261 days.

(21) Appl. No.: 11/569,273

(22) PCT Filed: May 13, 2005

(86) PCT No.: PCT/US2005/016637
§ 371 (c)(1),
(2), (4) Date: Nov. 17, 2006

(87) PCT Pub. No.: WO2005/118542
PCT Pub. Date: Dec. 15, 2005

(65) Prior Publication Data
US 2008/0125468 A1    May 29, 2008

Related U.S. Application Data

(60) Provisional application No. 60/575,469, filed on May 28, 2004.

(51) Int. Cl.
*C07D 239/26* (2006.01)
*A61K 31/505* (2006.01)
(52) U.S. Cl. ........................................ 514/256; 544/335
(58) Field of Classification Search .................. 544/335; 514/256
See application file for complete search history.

(56) References Cited

U.S. PATENT DOCUMENTS
5,811,459 A    9/1998    Breault et al.

FOREIGN PATENT DOCUMENTS
WO    WO 03/048109    6/2003
WO    WO 2004/002480    1/2004

OTHER PUBLICATIONS

Kurukulasuriya, Ravi et al. "Biaryl amide glucagon receptor antagonists" *Bioorganic & Medicinal Chemistry Letters*, 14(9), p. 2049; table 1; 2004.
Beasley, Helen L. et al. "Development of a Panel of Immunoassays for Monitory DDT, Its Metablolites, and Analogs in Food and Environmental Matrixes" *Journal of Agricultural and Food Chemistry*, 46(8), pp. 3339-3352; compound Hapten VI, 1998.
Kundu, B. et al. "Identification of novel.alpha.-glucosidase inhibitors by screening libraries based on N-'r-(Benzyloxy) benzoyl! alanine derivatives" *Chemical Abstratcts Service*, 5(7), pp. 545-550, 2002.

*Primary Examiner* — Deepak Rao
(74) *Attorney, Agent, or Firm* — Dan L. Wood

(57) ABSTRACT

The present invention discloses novel compounds of Formula (I), or pharmaceutically acceptable salts thereof, which have glucagon receptor antagonist or inverse agonist activity, as well as methods for preparing such compounds. In another embodiment, the invention discloses pharmaceutical compositions comprising compounds of Formula (I) as well as methods of using them to treat diabetic and other glucagon related metabolic disorders, and the like.

6 Claims, No Drawings

GLUCAGON RECEPTOR ANTAGONISTS, PREPARATION AND THERAPEUTIC USES

This patent application is a 371 of PCT/US05/16637 filed May 13, 2005 which claims the benefit of U.S. Provisional Patent Application No. 60/575,469 filed May 28, 2004.

This invention relates to compounds that are antagonists or inverse agonists of the glucagon receptor, and to pharmaceutical compositions thereof, and the uses of these compounds and compositions in the treatment of the human or animal body. The present compounds show a high affinity and selective binding for the glucagon receptor, and as such are useful in the treatment of disorders responsive to the modulation of glucagon receptors, such as diabetic and other glucagon related metabolic disorders, and the like.

Glucagon is a key hormonal agent that, in cooperation with insulin, mediates homeostatic regulation of the amount of glucose in the blood. Glucagon primarily acts by stimulating certain cells (important among these are liver cells) to release glucose when blood glucose levels fall. The action of glucagon is opposite to that of insulin, which stimulates cells to take up and store glucose whenever blood glucose levels rise. Both glucagon and insulin are peptide hormones. Glucagon is produced in the alpha islet cells of the pancreas and insulin is produced in the beta islet cells. Glucagon exerts its action by binding to and activating its receptor, which is a member of the Glucagon-Secretin branch of the 7-transmembrane G-protein coupled receptor family. The receptor functions by activating the adenylyl cyclase second messenger system resulting in an increase in cAMP levels. The glucagon receptor, or naturally occurring variants of the receptor, may possess intrinsic constitutive activity, in vitro, as well as in vivo (i.e. activity in the absence of an agonist). Compounds acting as inverse agonists can inhibit this activity. Diabetes mellitus is a common disorder of glucose metabolism. The disease is characterized by hyperglycemia and may be classified as type 1 diabetes, the insulin-dependent form, or type 2 diabetes, which is non-insulin-dependent in character. Subjects with type 1 diabetes are hyperglycemic and hypoinsulinemic, and the conventional treatment for this form of the disease is to provide insulin. However, in some patients with type 1 or type 2 diabetes, absolute or relative elevated glucagon levels have been shown to contribute to the hyperglycemic state. Both in healthy control animals as well as in animal models of type 1 and type 2 diabetes, removal of circulating glucagon with selective and specific antibodies has resulted in reduction of the glycemic level. Mice with a homozygous deletion of the glucagon receptor exhibit increased glucose tolerance. Also, inhibition of glucagon receptor expression using antisense oligonucleotides ameliorates diabetic syndrome in db/db mice. These studies suggest that glucagon suppression or an action that antagonizes glucagon could be a useful adjunct to conventional treatment of hyperglycemia in diabetic patients. The action of glucagon can be suppressed by providing an antagonist or an inverse agonist, i.e. substances that inhibit or prevent constitutive, or glucagon-induced, glucagon receptor mediated responses.

Several publications disclose peptides that are stated to act as glucagon antagonists. Peptide antagonists of peptide hormones are often potent; however they are generally known not to be orally available because of degradation by physiological enzymes and poor distribution in vivo. Therefore, orally available non-peptide antagonists of peptide hormones are generally preferred.

A number of publications have appeared in recent years reporting non-peptide agents that act at the glucagon receptor. In spite of the number of treatments for diseases that involve glucagon, the current therapies suffer from one or more inadequacies, including poor or incomplete efficacy, unacceptable side effects, and contraindications for certain patient populations. Thus, there remains a need for an improved treatment using alternative or improved pharmaceutical agents that modulate glucagon receptor activity and treat the diseases that could benefit from glucagon receptor modulation. The present invention provides such a contribution to the art based on the finding that a novel class of compounds has a high affinity, selective, and potent inhibitory activity at the glucagon receptor. The present invention is distinct in the particular structures and their activities.

SUMMARY OF THE INVENTION

The present invention provides a compound structurally represented by Formula I:

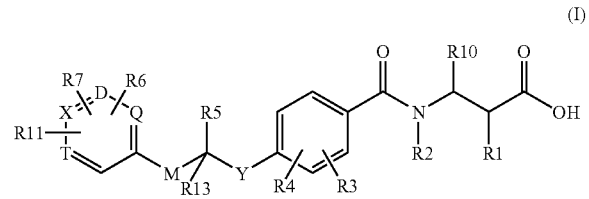

or a pharmaceutically acceptable salt thereof wherein:

Y is —O—, —S—, —CH$_2$—, —CH$_2$—O—, —CH═CH—, —CH$_2$—CH$_2$—, or a bond, provided that Y is a bond only when M is a bond;

M is a bond or —CH$_2$—;

Q, D, X, and T independently represent carbon (substituted with hydrogen or the optional substituents as indicated herein) or nitrogen, provided that no more than two of Q, D, X, and T are nitrogen;

R1 is —H, —OH, or -halogen;

R2 is —H or —(C$_1$-C$_3$) alkyl(optionally substituted with 1 to 3 halogens);

R3 and R4 are independently at each occurrence —H, -halogen, —CN, —(C$_1$-C$_7$) alkoxy, —(C$_1$-C$_7$) alkyl (optionally substituted with 1 to 3 halogens), or —(C$_2$-C$_7$) alkenyl;

R5 is selected from the group consisting of

—H, —(C$_1$-C$_{12}$) alkyl(optionally substituted with 1 to 3 halogens), —(C$_3$-C$_{12}$)cycloalkyl, -phenyl, -phenyl-phenyl-(C$_1$-C$_{12}$)alkyl(optionally substituted with 1 to 3 halogens), -aryl, aryl-(C$_1$-C$_{12}$)alkyl(optionally substituted with 1 to 3 halogens), -heteroaryl, heteroaryl-(C$_1$-C$_{12}$)alkyl(optionally substituted with 1 to 3 halogens), —(C$_2$-C$_{12}$)alkenyl (wherein optionally the —(C$_2$-C$_{12}$) alkenyl substituent can combine with the carbon to which it is attached to form a double bond), —(C$_3$-C$_{12}$) cycloalkenyl, -heterocycloalkyl, -aryl-(C$_2$-C$_{10}$)alkenyl, -heteroaryl-(C$_2$-C$_{10}$)alkenyl, —(C$_2$-C$_{12}$)alkynyl, —(C$_3$-C$_{12}$)cycloalkynyl, -aryl-(C$_2$-C$_{12}$)alkynyl, and -heteroaryl-(C$_2$-C$_{12}$)alkynyl, and wherein —(C$_1$-C$_{12}$) alkyl, —(C$_3$-C$_{12}$)cycloalkyl, -phenyl, -phenyl-phenyl-(C$_1$-C$_{12}$)alkyl, -aryl, -aryl-(C$_1$-C$_{12}$)alkyl, -heteroaryl, -heteroaryl-(C$_1$-C$_{12}$)alkyl, -heterocycloalkyl, —(C$_2$-C$_{12}$)alkenyl , —(C$_3$-C$_{12}$)cycloalkenyl, -aryl-(C$_2$-C$_{10}$) alkenyl, -heteroaryl-(C$_2$-C$_{10}$)alkenyl, —(C$_2$-C$_{12}$)alkynyl, —(C$_3$-C$_{12}$) cycloalkynyl, -aryl-(C$_2$-C$_{12}$)alkynyl, -heteroaryl-($C_2$-$C_{12}$)alkynyl are each optionally substituted with from one to three substituents each independently selected from the group consisting of -hydrogen, -hydroxy, cyano, nitro, -halo, -oxo, —($C_1$-$C_7$)alkyl, —($C_1$-$C_7$)alkyl-COOR12, —($C_1$-$C_7$)alkoxy, —($C_3$-$C_7$)cycloalkyl, -aryloxy, -aryl, -aryl-($C_1$-$C_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R6 and R7 are independently at each occurrence
—H, -halogen, -hydroxy, —CN, —($C_1$-$C_7$) alkoxy, —($C_2$-$C_7$)alkenyl, —($C_1$-$C_7$)alkyl(optionally substituted with 1 to 3 halogens), provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

R8 and R9 are independently at each occurrence selected from the group consisting of
-hydrogen, -hydroxy, —CN, -nitro, -halo, —($C_1$-$C_7$)alkyl (optionally substituted with 1 to 3 halogens), —($C_1$-$C_7$) alkoxy, —($C_3$-$C_7$)cycloalkyl(optionally substituted with 1 to 3 halogens), -aryl, aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$; and wherein —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, are each optionally substituted with from one to three substituents independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-($C_1$-$C_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R10 is selected from the group consisting of
—H, —($C_1$-$C_{12}$)alkyl(optionally substituted with 1 to 3 halogens), -cycloalkyl, -aryl, -aryl-($C_1$-$C_7$)alkyl, -heteroaryl, -heteroaryl-($C_1$-$C_7$)alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$) alkynyl, and -heteroaryl-($C_2$-$C_{12}$)alkynyl, and wherein —($C_1$-$C_{12}$)alkyl, -cycloalkyl, -aryl, -aryl-($C_1$-$C_7$)alkyl, -heteroaryl, -heteroaryl-($C_1$-$C_7$)alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, are each optionally substituted with from one to three substituents each independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-$C_1$-$C_7$ alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R11 is independently
—H, or

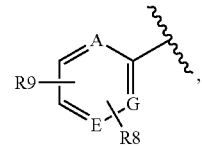

wherein A, G, and E independently represent carbon (substituted with hydrogen or the optional substituents as indicated herein) or nitrogen, provided that no more than two of A, G, and E are nitrogen; provided however that wherein A is nitrogen, then R8 or R9 are not attached to A, and provided that wherein G is nitrogen, then R8 or R9 are not attached to G, and provided that wherein E is nitrogen, then R8 or R9 are not attached to E;

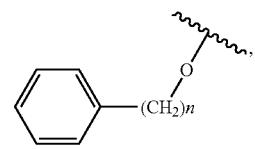

wherein n is an integer of 0, 1, 2, or 3, and when n is 0 m is a bond, and wherein the phenyl ring is optionally substituted 0 to 4 times with ($C_1$-$C_3$)alkyl; and

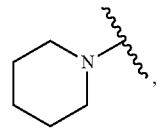

wherein the piperidinyl ring is optionally substituted 0 to 4 times with ($C_1$-$C_3$)alkyl;
wherein the zig-zag marks show the point of attachment to the parent molecule, and provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X;

R12 is independently at each occurrence selected from the group consisting of
-hydrogen, —($C_1$-$C_7$) alkyl(optionally substituted with 1 to 3 halogens), and -aryl; and
R13 is independently —H or —OH, provided that R13 is —OH only when M is a bond and Y is a bond.

The present invention provides compounds that are useful as glucagon receptor antagonists or inverse agonists. The present invention further provides compounds that are selective antagonists or inverse agonists of the glucagon receptor over the GLP-1 receptor. The present invention further provides a pharmaceutical composition which comprises a compound of Formula I, or a pharmaceutical salt thereof, and a pharmaceutically acceptable carrier, diluent, or excipient.

Due to their interaction with the glucagon receptor, the present compounds are useful in the treatment of a wide range of conditions and disorders in which an interaction with the glucagon receptor is beneficial. These disorders and conditions are defined herein as "diabetic and other glucagon related metabolic disorders". One of skill in the art is able to identify "diabetic and other glucagon related metabolic disorders" by the involvement of glucagon receptor mediated signaling either in the pathophysiology of the disorder, or in the homeostatic response to the disorder. Thus, the compounds may find use for example to prevent, treat, or alleviate, diseases or conditions or associated symptoms or sequelae, of the endocrinological system, the central nervous system, the peripheral nervous system, the cardiovascular system, the pulmonary system, and the gastrointestinal system, while reducing and or eliminating one or more of the unwanted side effects associated with the current treatments. "Diabetic and other glucagon related metabolic disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-/hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-/macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrythmia, premature death, anti-apoptosis, wound healing, impaired glucose tolerance (IGT), insulin resistance syndromes, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting the glucagon receptor; for use in inhibiting a glucagon receptor mediated cellular response in a mammal; for use in reducing the glycemic level in a mammal; for use in treating a disease arising from excessive glucagon; for use in treating diabetic and other glucagon related metabolic disorders in a mammal; and for use in treating diabetes, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting the glucagon receptor; for the manufacture of a medicament for inhibiting a glucagon receptor mediated cellular response in a mammal; for the manufacture of a medicament for reducing the glycemic level in a mammal; for the manufacture of a medicament for treating a disease arising from excessive glucagon; for the manufacture of a medicament for treating diabetic and other glucagon related metabolic disorders in a mammal; and for the manufacture of a medicament for preventing or treating diabetes, obesity, hyperglycemia, atherosclerosis, ischemic heart disease, stroke, neuropathy, and improper wound healing.

The present invention further provides a method of treating conditions resulting from excessive glucagon in a mammal; a method of inhibiting the glucagon receptor in a mammal; a method of inhibiting a glucagon receptor mediated cellular response in a mammal; a method of reducing the glycemic level in a mammal; a method of treating diabetic and other glucagon related metabolic disorders in a mammal; a method of preventing or treating diabetes, obesity, hyperglycemia, atherosclerosis, ischemic heart disease, stroke, neuropathy, and improper wound healing; said methods comprising administering to a mammal in need of such treatment a glucagon receptor-inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting the glucagon receptor; adapted for use in inhibiting glucagon receptor mediated cellular responses; adapted for use in reducing the glycemic level in a mammal; adapted for use in treating diabetic and other glucagon related metabolic disorders in a mammal; and adapted for use in preventing or treating diabetes, obesity, hyperglycemia, atherosclerosis, ischemic heart disease, stroke, neuropathy, and wound healing.

The compound or salt of the present invention further provides a diagnostic agent for identifying patients having a defect in the glucagon receptor, as a therapy to increase gastric acid secretions, and to reverse intestinal hypomobility due to glucagon administration. The invention also provides a method for the treatment of disorders or diseases, wherein a glucagon antagonistic action is beneficial, the method comprising administering to a subject in need thereof an effective amount of a compound according to the invention. In another embodiment of the invention, the present compounds are used for the preparation of a medicament for the treatment of any glucagon-mediated conditions and diseases. In another embodiment of the invention, the present compounds are used for the preparation of a medicament for the treatment of hyperglycemia. In yet another embodiment of the invention, the present compounds are used for the preparation of a medicament for lowering blood glucose in a mammal. The present compounds are effective in lowering the blood glucose, both in the fasting and the postprandial stage. In still another embodiment of the invention, the present compounds are used for the preparation of a pharmaceutical composition for the treatment of IGT. In a further embodiment of the invention, the present compounds are used for the preparation of a pharmaceutical composition for the treatment of type 2 diabetes. In yet a further embodiment of the invention the present compounds are used for the preparation of a pharmaceutical composition for the delaying or prevention of the progression from IGT to type 2 diabetes. In yet another embodiment of the invention the present compounds are used for the preparation of a pharmaceutical composition for the delaying or prevention of the progression from non-insulin requiring type 2 diabetes to insulin requiring type 2 diabetes. In a further embodiment of the invention the present compounds are used for the preparation of a pharmaceutical composition for the treatment of type 1 diabetes. Such treatment is normally accompanied by insulin therapy. In yet a further embodiment of the invention the present compounds are used for the preparation of a pharmaceutical composition for the treatment of obesity. In still a further embodiment of the invention the present compounds are used for the preparation of a pharmaceutical composition for the treatment of disorders of the lipid metabolism. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise.

DETAILED DESCRIPTION OF THE INVENTION

General terms used in the description of compounds, compositions, and methods herein described, bear their usual meanings. Throughout the instant application, the following terms have the indicated meanings:

"GLP-1" means glucagon-like peptide 1. The term "glucagon receptor" means one or more receptors that interact specifically with glucagon to result in a biological signal. The term "GLP-1 receptor" means one or more receptors that interacts specifically with glucagon-like peptide 1 to result in a biological signal.

The term "glucagon receptor antagonist" means a compound of the present invention with the ability to block cAMP production in response glucagon. The term "glucagon receptor inverse agonist" means a compound of the present invention with the ability to inhibit the constitutive activity of glucagon receptor. The term "selective" antagonist or inverse agonist means a compound having greater affinity for the glucagon receptor as compared to the affinity for the GLP-1 receptor.

In the general formulae of the present document, the general chemical terms have their usual meanings. For example;

"Halogen" or "halo" means fluoro, chloro, bromo and iodo.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. "$(C_1-C_3)$ alkyl" are one to three carbon atoms, such as methyl, ethyl, propyl, n-propyl, isopropyl, and the like and branched or isomeric forms thereof, and optionally may be substituted with one to three halogens or a designated number of substituents as set forth in the embodiments recited herein, "$(C_1-C_7)$ alkyl" are one to seven carbon atoms such as methyl, ethyl, propyl, n-propyl, isopropyl, n-butyl, isobutyl, sec-butyl and tert-butyl, pentyl, isopentyl, hexyl, heptyl, and the like, and branched or isomeric forms thereof, and optionally may be substituted with one to three halogens or a designated number of substituents as set forth in the embodiments recited herein, and "$(C_1-C_{10})$ alkyl" are one to ten carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein. "$(C_1-C_{12})$ alkyl" are one to twelve carbon atoms, such as methyl, ethyl, propyl, butyl, pentyl, hexyl, heptyl, nonyl, decyl, and the like, and branched or isomeric forms thereof, and optionally may be substituted with one to three halogens or a designated number of substituents as set forth in the embodiments recited herein.

The term "$(C_3-C_{12})$ cycloalkyl" refers to a saturated or partially saturated carbocycle containing one or more rings of from 3 to 12 carbon atoms, typically 3 to 7 carbon atoms optionally substituted with up to three halogens. Examples of $(C_3-C_{12})$ cycloalkyl include but are not limited to cyclopropyl, cyclobutyl, cyclopentyl, cyclohexyl and cycloheptyl, and the like. "$(C_3-C_7)$ cycloalkyl" means a ring with three to seven carbon atoms such as cyclopropyl, cyclobutyl, cyclopentyl and cyclohexyl, cycloheptyl, and the like, optionally substituted with up to three halogens.

The term "$(C_1-C_7)$ alkoxy" represents an alkyl group of one to seven carbon atoms attached through an oxygen bridge, such as methoxy, ethoxy, propoxy, isopropoxy, butoxy, tert-butoxy, pentoxy, and the like, and may be optionally substituted with three halogens or a designated number of substituents as set forth in the embodiments recited herein.

The term "$(C_2-C_{10})$ alkenyl" or "$(C_2-C_{10})$ alkylenyl" means hydrocarbon chain of two to ten carbon atoms of either a straight or branched configuration having at least one carbon-carbon double bond which may occur at any point along the chain, such as ethenyl, propenyl, butenyl, pentenyl, vinyl, alkyl, 2-butenyl and the like, and may be optionally substituted with one to three halogens or a designated number of substituents as set forth in the embodiments recited herein. The term "$(C_2-C_{12})$ alkenyl" or "$(C_2-C_{12})$ alkylenyl" means hydrocarbon chain of two to twelve carbon atoms of either a straight or branched configuration having at least one carbon-carbon double bond which may occur at any point along the chain, such as ethenyl, propenyl, butenyl, pentenyl, vinyl, alkyl, 2-butenyl and the like, and may be optionally substituted with one to three halogens or a designated number of substituents as set forth in the embodiments recited herein.

The term "$(C_3-C_{12})$ cycloalkenyl" refers to a partially saturated carbocycle containing one or more rings of from 3 to 12 carbon atoms, typically 3 to 7 carbon atoms optionally substituted with up to three halogens.

The term "$(C_2-C_{12})$ alkynyl" means a hydrocarbon chain of two to twelve carbon atoms of either a straight or branched configuration and having at least one carbon-carbon triple bond, which may occur at any point along the chain. Example of alkynyl is acetylene. Alkynyl as defined above may be optionally substituted with up to three halogens or the designated number of substituents as set forth in the embodiments recited herein.

The term "$(C_3-C_{12})$ cycloalkynyl" refers to a carbocycle containing one or more rings of from 3 to 12 carbon atoms, typically 3 to 7 carbon atoms, having at least one carbon-carbon triple bond which may occur at any point along the chain or ring, optionally substituted with up to three halogens. Cycloalkynyl as defined above may be optionally substituted with the designated number of substituents as set forth in the embodiments recited herein.

The term "aryl" includes carbocyclic aromatic ring systems (e.g. phenyl), fused polycyclic aromatic ring systems (e.g. naphthyl and anthracenyl), and aromatic ring systems fused to carbocyclic non-aromatic ring systems (e.g., 1,2,3, 4-tetrahydronaphthyl). "Aryl" as defined above may be optionally substituted with a designated number of substituents as set forth in the embodiments recited herein.

The term "aryloxy" refers to an aryl group which is linked to the parent molecule through an oxygen bridge.

The term "heteroaryl" group, as used herein, is an aryl ring system having at least one heteroatom such as nitrogen, sulfur, or oxygen, and includes monocyclic, bicyclic, or tricyclic aromatic rings of 5 to 14 carbon atoms containing one or more heteroatoms selected from the group consisting of O, N, and S. The "heteroaryl" as defined above may be optionally substituted with a designated number of substituents as set forth in the embodiments recited herein. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline, and the like.

The term "arylalkyl" refers to an aryl group which is linked to the parent molecule through an alkyl moiety, and "arylalkyl" may be further optionally substituted with a designated number of substituents as set forth in the embodiments recited herein.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N, or S.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the hererin defined terms may occur more than once in the structural formulae, and upon such occurrence each term shall be defined independently of the other.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The term "a glucagon receptor mediated cellular response" includes various responses by mammalian cells to glucagon stimulation or glucagon receptor activity. For example "glucagon receptor mediated cellular responses," include but are not limited to, release of glucose from liver, or other cells, in response to glucagon stimulation or glucagon receptor activity. One of ordinary skill in the art can readily identify other cellular responses mediated by glucagon receptor activity, for example by observing a change in the responsive cellular endpoint after contacting the cell with an effective dose of glucagon.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

In one embodiment, the present invention provides compounds of Formula I as described in detail herein. While all of the compounds of the present invention are useful, certain of the compounds are particularly interesting and are preferred. The following listing sets out several groups of preferred compounds. It will be understood that each of the listings may be combined with other listings to create additional groups of preferred embodiments. Other embodiments are, 1. wherein Y is —O—,
2. wherein Y is —S—,
3. wherein Y is —CH$_2$—,
4. wherein Y is —CH$_2$—O—,
5. wherein Y is —C≡C—,
6. wherein Y is —CH$_2$—CH$_2$—,
7. wherein Y is a bond, provided that Y is a bond only when M is a bond,
8. wherein M is a bond,
9. wherein M is —CH$_2$—,
10. wherein M is a bond and Y is a bond,
11. wherein M is a bond and Y is —O—,
12. wherein D, Q, X, and T are carbon (substituted with hydrogen or the optional substituents as indicated herein),
13. wherein X is carbon and Rh is attached to X,
14. wherein D is carbon and R11 is attached to D,
15. wherein X is carbon and R11 is attached to X and R11 is selected from the group consisting of

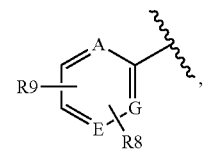

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen;

16. wherein X is carbon and R11 is attached to X and R11 is selected from the group consisting of

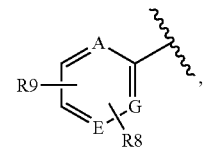

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$, 17. wherein X is carbon and R11 is attached to X and R11 is selected from the group consisting of

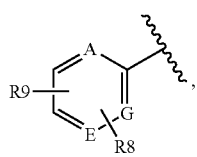

wherein the zig-zag mark shows the point of attachment to the parent molecule, and wherein A, G, and E independently represent carbon (substituted with hydrogen or the optional substituents as indicated herein) or nitrogen, provided that no more than two of A, G, and E are nitrogen, and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, 18. wherein X is carbon and R11 is attached to X and R11 is selected from the group consisting of

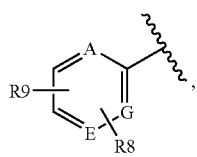

wherein the zig-zag mark shows the point of attachment to the parent molecule, and wherein A, G, and E are carbon (substituted with hydrogen or the optional substituents as indicated herein), 19. wherein X is carbon and R11 is attached to X and R11 is selected from the group consisting of

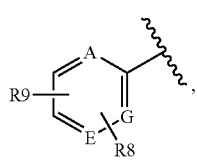

wherein the zig-zag mark shows the point of attachment to the parent molecule, and wherein A, G, and E are carbon (substituted with hydrogen or the optional substituents as indicated herein), and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$, 20. wherein X is carbon and R11 is attached to X and R11 is selected from the group consisting of

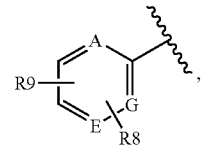

wherein the zig-zag mark shows the point of attachment to the parent molecule, and wherein A, G, and E are carbon (substituted with hydrogen or the optional substituents as indicated herein), and R8 and R9 are independently at each occurrence selected from the group consisting of -hydrogen, -hydroxy, —CN, -nitro, -halo, —($C_1$-$C_7$)alkyl, —($C_1$-$C_7$)alkoxy, —($C_3$-$C_7$)cycloalkyl, 21. wherein X is carbon, and R11 is attached to X, and R11 is

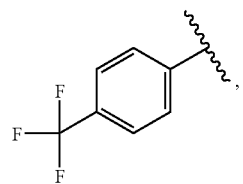

wherein the zig-zag mark shows the point of attachment to the parent molecule, 22. wherein X is carbon, and R11 is attached to X, and R11 is

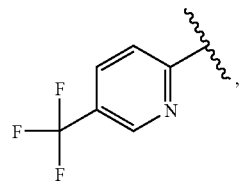

wherein the zig-zag mark shows the point of attachment to the parent molecule, 23. wherein one of D, X, Q, or T is nitrogen,
24. wherein D is nitrogen,
25. wherein X is nitrogen,
26. wherein Q is nitrogen,
27. wherein T is nitrogen,
28. wherein two of D, X, Q, and T are nitrogen,
29. wherein D and T are nitrogen,
30. wherein Q and X are nitrogen,
31. wherein R1 is hydrogen,
32. wherein R1 is —OH,
33. wherein R1 is halogen,
34. wherein R2 is hydrogen,
35. wherein R2 is —($C_1$-$C_3$) alkyl,
36. wherein R3 is hydrogen,
37. wherein R3 is halogen,
38. wherein R4 is hydrogen,
39. wherein R4 is halogen, 40. wherein R3 is selected from the group consisting of
—($C_1$-$C_7$) alkoxy, —($C_1$-$C_7$) alkyl, —($C_2$-$C_7$) alkenyl, 41. wherein R4 is selected from the group consisting of
—($C_1$-$C_7$) alkoxy, —($C_1$-$C_7$) alkyl, —($C_2$-$C_7$) alkenyl, 42. wherein R5 is selected from the group consisting of
—H, —($C_1$-$C_{12}$) alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$)alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, 43. wherein R5 is selected from the group consisting of
—($C_1$-$C_{12}$) alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$)alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, 44. wherein R5 is selected from the group consisting of
—($C_1$-$C_{12}$) alkyl, —($C_3$-$C_{12}$)cycloalkyl, —($C_2$-$C_{12}$)alkenyl, —($C_3$-$C_{12}$)cycloalkenyl, -heterocycloalkyl, —($C_2$-$C_{12}$)alkynyl, —($C_3$-$C_{12}$)cycloalkynyl, 45. wherein R5 is selected from the group consisting of
—H, —($C_1$-$C_{12}$) alkyl, —($C_3$-$C_{12}$)cycloalkyl, -phenyl, -phenyl-phenyl-($C_1$-$C_{12}$)alkyl, —($C_2$-$C_{12}$)alkenyl, —($C_3$-$C_{12}$)cycloalkenyl, -heterocycloalkyl, —($C_2$-$C_{12}$)alkynyl, —($C_3$-$C_{12}$)cycloalkynyl, 46. wherein R10 is selected from the group consisting of
—H, —($C_1$-$C_{12}$)alkyl, -cycloalkyl, -aryl, -aryl-($C_1$-$C_7$)alkyl, -heteroaryl, -heteroaryl —($C_1$-$C_7$)alkyl, -($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, 47. wherein R10 is selected from the group consisting of
—H, —($C_1$-$C_{12}$)alkyl, -cycloalkyl, —($C_2$-$C_{12}$)alkenyl, —($C_3$-$C_{12}$)cycloalkenyl, -aryl-($C_2$-$C_{10}$)alkenyl, —($C_2$-$C_{12}$)alkynyl, —($C_3$-$C_{12}$)cycloalkynyl, 48. wherein R10 is —H, 49. Wherein R13 is —H, 50. A compound of Formula (II)

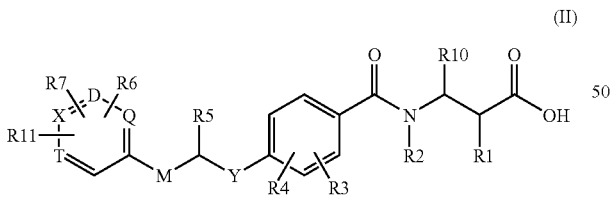

(II)

or pharmaceutically acceptable salts thereof wherein:

Y is —O—, —S—, —$CH_2$—, —$CH_2$—O—, —C=C—, or —$CH_2$—$CH_2$—;

M is a bond, or —$CH_2$—;

Q, D, X and T independently represent carbon or nitrogen, provided that no more than two of Q, D, X and T are nitrogen;

R1 is —H, —OH, or -halogen;

R2 is —H, or —($C_1$-$C_3$) alkyl;

R3 and R4 are independently at each occurrence
—H, -halogen, —CN, —($C_1$-$C_7$) alkoxy, —($C_1$-$C_7$) alkyl, —($C_2$-$C_7$) alkenyl;

R5 is selected from the group consisting of
—H, —($C_1$-$C_{12}$) alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, —($C_2$-$C_{12}$)alkenyl, —($C_3$-$C_{12}$)cycloalkenyl, -heterocycloalkyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, and wherein —($C_1$-$C_{12}$)alkyl, —($C_3$-$C_{12}$)cycloalkyl, -phenyl, -phenyl-phenyl-($C_1$-$C_{12}$)alkyl, -aryl, -aryl-($C_1$-$C_{12}$)alkyl, -heteroaryl, -heteroaryl-($C_1$-$C_{12}$)alkyl, -heterocycloalkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$) cycloalkynyl, -aryl-($C_2$-$C_{12}$)alkynyl, -heteroaryl-($C_2$-$C_{12}$)alkynyl, are each optionally substituted with from one to three substituents each independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxy, —($C_3$-$C_7$)cycloalkyl, -aryloxy, -aryl, -aryl-($C_1$-$C_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R6 and R7 are independently at each occurrence
—H, -halogen, -hydroxy, —CN, —($C_1$-$C_7$) alkoxy, —($C_2$-$C_7$)alkenyl, —($C_1$-$C_7$)alkyl, provided however that wherein D is nitrogen, then R6 or R7 are not attached to D, and provided that wherein T is nitrogen, then R6 or R7 are not attached to T, and provided that wherein Q is nitrogen, then R6 or R7 are not attached to Q, and provided that wherein X is nitrogen, then R6 or R7 are not attached to X;

R8 and R9 are independently at each occurrence selected from the group consisting of
-hydrogen, -hydroxy, —CN, -nitro, -halo, —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$; and wherein —($C_1$-$C_7$)alkyl, —($C_1$-$C_7$)alkoxy, —($C_3$-$C_7$)cycloalkyl, -aryl, -aryl-($C_1$-$C_7$)alkyl, -heteroaryl, -heteroaryl-($C_1$-$C_7$)alkyl, -aryloxy, are each optionally substituted with from one to three substituents independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-($C_1$-$C_7$)alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R10 is selected from the group consisting of
—H, —($C_1$-$C_{12}$)alkyl, -cycloalkyl, -aryl, -aryl-($C_1$-$C_7$)alkyl, -heteroaryl, -heteroaryl —($C_1$-$C_7$)alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, and wherein —($C_1$-$C_{12}$)alkyl, -cycloalkyl, -aryl, -aryl-($C_1$-$C_7$)alkyl, -heteroaryl, -heteroaryl —($C_1$-$C_7$)alkyl, —($C_2$-$C_{12}$)alkenyl, —($C_3$-$C_{12}$)cycloalkenyl, -aryl-($C_2$-$C_{10}$)alkenyl, -heteroaryl-($C_2$-$C_{10}$)alkenyl, —($C_2$-$C_{12}$)alkynyl, —($C_3$-$C_{12}$)cycloalkynyl, -aryl-($C_2$-$C_{12}$)alkynyl, -heteroaryl-($C_2$-$C_{12}$)alkynyl, are each optionally substituted with from one to three substituents each independently selected from the group consisting of -hydrogen, -hydroxy, -cyano, -nitro, -halo, -oxo, —($C_1$-$C_7$)alkyl, —($C_1$-$C_7$)alkyl-COOR12, —($C_1$-$C_7$)alkoxyl, —($C_3$-$C_7$)cycloalkyl, -aryloxy, -aryl, -aryl-$C_1$-$C_7$ alkyl, -heteroaryl, -heterocycloalkyl, —C(O)R12, —COOR12, —OC(O)R12, —OS(O)$_2$R12, —N(R12)$_2$, —NR12C(O)R12, —NR12SO$_2$R12, —SR12, —S(O)R12, —S(O)$_2$R12, and —S(O)$_2$N(R12)$_2$;

R11 is independently at each occurrence
—H, or

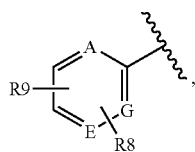

wherein the zig-zag mark shows the point of attachment to the parent molecule, and wherein A, G, and E independently represent carbon or nitrogen, provided that no more than two of A, G, and E are nitrogen; provided however that wherein D is nitrogen, then R11 is not attached to D, and provided that wherein T is nitrogen, then R11 is not attached to T, and provided that wherein Q is nitrogen, then R11 is not attached to Q, and provided that wherein X is nitrogen, then R11 is not attached to X; and provided however that wherein A is nitrogen, then R8 or R9 are not attached to A, and provided that wherein G is nitrogen, then R8 or R9 are not attached to G, and provided that wherein E is nitrogen, then R8 or R9 are not attached to E;

R12 is independently at each occurrence selected from the group consisting of
-hydrogen, —($C_1$-$C_7$) alkyl, -aryl.

As used herein, the term "stereoisomer" refers to a compound made up of the same atoms bonded by the same bonds but having different three-dimensional structures called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The compounds of the present invention may be chiral, and it is intended that any enantiomers, whether pure, partially purified, or racemic mixtures, are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of Formula I. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation "——◀" refers to a bond that protrudes forward out of the plane of the page. The designation "⋯⋯⫶" refers to a bond that protrudes backward out of the plane of the page. The designation "⁓⁓⁓" refers to a bond wherein the stereochemistry is not defined.

The compounds of Formula I, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I, can be prepared by one of ordinary skill in the art utilizing well known techniques and processes, such as those disclosed by J. Jacques, et al., "*Enantiomers, Racemates, and Resolutions*," John Wiley and Sons, Inc., 1981, and E. L. Eliel and S. H. Wilen, "*Stereochemistry of Organic Compounds*," (Wiley-Interscience 1994), and European Patent Application No. EP-A-838448, published Apr.

29, 1998. Examples of resolutions include recrystallization techniques or chiral chromatography. Unless otherwise indicated, a compound indicated to be "isomer 1" will be the first isomer eluted from the chiral separation column and "isomer 2" will be the second.

In general, the term "pharmaceutical" when used as an adjective means substantially non-toxic to living organisms. For example, the term "pharmaceutical salt" as used herein, refers to salts of the compounds of Formula I, which are substantially non-toxic to living organisms. See, e.g., Berge, S. M, Bighley, L. D., and Monkhouse, D. C., "Pharmaceutical Salts," *J. Pharm. Sci.*, 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts such as lysine, arginine and ornithine. Typical pharmaceutical salts include those salts prepared by reaction of the compounds of Formula I, with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I, prepared by reaction of a compound of Formula I, with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, ethanesulfonic acid, methanesulfonic acid, oxalic acid, p-bromophenylsulfonic acid, carbonic acid, succinic acid, citric acid, tartaric acid, benzoic acid, acetic acid and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The skilled artisan would appreciate that some compounds of Formula I, may be acidic in nature and accordingly react with any of a number of inorganic and organic bases to form pharmaceutical base addition salts. The term "base addition salt" refers to a salt of a compound of Formula I, prepared by reaction of a compound of Formula I, with a mineral or organic base. For exemplification of pharmaceutical base addition salts see, e.g., Berge, S. M, Bighley, L. D., and Monkhouse, D. C., *J. Pharm. Sci.*, 66:1, 1977. Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I. The potassium and sodium salt forms are particularly preferred. The present invention also contemplates pharmaceutical base addition salts of compounds of Formula I.

The pharmaceutical salts of the invention are typically formed by reacting a compound of Formula I, with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods. All pharmaceutically acceptable salts are contemplated in the present invention. The compound or salt of the present invention may form a solvate with low molecular weight solvents. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example Asp$^{B28}$ human insulin, U.S. Pat. No. 5,504,188 (Eli Lilly), for example Lys$^{B28}$ Pro$^{B29}$ human insulin, EP 368 187 (Aventis), for example Lantus®, which are all incorporated herein by reference, GLP-1 and GLP-1 derivatives such as those disclosed in WO 98/08871 (Novo Nordisk A/S), which is incorporated herein by reference, as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), which are incorporated herein by reference, GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069

In another embodiment, the present compounds are administered in combination with insulin or an insulin analogue or derivative, such as N$^{εB29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, glicazide and glyburide.

In another embodiment of the invention the present compounds are administered in combination with a biguanide for example metormin.

In yet another embodiment of the invention the present compounds are administered in combination with a meglitinide for example repaglinide or nateglinide.

In still another embodiment of the invention the present compounds are administered in combination with a thiazolidinedione insulin sensitizer for example troglitazone, ciglitazone, piolitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer for example such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor for example voglibose, emiglitate, miglitol or acarbose.

In another embodiment of the invention the present compounds are administered in combination with an agent acting on the ATP-dependent potassium channel of the β-cells for example tolbutamide, glibenclamide, glipizide, glicazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

In a further embodiment of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140 MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, H3 histamine antagonists, opioid antagonists (such as naltrexone), exendin-4, GLP-1 and ciliary neurotrophic factor (such as axokine), cannaboid receptor antagonist for example CB-1 (such as rimonabant). In another embodiment the antiobesity agent is dexamphetamine or amphetamine. In another embodiment the antiobesity agent is leptin. In another embodiment the antiobesity agent is fenfluramine or exfenfluramine. In still another embodiment the antiobesity agent is sibutramine. In a further embodiment the antiobesity agent is orlistat. In another embodiment the antiobesity agent is mazindol or phentermine. In still another embodiment the antiobesity agent is phendimetrazine, diethylpropion, fluoxetine, bupropion, topiramate or ecopipam.

Furthermore, the present compounds may be administered in combination with one or more antihypertensive agents. Examples of antihypertensive agents are β-blockers such as alprenolol, atenolol, timolol, pindolol, propranolol and metoprolol, SCE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

The compounds of the present invention may be administered in combination with FAS inhibitors.

The compounds of the present invention may also be administered in combination with chemical uncouplers, hormone sensitive lipase inhibitor, imidazolines, 11-β-hydroxysteroid dehydrogenase inhibitors, lipoprotein lipase activator, AMPK activators, immunosuppresive drugs, nicotinamide, ASIS, anti-androgens or carboxypeptidase inhibitors.

It should be understood that any suitable combination of the compounds according to the invention with diet and/or exercise, one or more of the above-mentioned compounds and optionally one or more other active substances are considered to be within the scope of the present invention.

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "eq" refers to equivalents; "N" refers to normal or normality, "M" refers to molar or molarity, "g" refers to gram or grams, "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to part per million downfield from tetramethylsilane; "MS" refers to mass spectrometry, Observed Mass indicates (M+1) unless indicated otherwise. "MS (FD)" refers to field desorption mass spectrometry, "MS (IS)" refers to ion spray mass spectrometry, "MS (FIA)" refers to flow injection analysis mass spectrometry, "MS (FAB)" refers to fast atom bombardment mass spectrometry, "MS (EI)" refers to electron impact mass spectrometry, "MS (ES)" refers to electron spray mass spectrometry, "UV" refers to ultraviolet spectrometry, "$^1$H NMR" refers to proton nuclear magnetic resonance spectrometry. In addition, "IR" refers to infra red spectrometry, and the absorption maxima listed for the IR spectra are only those of interest and not all of the maxima observed. "RT" refers to room temperature. "DEAD" refers to diethylazodicrboxylate. "PPh$_3$" refers to triphenylphosphine. "ADDP" refers to 1,1'-(azodicarbonyl)dipiperidine. "PPBu$_3$" refers to tributylphosphine. "OTF" refers to triflate. "LAH" refers to lithium aluminum hydride. "DIBAL-H" refers to diisobutylaluminum hydride. "KOtBu" refers to potassoium t-butoxide. "THF" refers to tetrahydrofuran. "TBP" refers to tributylphosphine. "EDCI" refers to 1-(3-dimethylaminopropyl)-3-ethylcarbodiamide hydrochloride. "DMAP" refers to dimethylaminopyridine. "HNMe(OMe)" refers to N,N,dimethylhydroxyamine. "CDMT" refers to 2-chloro-4,6-dimethoxy-[1,3,5]triazine. "NMM" refers to N-methyl morpholine. "DCM" refers to dichloromethane. "DMSO" refers to dimethylsulfoxide. "ET$_3$N" refers to triethylamine. "DMF" refers to dimethylformamide. "Et" in a formula refers to ethyl, for example Et$_2$0 refers to diethylether, and EtOAc refers to ethylacetate. "PyBOP" refers to bromo-tris-pyrrolidino-phosphonium hexafluorophosphate. "Me" refers to methyl as in MeOH which is methanol. "Pd/C" refers to 10% palladium on carbon.

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}C$ NMR are recorded on a Varian 400 MHz spectrometer at ambient temperature. Chemical shifts are reported in ppm from tetramethylsilane on the δ scale, with the solvent resonance employed as the internal standard ($CDCl_3$ at 77.0 ppm and DMSO-$d_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

GENERAL SCHEMES

Compounds of the present invention have been formed as specifically described in the examples. Further, many compounds are prepared as more generally using a) alkylation of phenol/thiophenol with a halide, b) a Mitsunobu protocol (O. Mitsunobu, 1981 Synthesis, p1); c) and other methods known to the skilled artisan. Alternative synthesis methods may also be effective and known to the skilled artisan. Unless otherwise indicated, all variables, such as M, Y', R1' to R13', etc., are as defined for analogous variables (R1 to R13, etc.) in the summary of the invention.

For example, an intermediate like A is alkylated with an alkylating agent B in the presence of a base (e.g. $K_2CO_3$, $Cs_2CO_3$ etc.). Hydrolysis in the presence of aqueous NaOH or LiOH gave the acid product.

Scheme 1

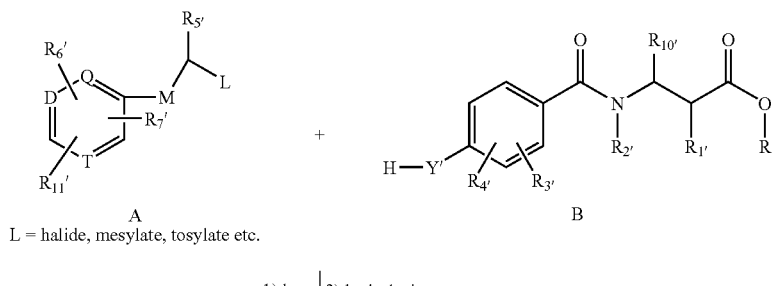

L = halide, mesylate, tosylate etc.

1) base  2) hydrolysis

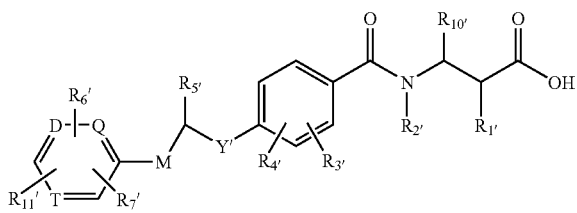

Alternatively, an intermediate like A is coupled with an alcohol C under Mitsunobu reaction condition (DEAD/$PPh_3$, ADDP/$PBu_3$ etc.). Hydrolysis in the presence of aqueous NaOH or LiOH gave the acid product:

Scheme 2

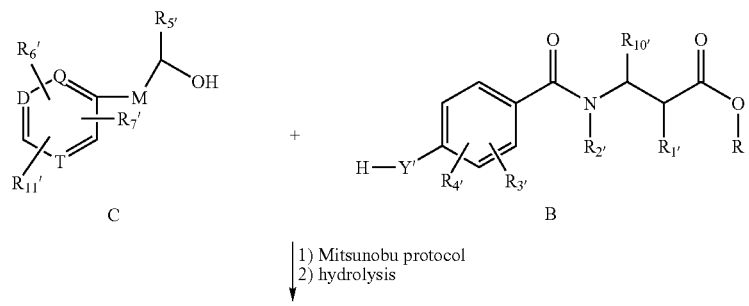

1) Mitsunobu protocol
2) hydrolysis

-continued

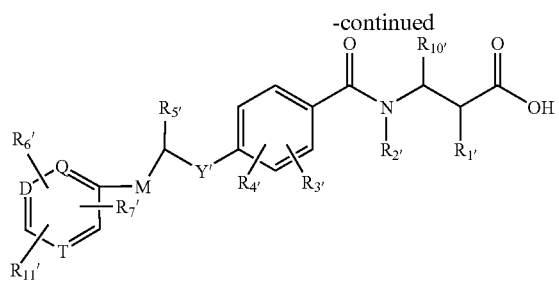

Under certain circumstances, the synthetic sequence can be altered, where an intermediate like D is coupled with an aryl boronic acid under Suzuki reaction conditions (Pd catalyst, base). Hydrolysis in the presence of aqueous NaOH or LiOH gave the acid product:

Scheme 3

$R_{11}''B(OR'')_2$ +

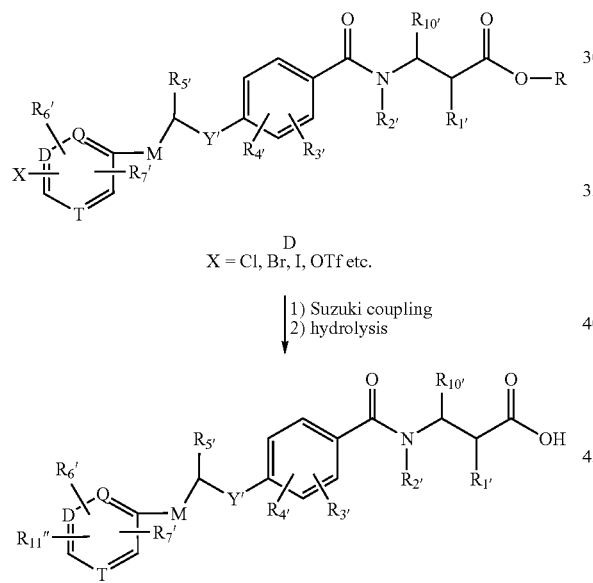

D
X = Cl, Br, I, OTf etc.

1) Suzuki coupling
2) hydrolysis

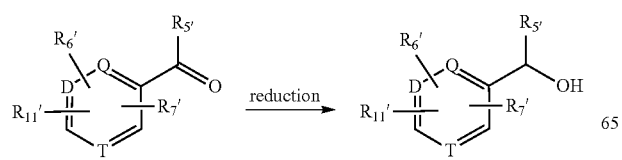

The alcohol intermediates A and C can be made by A) reduction of the ketone with or without chiral auxiliary or B) reduction of the ester to primary alcohol, oxidation to aldehyde followed by addition of a Grignard reagent.

Scheme 4

Method A

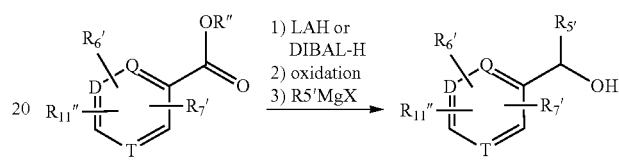

-continued

Method B

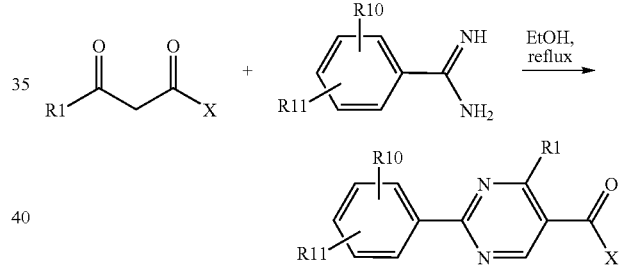

The pyrimidine analogues can also be prepared by reaction between a 1,3-diketone or β-ketoester and an appropriate benzamidine that is further prepared by the methods known to the art.

Scheme 5

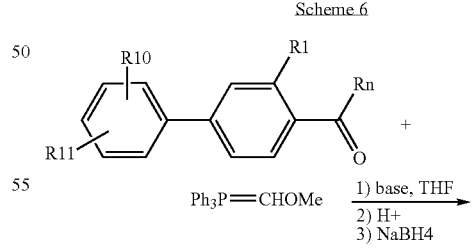

A Wittig reaction is used to homobenzylic alcohol analogs as shown in Scheme 5:

Scheme 6

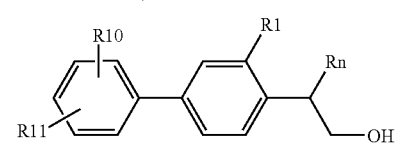

For example, the following scheme exemplified the synthesis of a compound in which M is a bond and Y is —CH$_2$—O—;

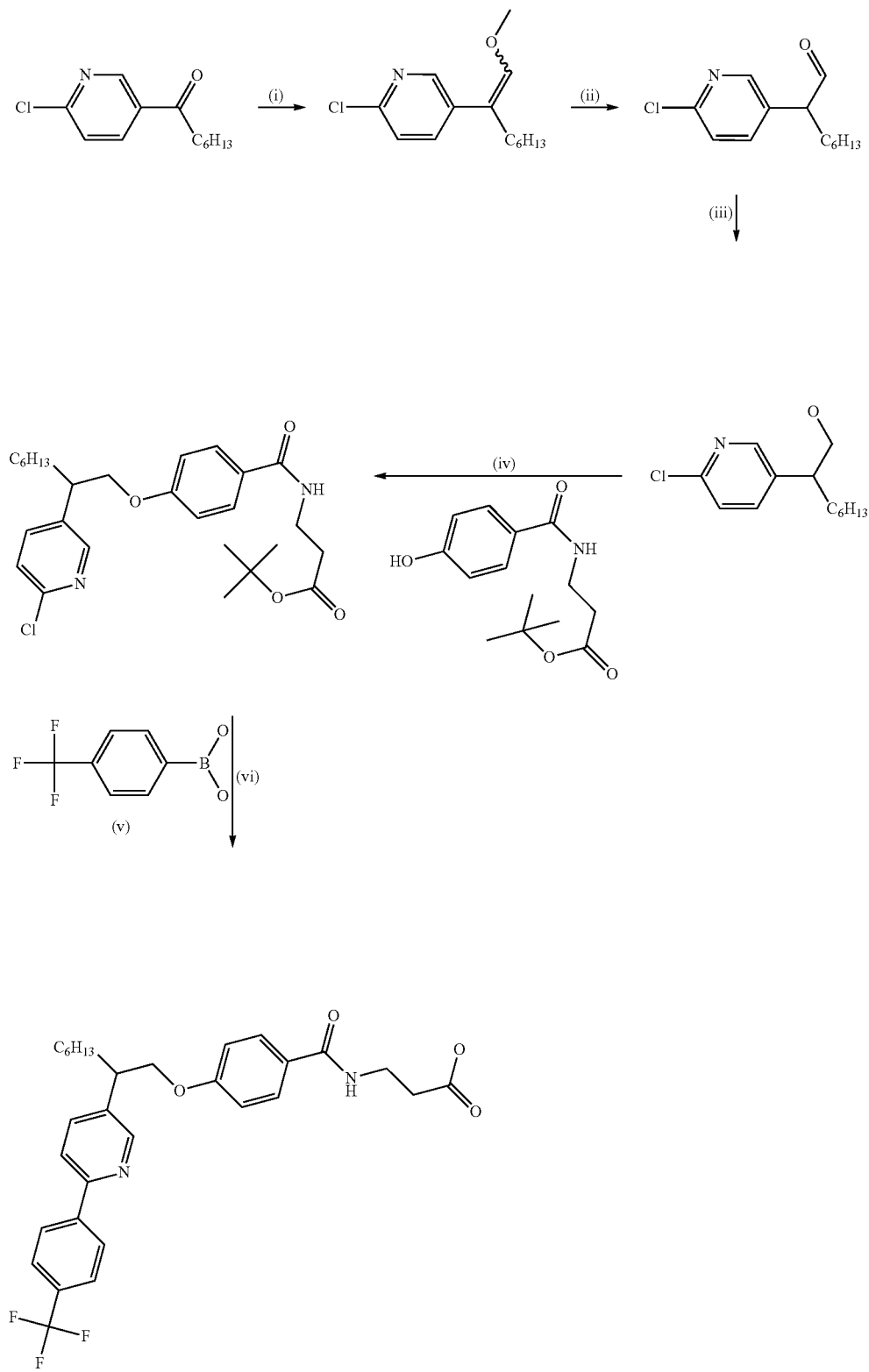
Scheme 7
(i) KOtBu, Ph3PCH2OCH3Cl, toluene;
(ii) HCl, THF, 50° C.;
(iii) NaBH4, EtOH;
(iv) Toluene, ADDP, TBP, 0° C.;
(v) Pd(PPh3)4, KF, Toluene:Water(1:1),
(vi) NaOH, THF, reflux.

A compound in which M is a bond and Y is a bond can be made in following route:
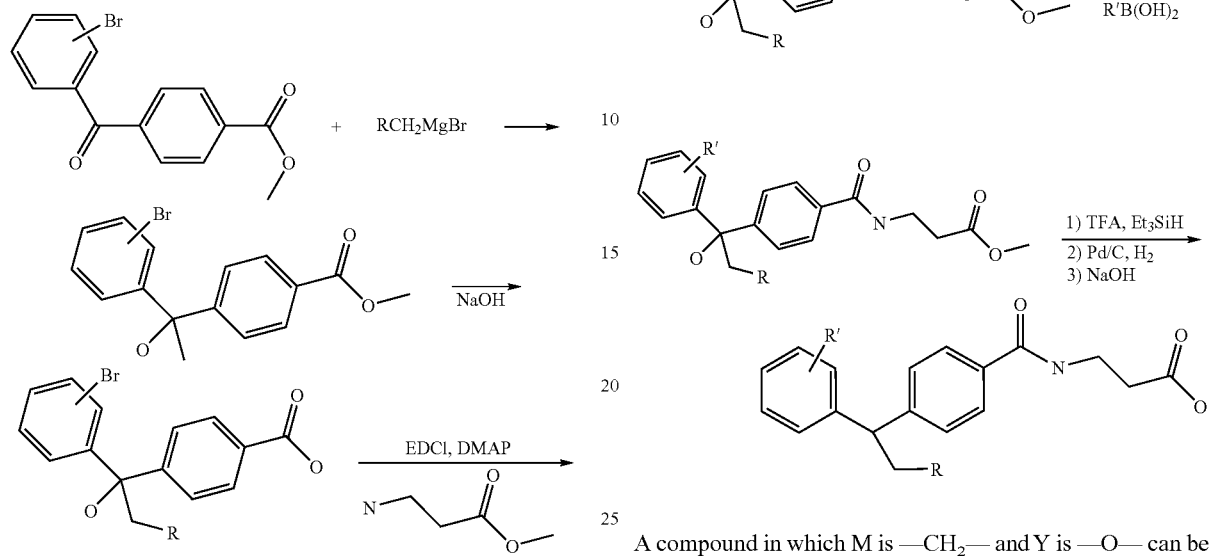
A compound in which M is —CH$_2$— and Y is —O— can be made in the following synthetic route:
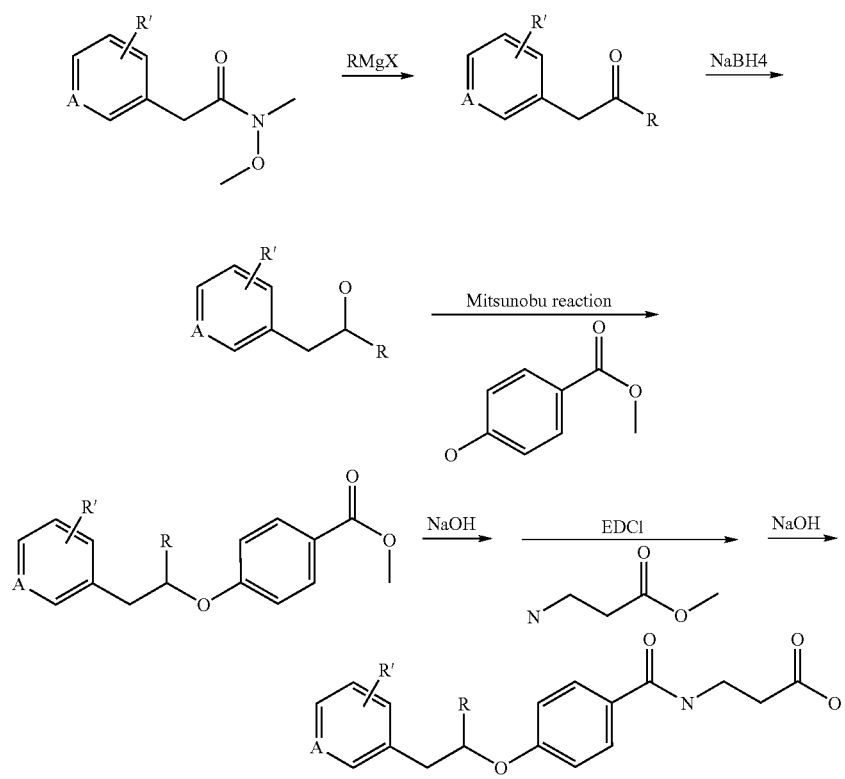

A compound in which M is a bond and Y is —CH═CH— can be made in following manner, Scheme 10

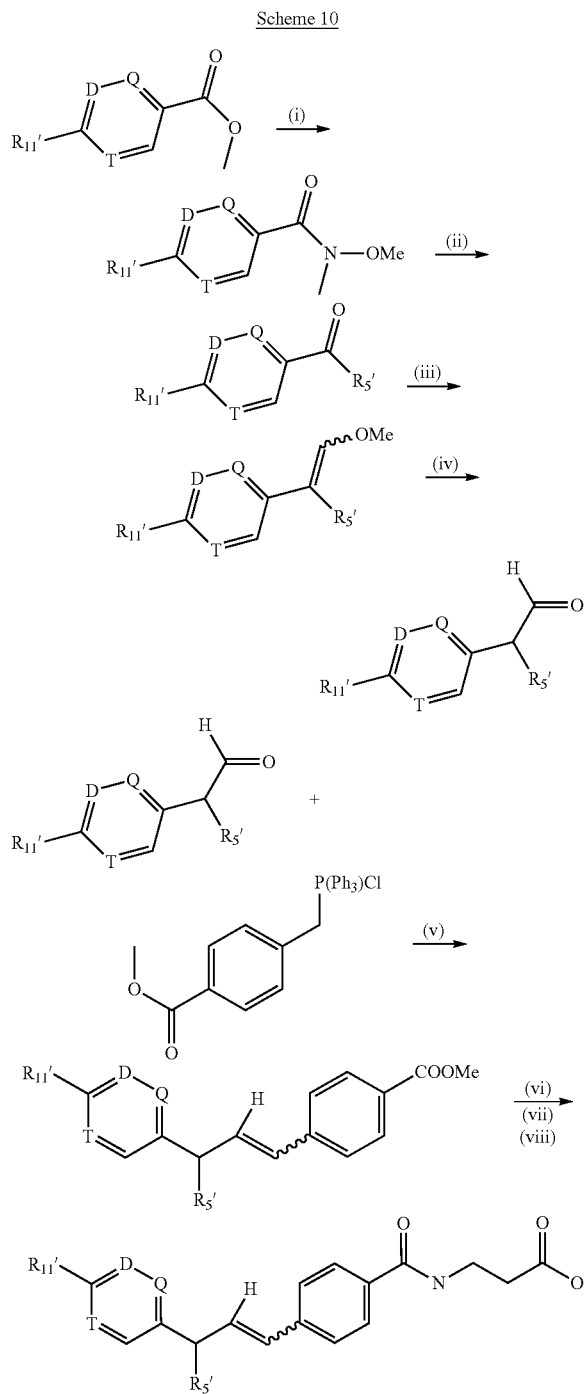

(i) iPrMgCl, THF, 0° C.;
(ii) CF₃CH₂CH₂MgBr, THF, 0° C.;
(iii) KOtBu, Ph₃PCH₂OCH₃Cl, toluene;
(iv) HCl, THF, 50° C.;
(v) KOtBu, toluene;
(vi) NaOH, THF, reflux;
(vii) beta-alanine methyl ester, CDMT, NMM, DCM;
(viii) NaOH, THF, reflux The enantiomeric purified products are prepared either through A) chiral chromatography or B) Mitsunobu coupling between a phenol or thiophenol and a chiral alcohol that can be prepared using the methods known to the art.

PREPARATIONS AND EXAMPLES

The Examples provided herein are illustrative of the invention claimed herein and are not intended to limit the scope of the claimed invention in any way. Names of the preparations and examples are derived using ChemDraw.

Preparation 1

Ethyl 3-(4-Hydroxybenzoylamino)propionate

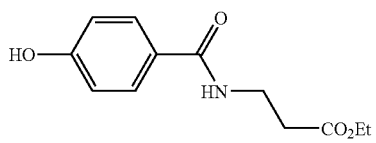

Diisopropylethylamine (DIPEA, 25.3 mL, 145 mmol) is added dropwise to a solution of EDCI (13.8 g, 72.5 mmol), 4-hydroxybenzoic acid (10.0 g, 72.5 mmol) and ethyl 3-aminopropionate (11.1 g, 72.5 mmol) in THF (700 mL) at room temperature under nitrogen, after which the mixture is stirred for 7 h. The mixture is diluted with water (200 mL) and saturated aqueous sodium bicarbonate solution (100 mL) and extracted with ethyl acetate (3×200 mL). The combined organic extracts are washed with water (100 mL) and brine (100 mL), dried (MgSO₄) and the solvents are removed under reduced pressure. The residue is purified by flash column chromatography on silica gel, eluting with hexanes/ethyl acetate (1:1 to 1:4), to afford ethyl 3-(4-hydroxybenzoylamino)propionate as a white crystalline solid (13.59 g, 79%): $^1$H NMR (CDCl$_3$, 300 MHz) δ 1.27 (t, J=7.14 Hz, 3H), 2.64 (t, J=6.16 Hz, 2H), 3.71 (dt, J=6.09, 11.85 Hz, 2H), 6.86 (d, J=8.70 Hz, 2H), 6.89-6.93 (m 1H), 7.63 (d, J=8.65 Hz, 2H), 8.21-8.27 (m, 1H); APCI MS m/z 238 [C$_{12}$H$_{15}$NO$_4$+H]$^+$.

Preparation 2

3-(4-Hydroxy-benzoylamino)-propionic acid methyl ester

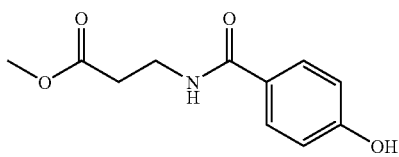

Step A. 3-(4-Benzyloxy-benzoylamino)-propionic acid methyl ester

To a mixture of 4-benzyloxybenzoic acid (8.92 g, 39.08 mmol) and 3-amino-propionic acid methyl ester hydrochloride (6.00 g, 42.98 mmol) in CH₂Cl₂ (100 mL) was added DMAP (catalytic), triethylamine (6.60 mL, 47.35 mmol), and EDCI (9.00 g, 46.94 mmol). The mixture was stirred at RT for 12 h. The mixture was diluted with CH₂Cl₂. The organics were washed with 1N HCl, 2N NaOH, water, and brine (1×100 mL each), and dried with MgSO$_4$ to yield 11.28 g (92%) of the title compound.

Step B. 3-(4-Hydroxy-benzoylamino)-propionic acid methyl ester

A mixture of 3-(4-benzyloxy-benzoylamino)-propionic acid methyl ester (11.26 g, 35.93 mmol) and Pd(OH)$_2$/C (20%, 3.19 g) in MeOH was heated at 40° C. for 12 h. The mixture was filtered through celite to yield 7.89 (98%) of the title compound. The following compound was made in a similar manner:

Preparation 3

(R,S)-1-(3-Methyl-4'-trifluoromethyl-biphenyl-4-yl)-ethanol

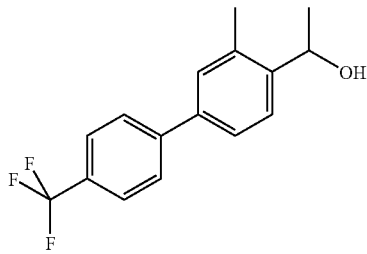

Step A. Trifluoro-methanesulfonic acid 4-acetyl-3-methyl-phenyl ester

To a 0° C. solution of 1-(4-hydroxy-2-methyl-phenyl)-ethanone (3.59 g, 23.93 mmol) in pyridine (25 mL) is added trifluoromethanesulfonic anhydride (10.0 g, 35.44 mmol) dropwise and warmed to room temperature overnight. TLC (10% EtOAc/hexane) indicates complete consumption of starting material. The reaction was quenched by pouring into ice/water mix and extracted with Et$_2$O (3×200 mL). The combined organic layers are washed with water, 1N HCl, water, brine, dried (MgSO$_4$), concentrated and chromatographed (330 g SiO$_2$, 5% EtOAc/Hexanes) to yield the title compound (6.35 g, 94%). $^1$NMR (400 MHz, CDCl$_3$) δ ppm: 7.76 (d, 1H, J=8.4 Hz), 7.19 (dd, 1H, J=8.4, 2.2 Hz), 7.16 (d, 1H, J=2.2 Hz), 2.59 (s, 3H), 2.56 (s, 3H).

Step B. 1-(3-Methyl-4'-trifluoromethyl-biphenyl-4-yl)-ethanone

To an ambient temperature solution of trifluoro-methanesulfonic acid 4-acetyl-3-methyl-phenyl ester (6.10 g, 21.61 mmol) in dioxane/water (150/30 mL) is added 4-(trifluoromethyl)phenylboronic acid (4.51 g, 23.77 mmol), potassium carbonate (4.48 g, 32.42 mmol) and the reaction mixture is degassed with nitrogen for 20 min. Tetrakis(triphenylphosphine)palladium (1.25 g, 1.08 mmol) is added and the reaction mixture is heated to 80° C. overnight. TLC (10% EtOAc/hexane) indicates complete consumption of starting material. The reaction mixture is concentrated and chromatographed (330 g SiO$_2$, 5% EtOAc/Hexanes) to yield the title compound (5.77 g, 96%). $^1$NMR (400 MHz, CDCl$_3$) δ ppm: 7.82 (d, 1H, J=7.9 Hz), 7.72 (s, 4H), 7.51-7.46 (m, 2H), 2.63 (s, 3H), 2.62 (s, 3H).

Step C. (R,S)-1-(3-Methyl-4'-trifluoromethyl-biphenyl-4-yl)-ethanol

To a 0° C. solution of 1-(3-methyl-4'-trifluoromethyl-biphenyl-4-yl)-ethanone (1.0 g, 3.59 mmol) in THF/MeOH (27/8 ml) is added portion-wise sodium borohydride (272 mg, 7.18 mmol) and warmed to room temperature. After 1 h TLC (20% EtOAc/hexane) indicates complete consumption of starting material. The reaction mixture is concentrated and the residue is partitioned between EtOAc (100 mL) and 0.2N HCl (20 mL). The aqueous layer is extracted with a second portion of EtOAc (50 mL). The combined organic layers are washed with brine, dried (MgSO$_4$), filtered and concentrated to yield the title compound (993 mg, 98%). $^1$NMR (400 MHz, CDCl$_3$) δ ppm: 7.68 (s, 4H), 7.63 (d, 1H, J=8.4 Hz), 7.47 (d, 1H, J=8.4 Hz), 7.37 (s, 1H), 5.19 (q, 1H, J=6.5 Hz), 2.43 (s, 3H), 1.51 (d, 3H, J=6.2 Hz).

Preparation 4

(R,S)-1-(3-Fluoro-4'-trifluoromethyl-biphenyl-4-yl)-ethanol

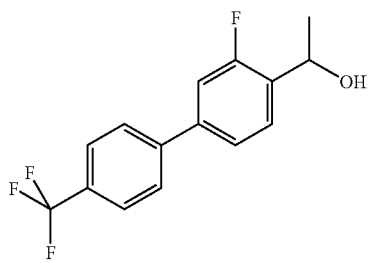

Step A. 3-Fluoro-4'-trifluoromethyl-biphenyl-4-carbaldehyde

To an ambient temperature solution of 4-(trifluoromethyl)phenylboronic acid (5.05 g, 26.59 mmol) in dioxane/water (15/15 mL) is added 4-bromo-2-fluoro-benzaldehyde (4.91 g, 24.17 mmol), tetrabutylammonium bromide (7.79 g, 24.17 mmol), potassium carbonate (9.18 g, 66.48 mmol) and is degassed for 10 min. Palladium(II) acetate (895 mg, 1.33 mmol) is added and the reaction mixture is heated to 70° C. After 2 h TLC (20% EtOAc/hexane) indicates complete consumption of starting material. The reaction is cooled to room temperature diluted with water and extracted with EtOAc (3×200 mL). The combined organic extracts are washed with brine, dried (MgSO$_4$), filtered, concentrated and chromatographed (330 g SiO$_2$, 5% EtOAc/Hexanes) to yield the title compound (5.57 g, 86%). $^1$NMR (400 MHz, CDCl$_3$) δ ppm: 10.41 (s, 1H), 7.98 (t, 1H, J=7.5 Hz), 7.74 (q, 4H, J=7.8 Hz), 7.52 (d, 1H, J=7.9 Hz), 7.41 (dd, 1H, J=11.2, 1.2 Hz).

Step B. (R,S)-1-(3-Fluoro-4'-trifluoromethyl-biphenyl-4-yl)-ethanol

To a −78° C. solution of 3-fluoro-4'-trifluoromethyl-biphenyl-4-carbaldehyde (600 mg, 2.24 mmol) in THF (25 mL) is added methylmagnesium bromide (1.5 mL, 4.48 mmol, 3.0M in Et$_2$O) dropwise. Upon complete addition the reaction mixture is warmed to room temperature. After 1 h at room temperature TLC (20% EtOAc/hexane) indicates complete consumption of starting material. The reaction is quenched with saturated aqueous NH₄Cl and concentrated. The residue is partitioned between EtOAc (100 mL) and 1N HCl (20 mL). The aqueous layer is extracted with EtOAc (100 mL) and the combined organic extracts are washed with water, brine, dried (MgSO₄), filtered and concentrated to yield the title compound (621 mg, 97%). ¹NMR (400 MHz, CDCl₃) δ ppm: 7.68 (q, 4H, J=7.9 Hz), 7.60 (t, 1H, J=7.7 Hz), 7.40 (dd, 1H, J=8.1, 1.5 Hz), 7.28 (d, 1H, J=1.3 Hz), 5.26 (q, 1H, J=6.6 Hz), 1.56 (d, 3H, J=6.2 Hz).

Preparation 5

(R,S)-1-(4'-Trifluoromethyl-biphenyl-4-yl)-ethanol

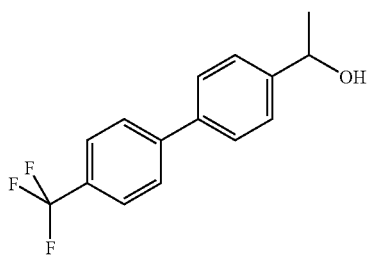

Step A. 4'-Trifluoromethyl-biphenyl-4-carbaldehyde

To an ambient temperature solution of 4-(trifluoromethyl) phenylboronic acid (4.64 g, 24.43 mmol) in dioxane/water (15/15 mL) is added 4-bromo-benzaldehyde (4.42 g, 22.21 mmol), tetrabutylammonium bromide (7.16 g, 22.21 mmol), potassium carbonate (7.67 g, 55.53 mmol) and is degassed for 10 min. Palladium(II) acetate (748 mg, 1.11 mmol) is added and the reaction mixture is heated to 70° C. After 2 h TLC (20% EtOAc/hexane) indicates complete consumption of starting material. The reaction is cooled to room temperature diluted with water and extracted with EtOAc (3×200 mL). The combined organic extracts are washed with brine, dried (MgSO₄), filtered, concentrated and chromatographed (330 g SiO₂, 5% EtOAc/Hexanes) to yield the title compound (5.54 g, 94%). ¹NMR (400 MHz, CDCl₃) δ ppm: 10.09 (s, 1H), 8.01-8.00 (m, 1H), 7.99-7.98 (m, 1H), 7.78-7.75 (m, 2H), 7.74 (s, 4H).

Step B. (R,S)-1-(4'-Trifluoromethyl-biphenyl-4-yl)-ethanol

To a −78° C. solution of 4'-trifluoromethyl-biphenyl-4-carbaldehyde (600 mg, 2.40 mmol) in THF (25 mL) is added methylmagnesium bromide (1.6 mL, 4.8 mmol, 3.0M in Et₂O) dropwise. Upon complete addition the reaction mixture is warmed to room temperature. After 1 h at room temperature TLC (20% EtOAc/hexane) indicates complete consumption of starting material. The reaction is quenched with saturated aqueous NH₄Cl and concentrated. The residue is partitioned between EtOAc (100 mL) and 1N HCl (20 mL). The aqueous layer is extracted with EtOAc (100 mL) and the combined organic extracts are washed with water (50 mL), brine, dried (MgSO₄), filtered, and concentrated yielding the title compound (642 mg, quant.). ¹NMR (400 MHz, CDCl₃) δ ppm: 7.69 (s, 4H), 7.59 (d, 2H, J=8.4 Hz), 7.49 (d, 2H, J=8.4 Hz), 4.98 (q, 1H, J=6.5 Hz), 1.55 (d, 3H, J=6.2 Hz).

Preparation 6

(R,S)-Methanesulfonic acid 2-(3-methyl-4'-trifluoromethyl-biphenyl-4-yl)-propyl ester

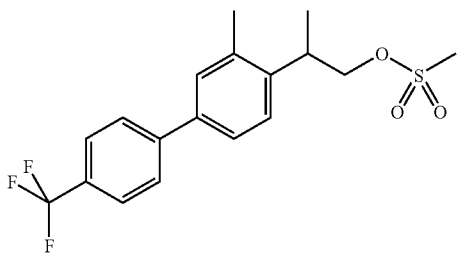

Step A. 4-(2-Methoxy-1-methyl-vinyl)-3-methyl-4'-trifluoromethyl-biphenyl

To a an ambient temperature suspension of potassium tert-butoxide (2.42 g, 21.56 mmol) in THF (70 mL) is added (methoxymethyl)triphenylphosphonium chloride (7.39 g, 21.56 mmol) and is stirred at room temperature for 30 min. 1-(3-methyl-4'-trifluoromethyl-biphenyl-4-yl)-ethanone (2.0 g, 7.19 mmol) is added and the reaction mixture continues to stir at room temperature. After 2 h TLC (20% EtOAc/hexane) indicates complete consumption of starting material. The reaction is quenched with saturated aqueous NH₄Cl and concentrated. The residue is partitioned between EtOAc (100 mL) and water (30 mL). The aqueous layer is extracted with EtOAc (100 mL) and The combined organic layers are washed with brine, dried (MgSO₄), filtered, concentrated and chromatographed (120 g SiO₂, 10% EtOAc/Hexanes) to yield the title compound (2.22 g, quant.).

Step B. (R,S)-2-(3-Methyl-4'-trifluoromethyl-biphenyl-4-yl)-propionaldehyde

To a 0° C. solution of 4-(2-methoxy-1-methyl-vinyl)-3-methyl-4'-trifluoromethyl-biphenyl (2.20 g, 7.18 mmol) in THF (25 mL) is added dropwise concentrated hydrochloric acid (12.75 mL) and the reaction is warmed to room temperature. After 1 h TLC (20% EtOAc/hexane) indicates complete consumption of starting material. The reaction mixture was diluted with water and the pH is adjusted to 8 with solid NaHCO₃. The reaction mixture is concentrated and the aqueous layer extracted with EtOAC (3×100 mL). The combined organic layers are washed with brine, dried (MgSO₄), filtered, concentrated and chromatographed (120 g SiO₂, 10% EtOAc/Hexanes) to yield the title compound (2.12 g, quant.). ¹NMR (400 MHz, CDCl₃) δ ppm: 9.70 (d, 1H, J=1.3 Hz), 7.68 (s, 4H), 7.49-7.43 (m, 2H), 7.16 (d, 1H, J=7.9 Hz), 3.90 (q, 1H, J=7.0 Hz), 2.44 (s, 3H), 1.47 (d, 3H, J=7.0 Hz).

Step C. (R,S)-2-(3-Methyl-4'-trifluoromethyl-biphenyl-4-yl)-propan-1-ol

To a 0° C. solution of 2-(3-methyl-4'-trifluoromethyl-biphenyl-4-yl)-propionaldehyde (2.10 g, 7.18 mmol) in THF/MeOH (55/15 mL) is added portion-wise sodium borohydride (544 mg, 14.37 mmol) and warmed to room temperature. After 1 h TLC (20% EtOAc/hexane) indicates complete consumption of starting material. The reaction mixture is concentrated and the residue is partitioned between EtOAc (100 mL) and 0.2N HCl (20 mL). The aqueous layer is extracted with a second portion of EtOAc (50 mL). The combined organic layers are washed with brine, dried (MgSO$_4$), filtered and concentrated to yield the title compound (1.91 g, 91%). $^1$NMR (400 MHz, CDCl$_3$) δ ppm: 7.67 (s, 4H), 7.44 (d, 1H, J=8.4 Hz), 7.42 (s, 1H), 7.32 (d, 1H, J=7.9 Hz), 3.84-3.72 (m, 2H), 3.37-3.26 (m, 1H), 2.45 (s, 3H), 1.29 (d, 3H, J=6.6 Hz).

Step D. (R,S)-Methanesulfonic acid 2-(3-methyl-4'-trifluoromethyl-biphenyl-4-yl)-propyl ester To a 0° C. solution of 2-(3-methyl-4'-trifluoromethyl-biphenyl-4-yl)-propan-1-ol (300 mg, 1.02 mmol) in CH$_2$Cl$_2$ (10 mL) is added methanesulfonyl chloride (95 μl, 1.22 mmol) and triethylamine (212 μl, 1.53 mmol) and warmed to room temperature overnight. TLC (20% EtOAc/hexane) indicates complete consumption of starting material. The reaction is quenched with saturated aqueous NH$_4$Cl and concentrated. The residue is partitioned between EtOAc (50 mL) and water (10 mL). The aqueous layer is extracted with EtOAc (50 mL) and the combined organic layers are washed with brine, dried (MgSO$_4$), filtered and concentrated to yield the title compound (388 mg, quant.).

$^1$NMR (400 MHz, CDCl$_3$) δ ppm: 7.68 (s, 4H), 7.44 (d, 1H, J=7.9 Hz), 7.42 (s, 1H), 7.31 (d, 1H, J=7.9 Hz), 4.35 (dd, 1H, J=9.9, 6.4 Hz), 4.25 (dd, 1H, J=9.9, 7.7 Hz), 3.57-3.46 (m, 1H), 2.90 (s, 3H), 2.45 (s, 3H), 1.39 (d, 3H, J=7.0 Hz).

Preparation 7

(R,S)-1-(4'-Trifluoromethyl-biphenyl-3-yl)-ethanol

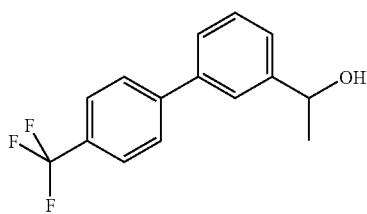

Step A. 4'-Trifluoromethyl-biphenyl-3-carbaldehyde

The titled compound was prepared from 3-bromo-benzaldehyde and trifluoromethyl-phenylboronic acid using standard Suzuki coupling condition in 84% yield.

Step B. (R,S)-1-(4'-Trifluoromethyl-biphenyl-3-yl)-ethanol

To a solution of (R,S)-4'-trifluoromethyl-biphenyl-3-carbaldehyde (500 mg, 2 mmol) in THF (10 mL) at 0° C. was added methyl magnesium bromide (3M, 1.3 mL). After stirring at room temperature for 3 hours, it was quenched with saturated ammonium chloride, extracted with EtOAc. The organic was concentrated to give the titled compound as an oil: 520 mg (quant.) $^1$NMR (400 MHz, CDCl$_3$) δ ppm: 7.40, 7.70 (m, 8H), 4.99 (q, 1H), 1.56 (d, 3H).

Preparation 8

(3-Methyl-4'-trifluoromethyl-biphenyl-4-yl)-methanol

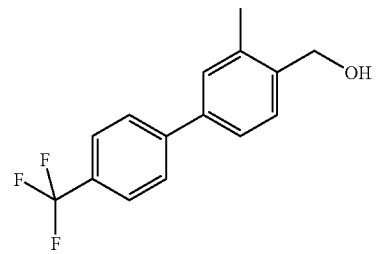

To a 0° C. solution of 3-methyl-4'-trifluoromethyl-biphenyl-4-carboxylic acid methyl ester (300 mg, 1.02 mmol) in THF/MeOH (10/3 mL) is added portion-wise sodium borohydride (386 mg, 10.20 mmol) and heated to reflux. After 1 h TLC (20% EtOAc/hexane) indicates complete consumption of starting material. The reaction mixture is concentrated and the residue is partitioned between EtOAc (100 mL) and 0.2N HCl (20 mL). The aqueous layer is extracted with a second portion of EtOAc (50 mL). The combined organic layers are washed with brine, dried (MgSO$_4$), filtered and concentrated to yield the title compound (268 mg, 99%). $^1$NMR (400 MHz, CDCl$_3$) δ ppm: 7.69 (s, 4H), 7.50-7.39 (m, 3H), 4.77 (s, 2H), 2.44 (s, 3H).

Preparation 9

2-(3-Fluoro-4'-trifluoromethyl-biphenyl-4-yl)-ethanol

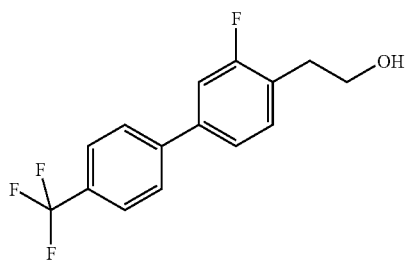

Step A. 3-Fluoro-4-(2-methoxy-vinyl)-4'-trifluoromethyl-biphenyl

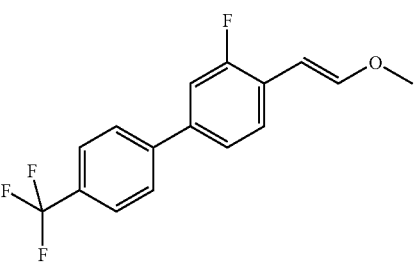

To a an ambient temperature suspension of potassium tert-butoxide (419 mg, 3.73 mmol) in THF (20 mL) is added (methoxymethyl)triphenylphosphonium chloride (1.28 g, 3.73 mmol) and is stirred at room temperature for 30 min. 3-Fluoro-4'-trifluoromethyl-biphenyl-4-carbaldehyde (500 mg, 1.87 mmol) is added and the reaction mixture continues to stir at room temperature. After 2 h TLC (30% EtOAc/hexane) indicates complete consumption of starting material. The reaction is quenched with saturated aqueous $NH_4Cl$ and concentrated. The residue is partitioned between EtOAc (50 mL) and water (20 mL). The aqueous layer is extracted with EtOAc (50 mL) and the combined organic layers are washed with brine, dried ($MgSO_4$), filtered, concentrated and chromatographed (120 g $SiO_2$, 5% EtOAc/Hexanes) to yield the title compound (474 mg, 85%).

Step B. (3-Fluoro-4'-trifluoromethyl-biphenyl-4-yl)-acetaldehyde

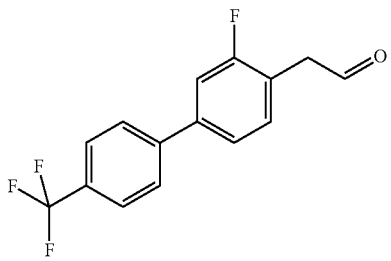

To a 0° C. solution of 3-fluoro-4-(2-methoxy-vinyl)-4'-trifluoromethyl-biphenyl (458 mg, 1.54 mmol) in THF (15 mL) is added dropwise concentrated hydrochloric acid (2.75 mL) and the reaction is warmed to room temperature. After 1 h TLC (30% EtOAc/hexane) indicates complete consumption of starting material. The reaction mixture was diluted with water and the pH is adjusted to 8 with solid $NaHCO_3$. The reaction mixture is concentrated and the aqueous layer extracted with EtOAc (3×50 mL). The combined organic layers are washed with brine, dried ($MgSO_4$), filtered, concentrated and chromatographed (40 g $SiO_2$, 5% EtOAc/Hexanes) to yield the title compound (388 mg, 89%). $^1$NMR (400 MHz, $CDCl_3$) δ ppm: 9.82 (s, 1H), 7.69 (q, 4H, J=8.4 Hz), 7.39 (dd, 1H, J=7.9, 1.3 Hz), 7.35 (dd, 1H, J=10.4, 1.5 Hz), 7.30 (t, 1H, J=7.7 Hz), 3.82 (s, 2H).

Step C. 2-(3-Fluoro-4'-trifluoromethyl-biphenyl-4-yl)-ethanol

To a 0° C. solution of (3-fluoro-4'-trifluoromethyl-biphenyl-4-yl)-acetaldehyde (372 mg, 1.31 mmol) in THF/MeOH (10/3 mL) is added portion-wise sodium borohydride (100 mg, 2.62 mmol) and warmed to room temperature. After 1 h TLC (30% EtOAc/hexane) indicates complete consumption of starting material. The reaction mixture is concentrated and the residue is partitioned between EtOAc (100 mL) and 0.2N HCl (20 mL). The aqueous layer is extracted with a second portion of EtOAc (50 mL). The combined organic layers are washed with brine, dried ($MgSO_4$), filtered and concentrated to yield the title compound (374 mg, quant.). $^1$NMR (400 MHz, $CDCl_3$) δ ppm: 7.68 (q, 4H, J=8.2 Hz), 7.38-7.32 (m, 2H), 7.29 (d, 1H, J=11.0 Hz), 3.92 (t, 2H, J=6.6 Hz), 2.97 (t, 2H, J=6.6 Hz).

Preparation 10

2-(4'-Trifluoromethyl-biphenyl-4-yl)-ethanol

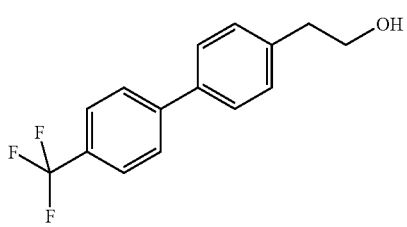

Step A. 4-(2-Methoxy-vinyl)-4'-trifluoromethyl-biphenyl

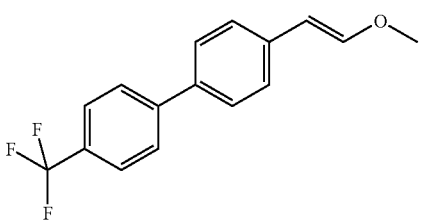

To an ambient temperature suspension of potassium tert-butoxide (449 mg, 4.00 mmol) in THF (20 mL) is added (methoxymethyl)triphenylphosphonium chloride (1.37 g, 4.00 mmol) and is stirred at room temperature for 30 min. 4'-trifluoromethyl-biphenyl-4-carbaldehyde (500 mg, 2.00 mmol) is added and the reaction mixture continues to stir at room temperature. After 2 h TLC (30% EtOAc/hexane) indicates complete consumption of starting material. The reaction is quenched with saturated aqueous $NH_4Cl$ and concentrated. The residue is partitioned between EtOAc (50 mL) and water (20 mL). The aqueous layer is extracted with EtOAc (50 mL) and the combined organic layers are washed with brine (100 mL), dried ($MgSO_4$), filtered, concentrated and chromatographed (40 g $SiO_2$, 5% EtOAc/Hexanes) to yield the title compound (482 mg, 87%).

Step B. (4'-Trifluoromethyl-biphenyl-4-yl)-acetaldehyde

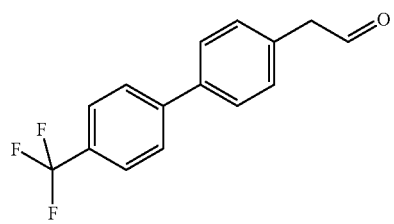

To a 0° C. solution of 4'-(2-methoxy-vinyl)-4-trifluoromethyl-biphenyl (464 mg, 1.67 mmol) in THF (17 mL) is added dropwise concentrated hydrochloric acid (2.98 mL) and the reaction is warmed to room temperature. After 1 h TLC (30% EtOAc/hexane) indicates complete consumption of starting material. The reaction mixture is diluted with water and the pH is adjusted to 8 with solid NaHCO₃. The reaction mixture is concentrated and the aqueous layer extracted with EtOAc (3×50 mL). The combined organic layers are washed with brine, dried (MgSO₄), filtered, concentrated and chromatographed (40 g SiO₂, 5% EtOAc/Hexanes) to yield the title compound (424 mg, 96%). $^1$NMR (400 MHz, CDCl₃) δ ppm: 9.81 (t, 1H, J=2.2 Hz), 7.69 (s, 4H), 7.61 (d, 2H, J=8.4 Hz), 7.33 (d, 2H, J=8.4 Hz), 3.78 (d, 2H, J=1.8 Hz).

Step C. 2-(4'-Trifluoromethyl-biphenyl-4-yl)-ethanol

To a 0° C. solution of (3-fluoro-4'-trifluoromethyl-biphenyl-4-yl)-acetaldehyde (372 mg, 1.31 mmol) in THF/MeOH (10/3 mL) is added portion-wise sodium borohydride (100 mg, 2.62 mmol) and warmed to room temperature. After 1 h TLC (30% EtOAc/hexane) indicates complete consumption of starting material. The reaction mixture is concentrated and the residue is partitioned between EtOAc (100 mL) and 0.2N HCl (20 mL). The aqueous layer is extracted with a second portion of EtOAc (50 mL). The combined organic layers are washed with brine, dried (MgSO₄), filtered and concentrated to yield the title compound (374 mg, quant.). $^1$NMR (400 MHz, CDCl₃) δ ppm: 7.68 (s, 4H), 7.56 (d, 2H, J=7.9 Hz), 7.35 (d, 2H, J=7.9 Hz), 3.92 (t, 2H, J=6.4 Hz), 2.94 (t, 2H, J=6.6 Hz).

Preparation 11

(4'-Trifluoromethyl-biphenyl-3-yl)-methanol

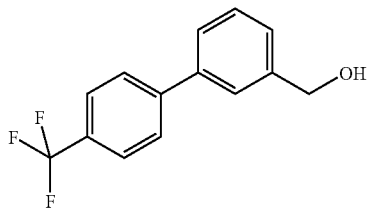

The titled compound was prepared by standard NaBH₄ reduction of 4'-trifluoromethyl-biphenyl-3-carbaldehyde (quant.). $^1$NMR (400 MHz, CDCl₃) δ ppm: 7.40, 7.70 (m, 8H), 4.79 (s, 2H).

Preparation 12

[6-(4-Trifluoromethyl-phenyl)-pyridin-3-yl]-methanol

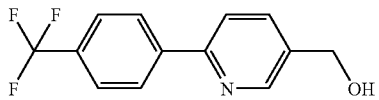

Step A. 6-(4-Trifluoromethyl-phenyl)-nicotinic acid methyl ester

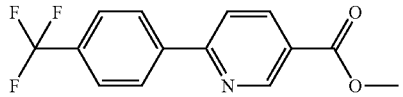

To an ambient temperature solution of 6-chloro-nicotinic acid methyl ester (12.4 g, 72 mmol) and 4-(trifluoromethyl) phenylboronic acid (15 g, 79 mmol) in dioxane (270 mL) is added CsF (38.3 g, 252 mmol) and the reaction mixture is degassed with nitrogen. PdCl₂(dppf) (1.5 g) is added and the reaction mixture is heated to 100° C. over weekend. The reaction mixture was diluted with ethyl acetate, filtered through celite. The filtrate is concentrated. Purification of the crude product by column on silica gel (hexanes/ethyl acetate) gives 6-(4-trifluoromethyl-phenyl)-nicotinic acid methyl ester (18.3 g, 82.3% yield).

Step B. [6-(4-Trifluoromethyl-phenyl)-pyridin-3-yl]-methanol

To a solution of 6-(4-trifluoromethyl-phenyl)-nicotinic acid methyl ester (13.7 g, 48.7 mmol) in THF (100 mL) is added LiAlH₄ (1.0 M in THF, 50 mL, 50 mmol) at 0~5° C., the reaction mixture is stirred for 2 hr, quenched by water and 5N NaOH (0.5 mL) carefully. The resulting mixture is diluted with ethyl acetate and filtered through celite. Concentration of the filtrate gives [6-(4-trifluoromethyl-phenyl)-pyridin-3-yl]-methanol (12.8 g).

Preparation 13

(R,S)-1-[6-(4-Trifluoromethyl-phenyl)-pyridin-3-yl]-propan-1-ol

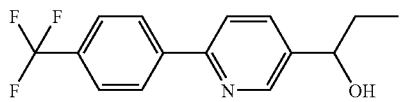

To a solution of 6-(4-trifluoromethyl-phenyl)-pyridine-3-carbaldehyde (2.1 g, 8.3 mmol) in THF (20 mL) is added EtMgBr (3.0 M in Et2O, 3.2 mL, 9.6 mmol) at 0~5° C., stirred for 2 hrs, quenched by NH₄Cl aq., extracted with ethyl acetate, dried and concentrated giving 1-[6-(4-trifluoromethyl-phenyl)-pyridin-3-yl]-propan-1-ol (1.8 g) and [6-(4-trifluoromethyl-phenyl)-pyridin-3-yl]-methanol (0.29 g).

The following compounds are made in a similar manner:

Preparation 14

(R,S)-1-[6-(4-Trifluoromethyl-phenyl)-pyridin-3-yl]-ethanol

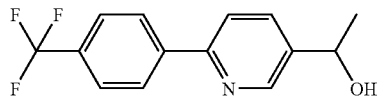

Preparation 15

(R,S)-1-[6-(4-Trifluoromethyl-phenyl)-pyridin-3-yl]-butan-1-ol

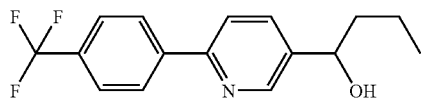

Preparation 16

(R,S)-1-[6-(4-Trifluoromethyl-phenyl)-pyridin-3-yl]-pentan-1-ol

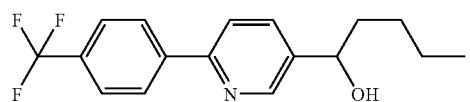

Preparation 17

(R,S)-1-[6-(4-Trifluoromethyl-phenyl)-pyridin-3-yl]-hexan-1-ol

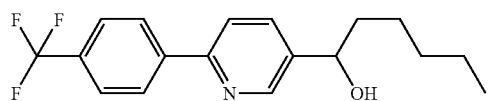

Preparation 18

(R,S)-1-[6-(4-Trifluoromethyl-phenyl)-pyridin-3-yl]-heptan-1-ol

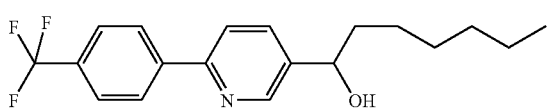

Preparation 19

(R,S)-2-Cyclohexyl-1-[6-(4-trifluoromethyl-phenyl)-pyridin-3-yl]-ethanol

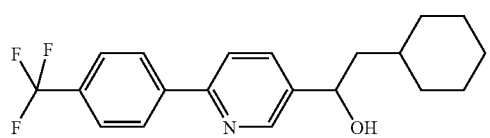

Preparation 20

(R,S)-4,4-Dimethyl-1-[6-(4-trifluoromethyl-phenyl)-pyridin-3-yl]-pentan-1-ol

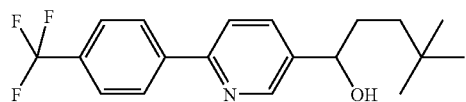

Preparation 21

(R,S)-3,3-Dimethyl-1-[6-(4-trifluoromethyl-phenyl)-pyridin-3-yl]-butan-1-ol

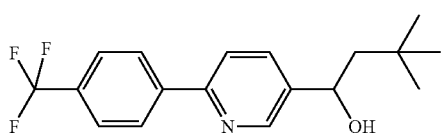

Preparation 22

(R,S)-(4-tert-Butyl-phenyl)-[6-(4-trifluoromethyl-phenyl)-pyridin-3-yl]-methanol

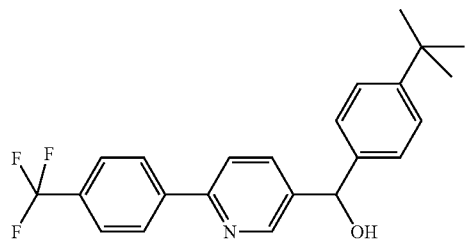

Preparation 23

(R,S)-4,4,4-Trifluoro-1-[6-(4-trifluoromethyl-phenyl)-pyridin-3-yl]-butan-1-ol

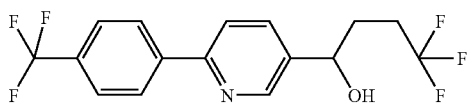

Preparation 24

(R,S)-5,5,5-Trifluoro-1-[6-(4-trifluoromethyl-phenyl)-pyridin-3-yl]-pentan-1-ol

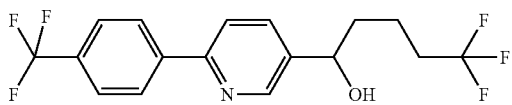

Preparation 25

3-Methyl-4'-trifluoromethyl-biphenyl-4-carbaldehyde

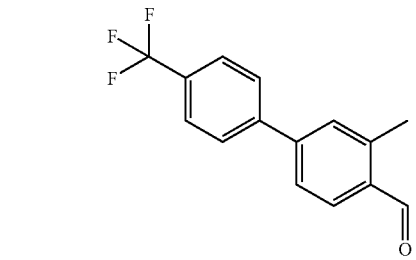

Step A. (3-Methyl-4'-trifluoromethyl-biphenyl-4-yl)-methanol

A solution of 3-methyl-4'-trifluoromethyl-biphenyl-4-carboxylic acid methyl ester (1.993 g, 6.773 mmol) in $CH_2Cl_2$ (34 mL) at 0° C. is treated with 1.0 M diisobutylaluminum hydride in toluene (DIBAL, 14.3 mL) dropwise over 3 min. time and stirred for 3.5 h. The reaction mixture is quenched with MeOH (5.0 mL), treated with 1M tartaric acid (50 mL), and stirred overnight. The organic layer is separated. The aqueous layer is extracted with $CH_2Cl_2$ (1×50 mL). Combined organic extracts are dried over $MgSO_4$, filtered, and conc. to provide (3-methyl-4'-trifluoromethyl-biphenyl-4-yl)-methanol (1.616 g, 90%) as a white solid.

Step B. 3-Methyl-4'-trifluoromethyl-biphenyl-4-carbaldehyde

A solution of (3-methyl-4'-trifluoromethyl-biphenyl-4-yl)-methanol (1.613 g, 6.060 mmol) in dimethylsulfoxide (DMSO, 12.0 mL) is treated with $Et_3N$ (5.50 mL, 39.460 mmol) and pyridine-sulfur trioxide (2.902 g, 18.235 mmol) in a cold water bath. The bath is removed after 3 min. and the reaction is stirred overnight. The reaction mixture is poured into $H_2O$ (50 mL) and extracted with EtOAc (3×50 mL). Combined organic extracts are dried over $MgSO_4$, filtered, and conc. The residue is loaded onto silica gel and eluted with hexanes using a gradient from 5% EtOAc to 33% EtOAc to provide 3-methyl-4'-trifluoromethyl-biphenyl-4-carbaldehyde (1.221 g, 76%) as white crystals.

Preparation 26

(R,S)-2-Cyclohexyl-1-(4'-trifluoromethyl-biphenyl-4-yl)-ethanol

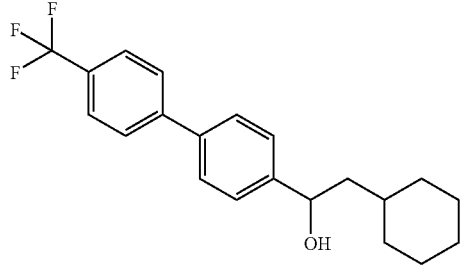

Step A. Cyclohexylmethyl-magnesium bromide

A suspension of magnesium turnings (1.828 g, 75.12 mmol) in THF (50 mL) is treated with iodine (0.304 g, 1.199 mmol) and warmed to reflux. A solution of bromomethylcyclohexane (7.0 mL, 50.2 mmol) in THF (10 mL) is added dropwise for 30 min. The reaction is heated at reflux for 3 h, then cooled to RT, and cannulated into an oven-dried round-bottom flask.

Step B. (R,S)-2-Cyclohexyl-1-(4'-trifluoromethyl-biphenyl-4-yl)-ethanol

A solution of 4'-trifluoromethyl-biphenyl-4-carbaldehyde (3.358 g, 13.42 mmol) in TBF (50 mL) at 0° C. is treated with cyclohexyl-magnesium bromide solution (27.0 mL) dropwise for 8 min. The reaction is stirred for 12 min., then quenched with saturated $NH_4Cl$ (50 mL). The reaction mixture is diluted with $H_2O$ and extracted with EtOAc (1×100 mL, 2×50 mL). Combined extracts are washed with brine (1×), dried over $MgSO_4$, filtered, and conc. The residue is loaded onto silica gel and eluted with hexanes using a gradient from 5% EtOAc to 33% EtOAc to provide (±)-2-Cyclohexyl-1-(4'-trifluoromethyl-biphenyl-4-yl)-ethanol (2.216 g, 47%) as a white solid.

The following compounds are made in a substantially similar manner:

Preparation 27

(R,S)-1-(3-Methyl-4'-trifluoromethylbiphenyl-4-yl)ethanol

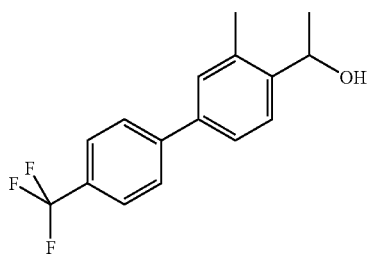

Preparation 28

(R,S)-1-(3-Methyl-4'-trifluoromethylbiphenyl-4-yl)butanol

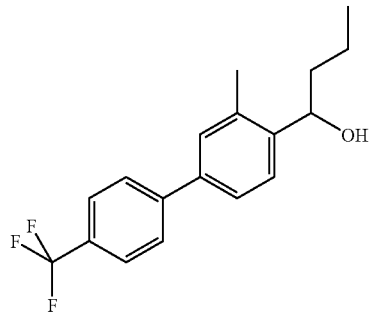

Preparation 29

(R,S)-2-Methyl-1-(3-methyl-4'-trifluoromethylbiphenyl-4-yl)propan-1-ol

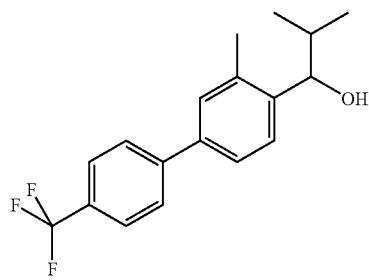

Preparation 30

(R,S)-3-Methyl-1-(3-methyl-4'-trifluoromethylbiphenyl-4-yl)butan-1-ol

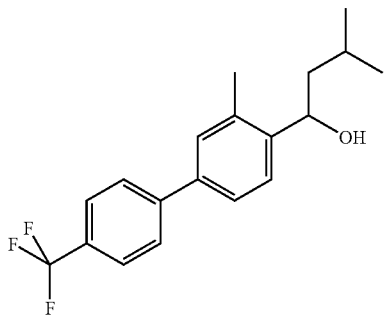

Preparation 31

(R,S)-1-(4'-Trifluoromethyl-biphenyl-4-yl)-ethanol

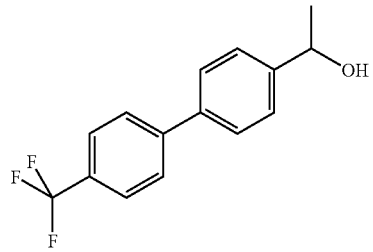

Step A. 4'-Trifluoromethyl-biphenyl-4-carbaldehyde

To an ambient temperature solution of 4-(trifluoromethyl)phenylboronic acid (4.64 g, 24.43 mmol) in dioxane/water (15/15 mL) is added 4-bromo-benzaldehyde (4.42 g, 22.21 mmol), tetrabutylammonium bromide (7.16 g, 22.21 mmol), potassium carbonate (7.67 g, 55.53 mmol) and degassed for 10 min. Palladium(II) acetate (748 mg, 1.11 mmol) is added and the reaction mixture is heated to 70° C. After 2 h TLC (20% EtOAc/hexane) indicates complete consumption of starting material. The reaction is cooled to room temperature diluted with water and extracted with EtOAc (3×200 mL). The combined organic extracts are washed with brine, dried (MgSO$_4$), filtered, concentrated and chromatographed (330 g SiO$_2$, 5% EtOAc/Hexanes) to yield the title compound (5.54 g, 94%). $^1$NMR (400 MHz, CDCl$_3$) δppm: 10.09 (s, 1H), 8.01-8.00 (m, 1H), 7.99-7.98 (m, 1H), 7.78-7.75 (m, 2H), 7.74 (s, 4H).

Step B. (R,S)-1-(4'-Trifluoromethyl-biphenyl-4-yl)-ethanol

To a −78° C. solution of 4'-trifluoromethyl-biphenyl-4-carbaldehyde (600 mg, 2.40 mmol) in THF (25 mL) is added methylmagnesium bromide (1.6 mL, 4.8 mmol, 3.0M in Et$_2$O) dropwise. Upon complete addition the reaction mixture is warmed to room temperature. After 1 h at room temperature TLC (20% EtOAc/hexane) indicates complete consumption of starting material. The reaction is quenched with saturated aqueous NH$_4$Cl and concentrated. The residue is partitioned between EtOAc (100 mL) and 1N HCl (20 mL). The aqueous layer is extracted with EtOAc (100 mL) and the combined organic extracts are washed with water (50 mL), brine, dried (MgSO$_4$), filtered, and concentrated yielding the title compound (642 mg, quant.). $^1$NMR (400 MHz, CDCl$_3$) δ ppm: 7.69 (s, 4H), 7.59 (d, 2H, J=8.4 Hz), 7.49 (d, 2H, J=8.4 Hz), 4.98 (q, 1H, J=6.5 Hz), 1.55 (d, 3H, J=6.2 Hz).

The following compounds are made in a substantially similar manner:

Preparation 32

(R,S)-1-(4'-Trifluoromethylbiphenyl-4-yl)propanol

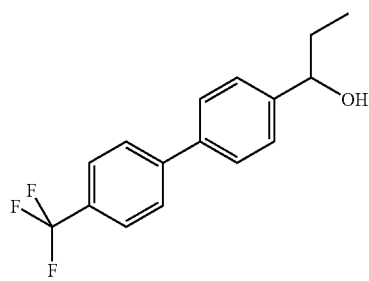

Preparation 33

(R,S)-1-(4'-Trifluoromethylbiphenyl-4-yl)butanol

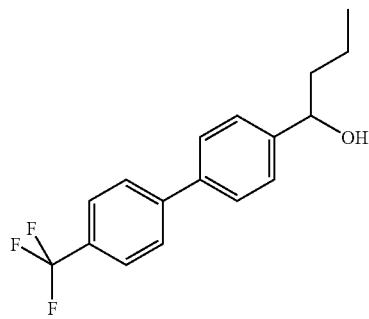

Preparation 34

(R,S)-1-(4'-Trifluoromethylbiphenyl-4-yl)pentanol

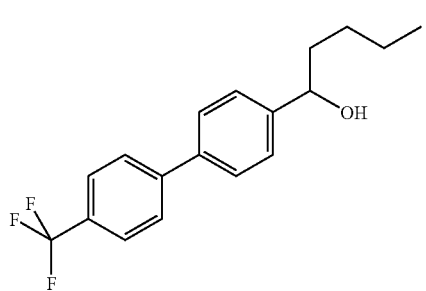

Preparation 35

(R,S)-1-(4'-Trifluoromethylbiphenyl-4-yl)hexanol

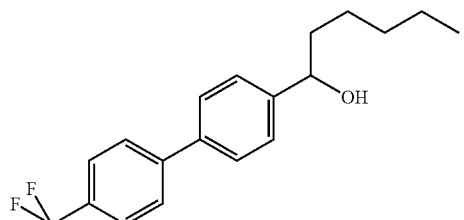

Preparation 36

(R,S)-1-(4'-Trifluoromethylbiphenyl-4-yl)heptanol

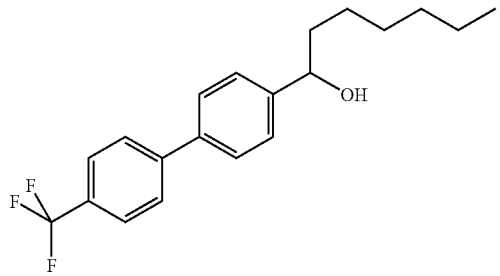

Preparation 37

(R,S)-2-Methyl-1-(4'-trifluoromethylbiphenyl-4-yl)propan-1-ol

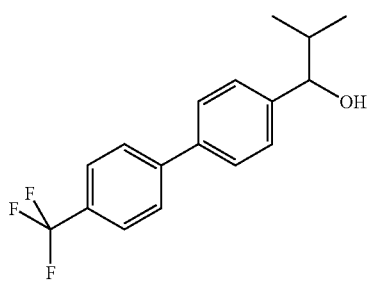

Preparation 38

(R,S)-3-Methyl-1-(4'-trifluoromethylbiphenyl-4-yl)butan-1-ol

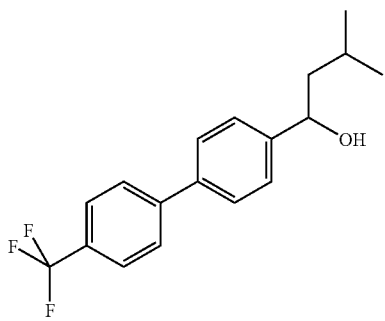

Preparation 39

(R,S)-1-(4'-Trifluoromethylbiphenyl-4-yl)undecan-1-ol

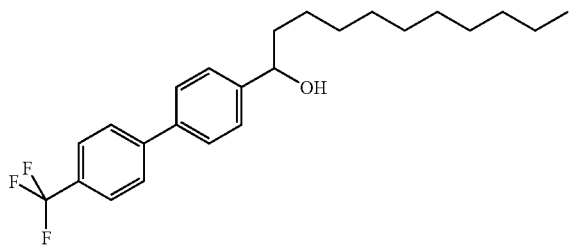

Preparation 40

(R,S)-Phenyl(4'-trifluoromethylbiphenyl-4-yl)methanol

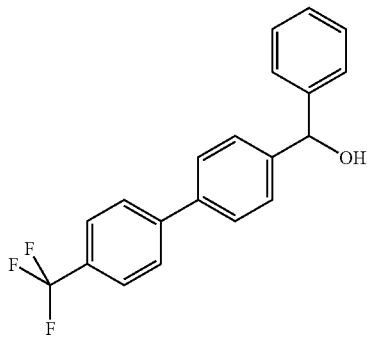

Preparation 41

(R,S)-2-Cyclohexyl-1-(2'-trifluoromethylbiphenyl-4-yl)ethanol

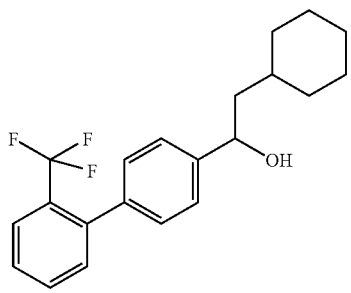

Step A. 2'-Trifluoromethylbiphenyl-4-carbaldehyde

To a solution of 4-bromobenzaldehyde (1 g, 5.40 mmol) in THF (21.6 mL) is added (2-trifluoromethyl)phenylboronic acid (1.67 g, 8.1 mmol), potassium fluoride (780 mg, 16.2 mmol), palladium(II) acetate (12.1 mg, 0.054 mmol), and 2-(dicyclohexylphosphino)-biphenyl (37.9 mg, 0.108 mmol). The reaction mixture is heated to reflux overnight. After cooling to rt, the reaction mixture is partitioned between dichloromethane and water. The aqueous layer is back-extracted with dichloromethane, the combined organic layers are dried and concentrated, then loaded onto silica gel and eluted using hexanes with an ethyl acetate gradient from 0% to 60% giving 2'-trifluoromethylbiphenyl-4-carbaldehyde (1.0548 g).

Step B. (R,S)-2-Cyclohexyl-1-(2'-trifluoromethylbiphenyl-4-yl)ethanol

A solution of 2'-trifluoromethylbiphenyl-4-carbaldehyde (311 mg, 1.24 mmol) in THF (8.7 mL) under nitrogen is cooled to 0° C., treated with (cyclohexyl)methyl-magnesium bromide (1.0 M in THF, 3.73 mL, 3.72 mmol), stirred at 0° C. for 3 h, then quenched with 1 N HCl. The reaction mixture is extracted with diethyl ether, dried and concentrated, then loaded onto silica gel and eluted using hexanes with an ethyl acetate gradient from 0% to 40% giving the title compound (252 mg).

The following compound is prepared in a substantially similar manner.

Preparation 42

(R,S)-2-Cyclohexyl-1-(3'-trifluoromethylbiphenyl-4-yl)ethanol

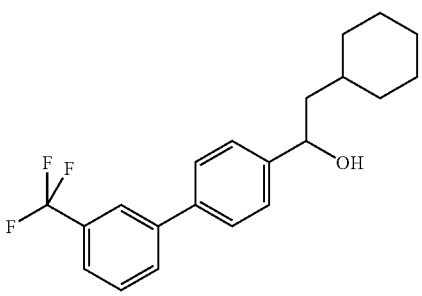

Preparation 43

(R,S)-2-(4'-Trifluoromethylbiphenyl-4-yl)butan-1-ol

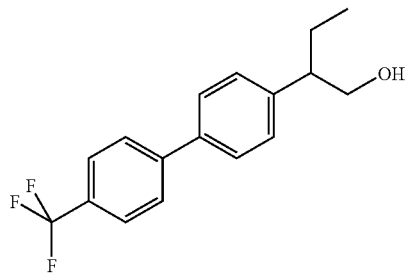

Step A. 1-(4'-Trifluoromethylbiphenyl-4-yl)propan-1-one

To a solution of 1-(4-bromophenyl)propan-1-one (10 g, 46.9 mmol) in toluene/ethanol (47/47 ml) is added 4-trifluoromethylphenylboronic acid (10.63 g, 51.6 mmol), tetrakis(triphenylphosphine)palladium (2.7 g, 2.3 mmol), and 2 N potassium carbonate (47 mL). The reaction mixture is heated at reflux overnight, cooled to rt, and partitioned between ethyl acetate and water. The organic layer is dried and concentrated, then loaded onto silica gel and eluted using hexanes with an ethyl acetate gradient from 0% to 60% giving 1-(4'-trifluoromethylbiphenyl-4-yl)propan-1-one (11.52 g).

Step B. 4-(1-Methoxymethylenepropyl)-4'-trifluoromethylbiphenyl

To a an ambient temperature suspension of potassium tert-butoxide (670 mg, 5.39 mmol) in toluene (36 mL) is added (methoxymethyl)triphenylphosphonium chloride (1.85 g, 5.56 mmol) and is stirred at room temperature for 30 min. 1-(4'-trifluoromethylbiphenyl-4-yl)-propan-1-one (1 g, 3.59 mmol) is added, and the reaction mixture continues to stir at room temperature overnight. The reaction mixture is filtered, using dichloromethane to aid rinsing, concentrated to ⅓ volume, then loaded onto silica gel and eluted using hexanes with an ethyl acetate gradient from 0% to 25% giving 4-(1-methoxymethylene-propyl)-4'-trifluoromethylbiphenyl (278 mg).

Step C. 2-(4'-Trifluoromethylbiphenyl-4-yl)butyraldehyde

A solution of 4-(1-methoxymethylenepropyl)-4'-trifluoromethylbiphenyl (278 mg, 0.908 mmol) in THF (9.1 mL) is treated with concentrated hydrochloric acid (0.456 mL), and the reaction is heated at reflux overnight. The reaction mixture is cooled to RT, and extracted with EtOAc (3×). The combined organic layers are dried and concentrated, giving 2-(4'-trifluoromethylbiphenyl-4-yl)butyraldehyde as a crude residue to be used as is (weight in excess of theoretical yield).

Step D. (R,S)-2-(4'-Trifluoromethylbiphenyl-4-yl)butan-1-ol

A 0° C. solution of 2-(4'-trifluoromethylbiphenyl-4-yl)butyraldehyde (0.908 mmol) in EtOH (9 mL) under nitrogen is treated with sodium borohydride (86 mg, 2.27 mmol), warmed to room temperature, and stirred overnight. The reaction mixture is quenched with 1 N HCl, extracted into dichloromethane (3×), dried and concentrated, then loaded onto silica gel and eluted using hexanes with an ethyl acetate gradient from 0% to 30% giving the title compound (80 mg).

Preparation 44

Bis-(4'-trifluoromethylbiphenyl-4-yl)methanol

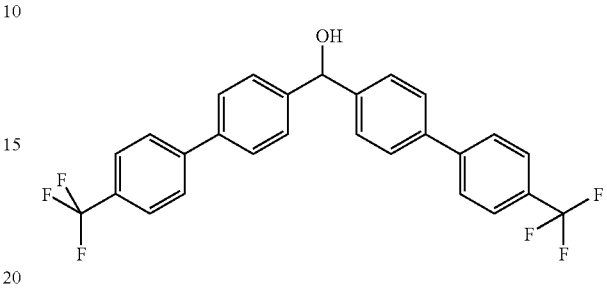

Step A. Bis-(4-bromophenyl)methanol

A solution of bis-(4-bromophenyl)methanone (406 mg, 1.19 mmol) in THF (12 mL) is cooled to 0° C., treated portion-wise with sodium borohydride (37.8 mg, 0.893 mmol), and stirred at RT overnight. The reaction mixture is again cooled to 0° C., then quenched with 1 N HCl. Water is added, and the mixture is extracted with ethyl acetate (3×). The combined organic layers are dried and concentrated to give bis-(4-bromophenyl)methanol (410 mg, in excess of theoretical yield) as a crude residue to be used as is.

Step B. Bis-(4'-trifluoromethylbiphenyl-4-yl)methanol

To a solution of bis-(4-bromophenyl)methanol (1.19 mmol) in THF (4.76 mL) is added (4-trifluoromethyl)phenylboronic acid (735 mg, 3.57 mmol), potassium fluoride (343 mg, 7.14 mmol), palladium(II) acetate (16 mg, 0.071 mmol), and 2-(Dicyclohexylphosphino)biphenyl (50 mg, 0.143 mmol). The reaction mixture is heated to reflux for 3.5 h, cooled to RT, and partitioned between ethyl acetate and water. The aqueous layer is back-extracted with ethyl acetate (3×), the combined organic layers are dried and concentrated, then loaded onto silica gel and eluted using hexanes with an ethyl acetate gradient from 0% to 70% giving the title compound (450 mg).

Preparation 45

Racemic 1-[4-(2,3,5,6-Tetramethyl-benzyloxy)-phenyl]-propan-1-ol

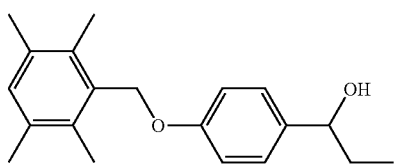

Step A. 1-[4-(2,3,5,6-Tetramethyl-benzyloxy)-phenyl]-propan-1-one

NaOH (1.6 g, 40 mmol) is added to the solution of 1-(4-hydroxy-phenyl)-propan-1-one (3.0 g, 20 mmol) in EtOH (50 mL) and water (30 mL), followed by the addition of 3-Chloromethyl-1,2,4,5-tetramethyl-benzene (5.5 g, 30 mol). The resulting mixture is heated to turn into clear solution and stirred at room temperature overnight. The reaction is quenched by 1N HCl and extracted with ethyl acetate (3×100 mL). The combined organic layers are washed with water, brine, dried (MgSO₄), concentrated and chromatographed to afford the titled compound as a white solid (4.0 g).

Step B. Racemic 1-[4-(2,3,5,6-Tetramethyl-benzyloxy)-phenyl]-propan-1-ol

NaBH₄ (616 mg, 16.2 mmol) is added to the solution of 1-[4-(2,3,5,6-Tetramethyl-benzyloxy)-phenyl]-propan-1-one (4.0 g, 13.5 mmol) in THF (30 mL) and EtOH (5 mL). After stirring for 2 h, the reaction is quenched by water and extracted with ethyl acetate. The solvent is removed to afford the titled compound as a white solid (4.0 g).

Preparation 46

(R,S)-1-(4-Pentamethylphenylmethoxy-phenyl)-propan-1-ol

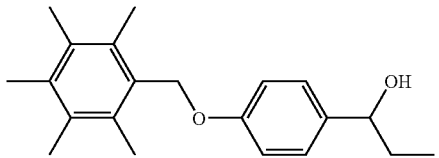

Step A.
1-(4-Pentamethylphenylmethoxy-phenyl)-propan-1-one

To a solution of Pentamethylphenyl-methanol (1000 mg, 5.6 mmol) in TBF (10 mL) is added 1,1'-(azodicarbonyl)dipiperidine (ADDP, 1690 mg, 1.75 mmol), followed by the addition of triphenylphosphine (1760 mg, 6.72 mmol) and 1-(4-hydroxy-phenyl)-propan-1-one (843 mg, 5.6 mmol). The reaction mixture is stirred at room temperature overnight. The mixture is loaded on silica gel, eluted with hexanes with a gradient from 0% of ethyl acetate to 50% of ethyl acetate giving 1-(4-pentamethylphenylmethoxy-phenyl)-propan-1-one as a white solid (480 mg).

Step B.
1-(4-Pentamethylphenylmethoxy-phenyl)-propan-1-ol 1-(4-Pentamethylphenylmethoxy-phenyl)-propan-1-one (480 mg, 1.54 mmol) is reduced by the standard NaBH4 type reduction to afford the titled compound (430 mg).

Preparation 47

(R,S)-4-[1-(4'-Trifluoromethylbiphenyl-4-yl)propoxy]benzoic acid

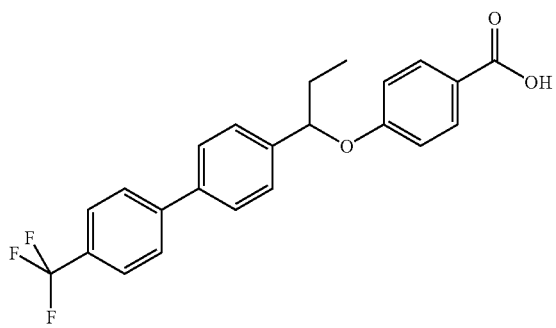

Step A. (R,S)-Methyl 4-[1-(4'-trifluoromethylbiphenyl-4-yl)propoxy]benzoate

To a solution of (R,S)-1-(4'-trifluoromethylbiphenyl-4-yl) propanol (3.1 g, 11.06 mmol) in toluene (111 mL) is added 1,1'-(azodicarbonyl)dipiperidine (ADDP, 4.2 g, 16.6 mmol), triphenylphosphine (4.4 g, 16.6 mmol) and methyl 4-hydroxybenzoate (1.68 g, 11.06 mmol). The reaction mixture is stirred for 60 h. The mixture is treated with water, extracted into ethyl acetate, dried and concentrated, then loaded onto silica gel and eluted with 15% ethyl acetate in hexanes (isocratic) giving (R,S)-methyl 4-[1-(4'-trifluoromethylbiphenyl-4-yl)propoxy]benzoate (1.78 g).

Step B. (R,S)-4-[1-(4'-Trifluoromethylbiphenyl-4-yl) propoxy]benzoic acid

A solution of methyl 4-[1-(4'-trifluoromethylbiphenyl-4-yl)propoxy]benzoate (1.733 g, 4.18 mmol) in methanol (42 mL) is treated with 5 N NaOH (4.18 mL) and heated at reflux overnight. The reaction is cooled to RT, neutralized with 1 N HCl (25 mL), and extracted into dichloromethane (3×). The combined organic layers are dried and concentrated, giving the title compound (1.49 g).

Preparation 48

(R,S)-4-[2-Cyclohexyl-1-(4'-trifluoromethyl-biphenyl-4-yl)-ethoxy]-benzoic acid

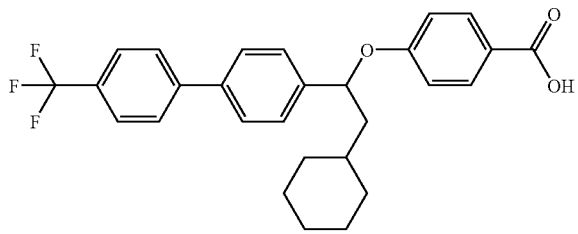

Step A. (R,S)-4-[2-cyclohexyl-1-(4'-trifluoromethyl-biphenyl-4-yl)-ethoxy]-benzoic acid methyl ester A solution of (R,S)-2-cyclohexyl-1-(4'-trifluoromethyl-biphenyl-4-yl)-ethanol (0.309 g, 0.886 mmol), 4-hydroxy-benzoic acid methyl ester (0.154 g, 1.01 mmol), and triphenylphosphine (0.339 g, 1.29 mmol) in toluene (9.0 mL) is treated with 1,1'-(azodicarbonyl)dipiperidine (ADDP, 0.336 g, 1.33 mmol) and stirred for 4 d. The reaction mixture is filtered through Celite® and concentrated. The residue is loaded onto silica gel and eluted with hexanes using a gradient of 10% EtOAc to 60% EtOAc giving (±)-4-[2-cyclohexyl-1-(4'-trifluoromethyl-biphenyl-4-yl)-ethoxy]-benzoic acid methyl ester (0.304 g, 71%) as a clear syrup.

Step B. (R,S)-4-[2-cyclohexyl-(4'-trifluoromethyl-biphenyl-4-yl)-ethoxy]-benzoic acid To a mixture of (R,S)-4-[2-cyclohexyl-1-(4'-trifluoromethyl-biphenyl-4-yl)-ethoxy]-benzoic acid methyl ester (0.304 g, 0.629 mmol) in THF (6.0 mL) is added LiOH (1 N aqueous, 6.0 mL) and stirred at 70° C. overnight. The reaction mixture is acidified with 1N HCl (7.0 mL) and extracted with EtOAc (3×20 mL). Combined organic extracts are dried over MgSO$_4$, filtered, and concentrated to provide (±)-4-[2-cyclohexyl-(4'-trifluoromethyl-biphenyl-4-yl)-ethoxy]-benzoic acid (0.261 g, 88%) as a white foam. MS (ES): 467.3 [M–H]$^-$.

Preparation 49

3-{4-[2-Cyclohexyl-1-(4'-trifluoromethyl-biphenyl-4-yl)-ethoxy]-benzoylamino}-propionic acid tert-butyl ester

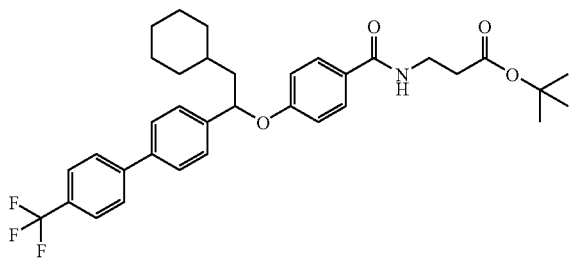

A solution of (R,S)-2-cyclohexyl-1-(4'-trifluoromethyl-biphenyl-4-yl)-ethanol (0.605 g, 1.737 mmol), 3-(4-hydroxybenzoylamino)-propionic acid tert-butyl ester (0.503 g, 1.895 mmol), and triphenylphosphine (0.692 g, 2.693 mmol) in toluene (17.0 mL) is treated with 1,1'-(azodicarbonyl)dipiperidine (ADDP, 0.634 g, 2.591 mmol) and stirred for 3 d The reaction mixture is filtered through Celite® and conc. The residue is loaded onto silica gel and eluted with hexanes using a gradient of 25% EtOAc to 100% EtOAc giving (±)-3-{4-[2-cyclohexyl-1-(4'-trifluoromethyl-biphenyl-4-yl)-ethoxy]-benzoylamino}-propionic acid tert-butyl ester (0.625 g, 60%) as a white foam. MS (ES): 596.4 [M+H]$^+$.

A portion of this material is resolved by chiral chromatography (Chiralpak AD-H (0.46×15 cm), 60% heptane: 40% isopropyl alcohol, 1.0 mL/min., 0.020 mL inj.) to provide Isomer 1 (0.120 g), Ret. Time=2.49 min. and Isomer 2 (0.105 g), Ret. Time=3.97 min.

Preparation 50

1-(2,6-Dimethyl-4'-trifluoromethyl-biphenyl-4-yl)-3-methyl-butan-1-ol

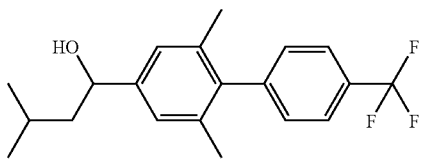

Step A. Trifluoro-methanesulfonic acid 4-formyl-2,6-dimethyl-phenyl ester

To a solution of 4-Hydroxy-3,5-dimethyl-benzaldehyde (4.5 g, 30 mmol) in pyridine (20 mL) at 0° C. was slowly added triflic anhydride (10 g, 36 mmol). The resulting mixture was stirred at 0° C. for 10 min and then allowed to warm to room temperature and stirred for 20 h. The resulting mixture was poured into water and extracted with ether, washed with water, 1N HCl, brine, dried over MgSO$_4$, concentrated and purified with column chromatography to afford 4.4 g (52%) of the titled compound as colorless oil.

Step B. 2,6-Dimethyl-4'-trifluoromethyl-biphenyl-4-carbaldehyde

Trifluoro-methanesulfonic acid 4-formyl-2,6-dimethyl-phenyl ester (4 g, 14.2 mmol), 4-trifluoromethyl-phenylboronic acid (5.4 g, 28.4 mmol),
tetrakis(triphenylphosphine)palladium (1.64 g, 1.42 mmol), LiCl (1.8 g, 42.6 mmol), and K$_2$CO$_3$ (5.9 g, 42.6 mmol) were placed in a flask. The system was purged with N$_2$, followed by the addition of toluene (20 mL) and H$_2$O (5 mL). The resulting mixture was refluxed over night, loaded on silica gel directly, and purified by column chromatography to afford 3.8 g (96%) of the titled compound as a white solid.

Step C. 1-(2,6-Dimethyl-4'-trifluoromethyl-biphenyl-4-yl)-3-methyl-butan-1-ol To a solution of 2,6-Dimethyl-4'-trifluoromethyl-biphenyl-4-carbaldehyde (1.0 g, 3.6 mmol) in THF (10 mL) at 0° C. is added isobutyl magnesium bromide (2M, 2.2 mL). After stirring at room temperature for 2 hours, it is quenched with saturated ammonium chloride, extracted with EtOAc. The organic is concentrated to give the titled compound as colorless oil: 0.47 g (39%).

Example 1

3-{4-[6-(4-Trifluoromethyl-phenyl)-pyridin-3-ylmethoxy]-benzoylamino}-propionic acid

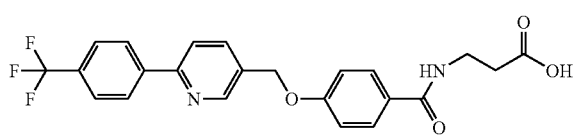

To a solution of [6-(4-trifluoromethyl-phenyl)-pyridin-3-yl]-methanol (120 mg, 0.47 mmol) in THF (2 mL) and toluene (4 mL) is added 1,1'-(azodicarbonyl)dipiperidine (ADDP, 179.5 mg, 0.71 mmol) at 0° C., followed by the addition of tributylphosphine (0.18 mL, 0.71 mmol) and 3-(4-hydroxybenzoylamino)-propionic acid methyl ester (127 mg, 0.57 mmol). The reaction mixture is warmed up to room temperature and stirred overnight. The mixture is loaded on silica gel, eluted with hexanes with a gradient from 0% of ethyl acetate to 50% of ethyl acetate giving 3-{4-[6-(4-trifluoromethyl-phenyl)-pyridin-3-ylmethoxy]-benzoylamino}-propionic acid methyl ester. The ester product is taken into ethanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving 3-{4-[6-(4-Trifluoromethyl-phenyl)-pyridin-3-ylmethoxy]-benzoylamino}-propionic acid (33 mg). MS (ES): 443.2 [M+H]⁻.

The following compounds are made in a manner substantially similar to Example 1.

Example 2

(R,S)-3-(4-{1-[6-(4-Trifluoromethyl-phenyl)-pyridin-3-yl]-ethoxy}-benzoylamino)-propionic acid

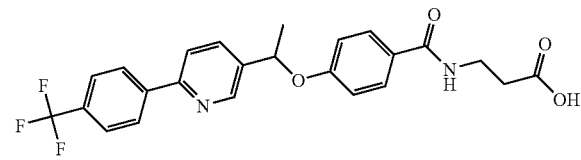

MS (ES): 457.2 [M+H]⁻.

Example 3

(R,S)-3-(4-{2-Cyclohexyl-1-[6-(4-trifluoromethyl-phenyl)-pyridin-3-yl]-ethoxy}-benzoylamino)-propionic acid

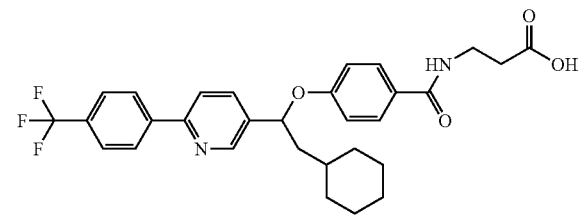

MS (ES): 541.3 [M+H]⁻.

Example 4

(R,S)-3-(4-{1-[5-(4-Trifluoromethyl-phenyl)-pyridin-2-yl]-propoxy}-benzoylamino)-propionic acid

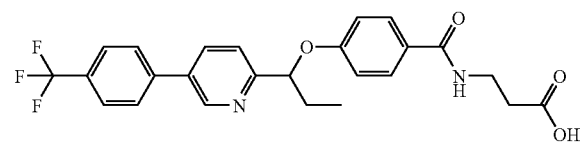

MS (ES): 471.2 [M+H]⁻.

Example 5

(R, S)-3-(4-{1-[6-(4-Trifluoromethyl-phenyl)-pyridin-3-yl]-heptyloxy}-benzoylamino)-propionic acid

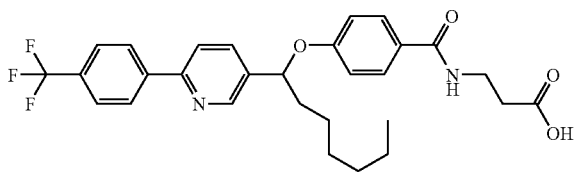

Step A. (R, S)-4-{1-[6-(4-Trifluoromethyl-phenyl)-pyridin-3-yl]-heptyloxy}-benzoic acid To a solution of 1-[6-(4-trifluoromethyl-phenyl)-pyridin-3-yl]-heptan-1-ol (280 mg, 0.83 mmol) in THF (2 mL) and toluene (4 mL) is added 1,1'-(azodicarbonyl)dipiperidine (ADDP, 314.1 mg, 1.24 mmol) at 0° C., followed by the addition of tributylphosphine (0.31 mL, 1.24 mmol) and methyl 4-hydroxybenzoate (151.5 mg, 1 mmol). The reaction mixture is warmed up to room temperature and stirred overnight. The mixture is loaded on silica gel, eluted with hexanes with a gradient from 0% of ethyl acetate to 50% of ethyl acetate giving ethyl 4-{1-[6-(4-trifluoromethyl-phenyl)-pyridin-3-yl]-heptyloxy}-benzoate. The ester product is taken into ethanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving 4-{1-[6-(4-trifluoromethyl-phenyl)-pyridin-3-yl]-heptyloxy}-benzoic acid (330 mg).

Step B. (R, S)-Methyl 3-(4-{1-[6-(4-Trifluoromethyl-phenyl)-pyridin-3-yl]-heptyloxy}-benzoylamino)-propionoate To a mixture of 4-{1-[6-(4-trifluoromethyl-phenyl)-pyridin-3-yl]-heptyloxy}-benzoic acid (230 mg, 0.5 mmol) in methylene chloride (5 mL) are added triethyl amine (0.21 mL, 1.51 mmol), DMAP (5.0 mg), 3-amino-propionic acid methyl ester (210.5 mg, 1.51 mmol) and EDCI (290 mg, 1.51 mmol) at room temperature. The reaction mixture is stirred at room temperature overnight, loaded on silica gel, eluted with eluted with hexanes with a gradient from 0% of ethyl acetate to 100% of ethyl acetate giving methyl 3-(4-{1-[6-(4-trifluoromethyl-phenyl)-pyridin-3-yl]-heptyloxy}-benzoylamino)-propionoate (260 mg).

Step C. (R, S)-3-(4-{1-[6-(4-Trifluoromethyl-phenyl)-pyridin-3-yl]-heptyloxy}-benzoylamino)-propionic acid To a mixture of 3-(4-{1-[6-(4-trifluoromethyl-phenyl)-pyridin-3-yl]-heptyloxy}-benzoylamino)-propionic acid methyl ester (60 mg, 0.11 mmol) in ethanol (2 mL) is added sodium hydroxide (5 N aqueous, 1 mL) and stirred for 2 h. The reaction mixture is concentrated and acidified by 5 N HCl (1.1 mL), extracted with ethyl acetate. Combined organic layers are washed with water and brine, dried over sodium sulfate. Concentration gives the title compound (53 mg). MS (ES): 529.3 [M+H]⁺.

Example 6

(R, S)-3-(4-{2-Cyclohexyl-1-[6-(4-trifluoromethyl-phenyl)-pyridin-3-yl]-ethylsulfanyl}-benzoylamino)-propionic acid

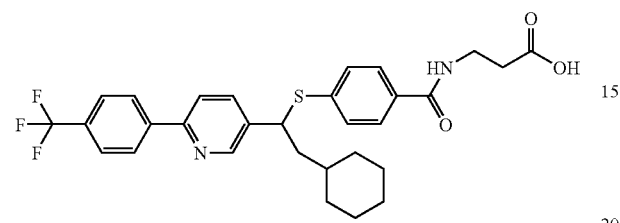

Step A. (R, S)-4-{2-Cyclohexyl-1-[6-(4-trifluoromethyl-phenyl)-pyridin-3-yl]-ethylsulfanyl}-benzoic acid To a solution of 2-cyclohexyl-1-[6-(4-trifluoromethyl-phenyl)-pyridin-3-yl]-ethanol (300 mg, 0.88 mmol) in THF (2 mL) and toluene (4 mL) is added 1,1'-(azodicarbonyl) dipiperidine (ADDP, 325.0 mg, 1.29 mmol) at 0° C., followed by the addition of tributylphosphine (0.32 mL, 1.29 mmol) and methyl 4-mercaptobenzoate (173.3 mg, 1.03 mmol). The reaction mixture is warmed up to room temperature and stirred overnight. The mixture is loaded on silica gel, eluted with hexanes with a gradient from 0% of ethyl acetate to 50% of ethyl acetate giving 4-{2-cyclohexyl-1-[6-(4-trifluoromethyl-phenyl)-pyridin-3-yl]-ethylsulfanyl}-benzoic acid methyl ester. The ester product is taken into ethanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving 4-{2-cyclohexyl-1-[6-(4-trifluoromethyl-phenyl)-pyridin-3-yl]-ethylsulfanyl}-benzoic acid (190 mg).

Step B. (R, S)-3-(4-{2-Cyclohexyl-1-[6-(4-trifluoromethyl-phenyl)-pyridin-3-yl]-ethylsulfanyl}-benzoylamino)-propionic acid methyl ester To a mixture of 4-{2-cyclohexyl-1-[6-(4-trifluoromethyl-phenyl)-pyridin-3-yl]-ethylsulfanyl}-benzoic acid (100 mg, 0.5 mmol) in methylene chloride (5 mL) are added triethyl amine (0.09 mL, 0.62 mmol), DMAP (5.0 mg), 3-amino-propionic acid methyl ester (86.2 mg, 0.62 mmol) and EDCI (118.7 mg, 0.62 mmol) at room temperature. The reaction mixture is stirred at room temperature overnight, loaded on silica gel, eluted with eluted with hexanes with a gradient from 0% of ethyl acetate to 100% of ethyl acetate giving 3-(4-{2-cyclohexyl-1-[6-(4-trifluoromethyl-phenyl)-pyridin-3-yl]-ethylsulfanyl}-benzoylamino)-propionic acid methyl ester (90 mg).

Step C. (R,S)-3-(4-{2-cyclohexyl-1-[6-(4-trifluoromethyl-phenyl)-pyridin-3-yl]-ethylsulfanyl}-benzoylamino)-propionic acid To a mixture of 3-(4-{2-cyclohexyl-1-[6-(4-trifluoromethyl-phenyl)-pyridin-3-yl]-ethylsulfanyl}-benzoylamino)-propionic acid methyl ester (90 mg) in ethanol (2 mL) is added sodium hydroxide (5 N aqueous, 1 mL) and stirred for 2 h. The reaction mixture is concentrated and acidified by 5 N HCl (1.1 mL), extracted with ethyl acetate. Combined organic layers are washed with water and brine, dried over sodium sulfate. Concentration gives the title compound (85 mg). MS (ES): 557.1 [M+H]⁺.

The following compounds are made in a manner substantially similar to Example 6.

Example 7

(R,S)-3-(4-{1-[6-(4-Trifluoromethyl-phenyl)-pyridin-3-yl]-heptylsulfanyl}-benzoylamino)-propionic acid

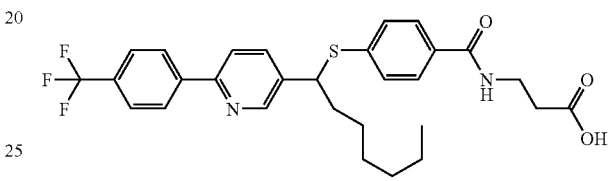

MS (ES): 543.3 [M+H]⁻.

Example 8

(R, S)-3-(4-{1-[6-(4-Trifluoromethyl-phenyl)-pyridin-3-yl]-propoxy}-benzoylamino)-propionic acid

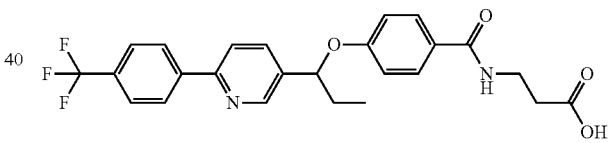

Step A. (R, S)-4-{1-[6-(4-Trifluoromethyl-phenyl)-pyridin-3-yl]-propoxy}-benzoic acid To a solution of 1-[6-(4-trifluoromethyl-phenyl)-pyridin-3-yl]-propoxy-1-ol (280 mg, 1.0 mmol) in THF (2 mL) and toluene (4 mL) is added 1,1'-(azodicarbonyl)dipiperidine (ADDP, 376.8 mg, 1.49 mmol) at 0° C., followed by the addition of triphenylphosphine (391.6 mg, 1.49 mmol) and methyl 4-hydroxybenzoate (181.7 mg, 1.19 mmol). The reaction mixture is warmed up to room temperature and stirred overnight. The mixture is loaded on silica gel, eluted with hexanes with a gradient from 0% of ethyl acetate to 50% of ethyl acetate giving ethyl 4-{1-[6-(4-trifluoromethyl-phenyl)-pyridin-3-yl]-propoxy}-benzoate (350 mg). The ester product is taken into ethanol (4 mL), treated with sodium hydroxide (5N aqueous, 1 mL) for 3 h at 40° C. The mixture is concentrated, diluted with ethyl acetate, acidified with 5 N HCl (1.1 mL), extracted with ethyl acetate. The organic layers are dried and concentrated giving 4-{1-[6-(4-trifluoromethyl-phenyl)-pyridin-3-yl]-propoxy}-benzoic acid (345 mg).

Step B. (R, S)-tert-Butyl 3-(4-{1-[6-(4-trifluoromethyl-phenyl)-pyridin-3-yl]-propoxy}-benzoylamino)-propionate To a mixture of 4-{1-[6-(4-trifluoromethyl-phenyl)-pyridin-3-yl]-propoxy}-benzoic acid (345 mg, 0.86 mmol) in methylene chloride (10 mL) are added triethyl amine (0.36 mL, 2.58 mmol), DMAP (5.0 mg), 3-amino-propionic acid tert-butyl ester (468.2 mg, 2.58 mmol) and EDCI (495.6 mg, 2.58 mmol) at room temperature. The reaction mixture is stirred at room temperature overnight, loaded on silica gel, eluted with eluted with hexanes with a gradient from 0% of ethyl acetate to 100% of ethyl acetate giving methyl 3-(4-{1-[6-(4-trifluoromethyl-phenyl)-pyridin-3-yl]-propoxy}-benzoylamino)-propionoate (400 mg).

Step C. (R, S)-3-(4-{1-[6-(4-Trifluoromethyl-phenyl)-pyridin-3-yl]-propoxy}-benzoylamino)-propionic acid To a mixture of 3-(4-{1-[6-(4-trifluoromethyl-phenyl)-pyridin-3-yl]-propoxy}-benzoylamino)-propionic acid tert-butyl ester (50 mg, 0.1 mmol) in ethanol (1 mL) is added sodium hydroxide (5 N aqueous, 0.5 mL) and stirred for 2 h at 40° C. The reaction mixture is concentrated and acidified by 5 N HCl (0.55 mL), extracted with ethyl acetate. Combined organic layers are washed with water and brine, dried over sodium sulfate. Concentration gives the title compound (40 mg). MS (ES): 471.45 [M+H]$^-$.

Example 9 & Example 10

(R) and (S)-3-(4-{2-Cyclohexyl-1-[6-(4-trifluoromethyl-phenyl)-pyridin-3-yl]-ethoxy}-benzoylamino)-propionic acid

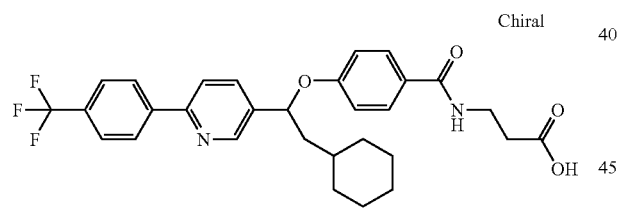
Chiral

Step A. (R) and (S)-4-{2-Cyclohexyl-1-[6-(4-trifluoromethyl-phenyl)-pyridin-3-yl]-ethoxy}-benzoic acid methyl ester

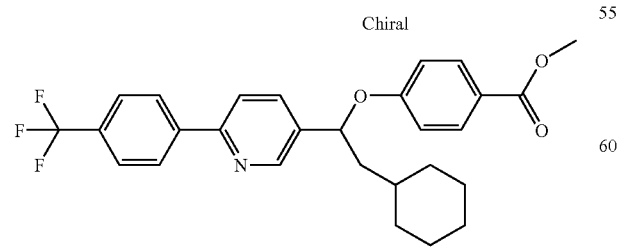
Chiral

Racemic 4-{2-cyclohexyl-1-[6-(4-trifluoromethyl-phenyl)-pyridin-3-yl]-ethoxy}-benzoic acid methyl ester is resolved by Chiral HPLC on a Chiralpak AD-H column eluted with 20% isopropanol and 80% heptane to give the enantiomers.

Step B. (R) and (S)-4-{2-Cyclohexyl-1-[6-(4-trifluoromethyl-phenyl)-pyridin-3-yl]-ethoxy}-benzoic acid (R) or (S)-4-{2-cyclohexyl-1-[6-(4-trifluoromethyl-phenyl)-pyridin-3-yl]-ethoxy}-benzoic acid methyl ester (85 mg) is taken into ethanol (2 mL), treated with 5N NaOH (1 mL) for 2 h at 40° C., concentrated, acidified with 5 N HCl, extracted with ethyl acetate, dried over sodium sulfate. Concentration gives 80 mg of (R) or (S)-4-{2-cyclohexyl-1-[6-(4-trifluoromethyl-phenyl)-pyridin-3-yl]-ethoxy}-benzoic acid.

Step C. (R) and (S)-3-(4-{2-Cyclohexyl-1-[6-(4-trifluoromethyl-phenyl)-pyridin-3-yl]-ethylsulfanyl}-benzoylamino)-propionic acid To a mixture of (R) or (S)-4-{2-cyclohexyl-1-[6-(4-trifluoromethyl-phenyl)-pyridin-3-yl]-ethoxy}-benzoic acid (80 mg, 0.17 mmol) in methylene chloride (5 mL) are added triethyl amine (0.07 mL, 0.51 mmol), DMAP (5.0 mg), 3-amino-propionic acid tert-butyl ester (92.8 mg, 0.51 mmol) and EDCI (98.2 mg, 0.51 mmol) at room temperature. The reaction mixture is stirred at room temperature overnight, loaded on silica gel, eluted with eluted with hexanes with a gradient from 0% of ethyl acetate to 100% of ethyl acetate giving (R) or (S)-3-(4-{2-cyclohexyl-1-[6-(4-trifluoromethyl-phenyl)-pyridin-3-yl]-ethoxy}-benzoylamino)-propionic acid tert-butyl ester. The ester product is taken into ethanol (2 mL), treated with 5N NaOH (1 mL) for 2 h at 40° C., concentrated, acidified with 5 N HCl, extracted with ethyl acetate, dried over sodium sulfate. Concentration gives (R) or (S)-3-(4-{2-cyclohexyl-1-[6-(4-trifluoromethyl-phenyl)-pyridin-3-yl]-ethoxy}-benzoylamino)-propionic acid (80 mg).
Isomer 1: MS (ES): 539.5 [M+H]$^-$.
Isomer 2: MS (ES): 541.2 [M+H]$^+$.

Example 11 & Example 12

(R) and (S)-3-(4-{1-[6-(4-Trifluoromethyl-phenyl)-pyridin-3-yl]-heptyloxy}-benzoylamino)-propionic acid

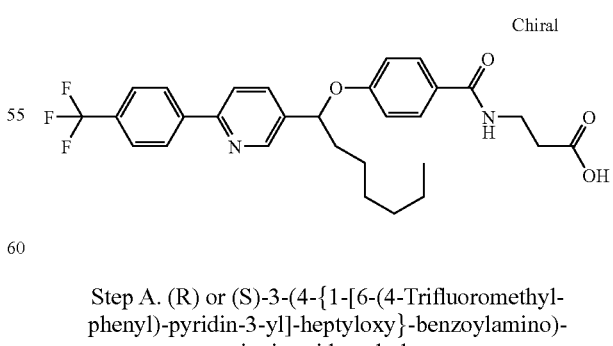
Chiral

Step A. (R) or (S)-3-(4-{1-[6-(4-Trifluoromethyl-phenyl)-pyridin-3-yl]-heptyloxy}-benzoylamino)-propionic acid methyl ester Racemic 3-(4-{1-[6-(4-trifluoromethyl-phenyl)-pyridin-3-yl]-heptyloxy}-benzoylamino)-propionic acid methyl ester is resolved by Chiral HPLC on a Chiralpak AD-H column eluted with 40% isopropanol and 60% heptane to give the enantiomers.

Step B. (R) and (S)-3-(4-{1-[6-(4-Trifluoromethyl-phenyl)-pyridin-3-yl]-heptyloxy}-benzoylamino)-propionic acid (R) or (S)-3-(4-{1-[6-(4-Trifluoromethyl-phenyl)-pyridin-3-yl]-heptyloxy}-benzoylamino)-propionic acid methyl ester is taken into ethanol (2 mL), treated with 5N NaOH (1 mL) for 2 h, concentrated, acidified with 5 N HCl, extracted with ethyl acetate, dried over sodium sulfate. Concentration gives (R) or (S)-3-(4-{1-[6-(4-Trifluoromethyl-phenyl)-pyridin-3-yl]-heptyloxy}-benzoylamino)-propionic acid.
Isomer 1: MS (ES): 527.3 [M+H]$^-$.
Isomer 2: MS (ES): 529.2 [M+H]$^+$.
The following enantiomers are obtained by chiral HPLC in a manner substantially similar to examples 11 and 12.

Example 13 & Example 14

(R) and (S)-3-(4-{1-[6-(4-Trifluoromethyl-phenyl)-pyridin-3-yl]-propoxy}-benzoylamino)-propionic acid

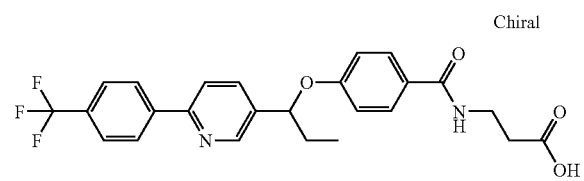

Chiral

Isomer 1: MS (ES): 473.1 [M+H]$^+$.
Isomer 2: MS (ES): 473.1 [M+H]$^+$.

Example 15

3-[4-(3-Methyl-4'-trifluoromethyl-biphenyl-4-ylmethoxy)-benzoylamino]-propionic acid

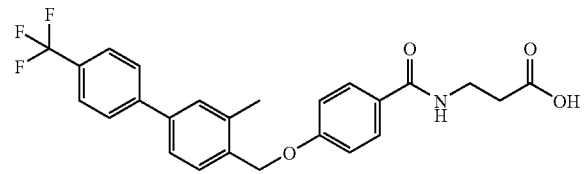

Step A. 3-[4-(3-Methyl-4'-trifluoromethyl-biphenyl-4-ylmethoxy)-benzoylamino]-propionic acid methyl ester To a solution of 3-(4-hydroxy-benzoylamino)-propionic acid methyl ester (0.11 g, 0.49 mmol) and 4-chloromethyl-3-methyl-4'-trifluoromethyl-biphenyl (0.12 g, 0.41 mmol) in acetonitrile (4 mL) is added Cs$_2$CO$_3$ (0.20 g, 0.61 mmol). The mixture is stirred at RT for 12 h. The mixture is diluted with water and extracted with EtOAc. The organics are dried with MgSO$_4$, and the crude material is purified by flash chromatography to yield 0.11 g (58%) of the title compound.

Step B. 3-[4-(3-Methyl-4'-trifluoromethyl-biphenyl-4-ylmethoxy)-benzoylamino]-propionic acid A mixture of 3-[4-(3-methyl-4'-trifluoromethyl-biphenyl-4-ylmethoxy)-benzoylamino]-propionic acid methyl ester (0.11 g) and 5M NaOH (1.5 mL) in THF (3 mL) is heated to 70° C. for 12 h. The mixture is acidified with 5M HCl, and extracted with EtOAc. The organics are washed with water and brine, and dried with MgSO$_4$ to yield the title compound. MS (ES): 458 (M$^+$). The structure is also confirmed by $^1$H NMR.

Example 16

3-[4-(3-Methyl-3',5'-bis-trifluoromethyl-biphenyl-4-ylmethoxy)-benzoylamino]-propionic acid

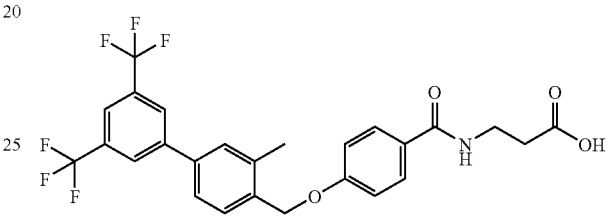

To a mixture of 3-[4-(4-bromo-2-methyl-benzyloxy)-benzoylamino]-propionic acid methyl ester (0.16 g, 0.39 mmol), 3,5-ditrifluoromethyl phenyl boronic acid (0.15 g, 0.58 mmol) in dioxane/water (1.5 mL: 1.5 mL) is added K$_2$CO$_3$ (0.16 g, 1.16 mmol) and POPd (from CombiPhos Inc.; 23 mg, 0.05 mmol). The mixture is heated at 100° C. for 2.5 h. Water is added, and the mixture is extracted with EtOAc. The organics are washed with brine and dried with MgSO$_4$. The crude material is purified by reverse phase chromatography to yield 20 mg (9%) of the title compound. MS (ES): 526 (M$^+$). The structure is also confirmed by $^1$H NMR.

Example 17

3-[4-(3-Methyl-biphenyl-4-ylmethoxy)-benzoylamino]-propionic acid

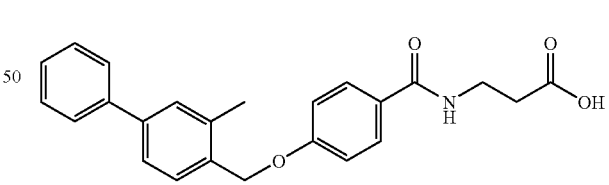

Step A. 3-[4-(3-Methyl-biphenyl-4-ylmethoxy)-benzoylamino]-propionic acid methyl ester A mixture of 3-[4-(4-bromo-2-methyl-benzyloxy)-benzoylamino]-propionic acid methyl ester (0.20 g, 0.49 mmol), phenyl boronic acid (0.09 g, 0.78 mmol), and Na$_2$CO$_3$ (0.11 g, 1.08 mmol) in toluene/water (3 mL: 1 mL) is degassed (2×). Pd(PPh$_3$)$_4$ (0.05 g, 0.04 mmol) is added, and the mixture is stirred at 100° C. for 12 h. The mixture is filtered through Celite. Water is added, and the mixture is extracted with EtOAc. The organics are dried with MgSO$_4$ and concentrated.

The crude material is purified by flash chromatography to yield 0.20 g (100%) of the title compound.

Step B. 3-[4-(3-Methyl-biphenyl-4-ylmethoxy)-benzoylamino]-propionic acid

A mixture of 3-[4-(3-methyl-biphenyl-4-ylmethoxy)-benzoylamino]-propionic acid methyl ester (0.17 g, 0.42 mmol) and 5M NaOH (2 mL) in THF (4 mL) is heated at 70° C. for 5 h. The mixture is acidified with 5M HCl, and extracted with EtOAc. The organics are washed with water and brine, and dried with $MgSO_4$ to yield the title compound (42 mg, 26%). MS (ES): 390 ($M^+$). The structure is also confirmed by $^1H$ NMR.

Example 18

(R,S)-3-(4-{(4-tert-Butyl-phenyl)-[6-(4-trifluoromethyl-phenyl)-pyridin-3-yl]-methoxy}-benzoylamino)-propionic acid

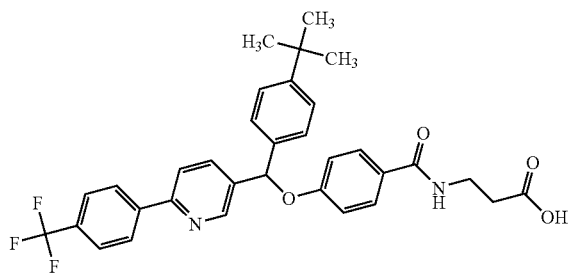

Step A. (R,S)-(4-tert-Butyl-phenyl)-[6-(4-trifluoromethyl-phenyl)-pyridin-3-yl]-methanol 6-(4-Trifluoromethyl-phenyl)-pyridine-3-carbaldehyde (1 g, 3.98 mmol) is dissolved in anhydrous tetrahydrofuran, (THF, 20 mL) and cooled to 0° C. while stirring under nitrogen. The Grignard reagent, 4-tert-butyl-benzyl magnesium bromide (3.0 mL, 2M in $Et_2O$, 6.0 mmol) is then added slowly over ten minutes. The reaction is stirred at 0° C. for 1 h., then allowed to warm to room temperature. The reaction is monitored by HPLC, and upon complete consumption of the aldehyde, the reaction is quenched with 1N HCl. The reaction is diluted with diethyl ether and water, followed by extraction. The organic layer is washed with water and brine, followed by drying over anhydrous sodium sulfate. The solution is filtered and concentrated, then further purified using flash column chromatography (650 mg, 1.69 mmol).

Step B. (R,S)-3-(4-{(4-tert-Butyl-phenyl)-[6-(4-trifluoromethyl-phenyl)-pyridin-3-yl]-methoxy}-benzoylamino)-propionic acid methyl ester A solution of 3-(4-hydroxy-benzoylamino)-propionic acid methyl ester (167 mg, 0.75 mmol) and (4-tert-butyl-phenyl)-[6-(4-trifluoromethyl-phenyl)-pyridin-3-yl]-methanol (550 mg, 1.42 mmol) in toluene (8.0 mL) is degassed and filled with nitrogen for 3 times. Tributylphosphine (0.540 mL, 2.14 mmol) is added to the reaction mixture under nitrogen at 0° C., followed by addition of 1,1'-(azodicarbonyl)-dipiperidine (540 mg, 2.14 mmol). The reaction mixture is allowed to warm to room temperature and stirred over night, the mixture is loaded on silica gel column. Chromatography gives the title compound (536 mg).

Step C. (R,S)-3-(4-{(4-tert-Butyl-phenyl)-[6-(4-trifluoromethyl-phenyl)-pyridin-3-yl]-methoxy}-benzoylamino)-propionic acid 3-(4-{(4-tert-Butyl-phenyl)-[6-(4-trifluoromethyl-phenyl)-pyridin-3-yl]-methoxy}-benzoylamino)-propionic acid methyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 575.34 $[M+H]^-$, the structure is also confirmed by proton NMR.

The following compounds are made in a manner substantially similar to example 18:

Example 19

(R,S)-3-(4-{1-[6-(4-Trifluoromethyl-phenyl)-pyridin-3-yl]-hexyloxy}-benzoylamino)-propionic acid

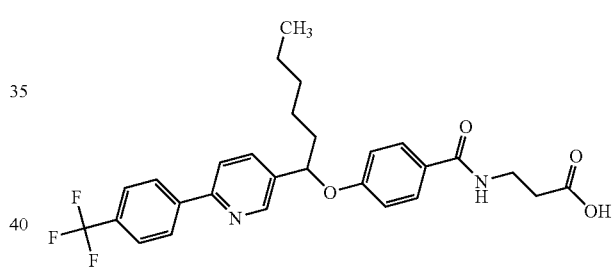

MS (ES): 513.28 $[M+H]^-$, the structure is also confirmed by proton NMR.

Example 20

(R,S)-3-(4-{1-[6-(4-Trifluoromethyl-phenyl)-pyridin-3-yl]-butoxy}-benzoylamino)-propionic acid

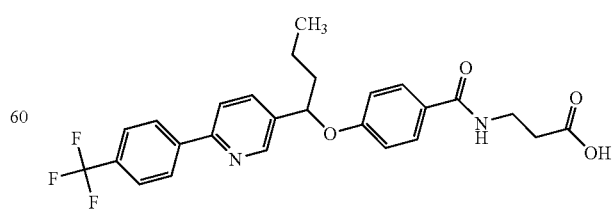

MS (ES): 458.18 $[M+H]^-$, the structure is also confirmed by proton NMR.

Example 21

(R,S)-3-(4-{1-[6-(4-Trifluoromethyl-phenyl)-pyridin-3-yl]-pentyloxy}-benzoylamino)-propionic acid

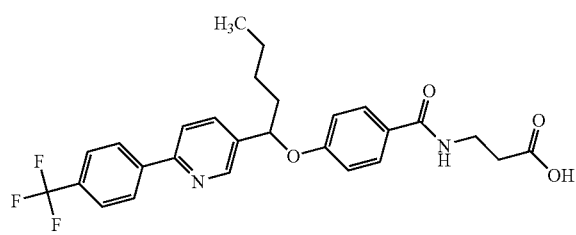

MS (ES): 499.19 [M+H]⁻, the structure is also confirmed by proton NMR.

Example 22

(R,S)-3-(4-{3-Cyclohexyl-1-[6-(4-trifluoromethyl-phenyl)-pyridin-3-yl]-propoxy}-benzoylamino)-propionic acid

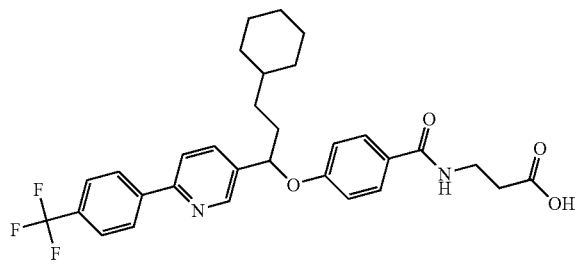

MS (ES): 553.22 [M+H]⁻, the structure is also confirmed by proton NMR.

Example 23

(R,S)-3-(4-{1-[6-(4-Trifluoromethyl-phenyl)-pyridin-3-yl]-nonyloxy}-benzoylamino)-propionic acid

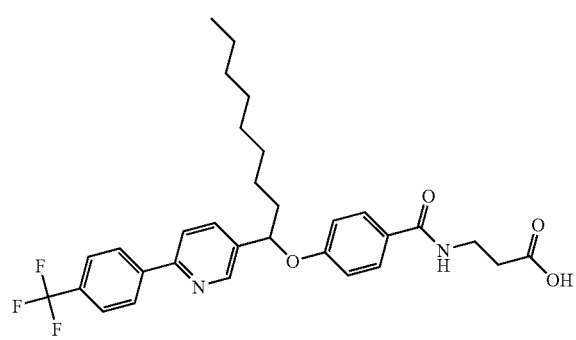

MS (ES): 555.3 [M+H]⁻, the structure is also confirmed by proton NMR.

Example 24

(R,S)-3-(4-{4,4-Dimethyl-1-[6-(4-trifluoromethyl-phenyl)-pyridin-3-yl]-pentyloxy}-benzoylamino)-propionic acid

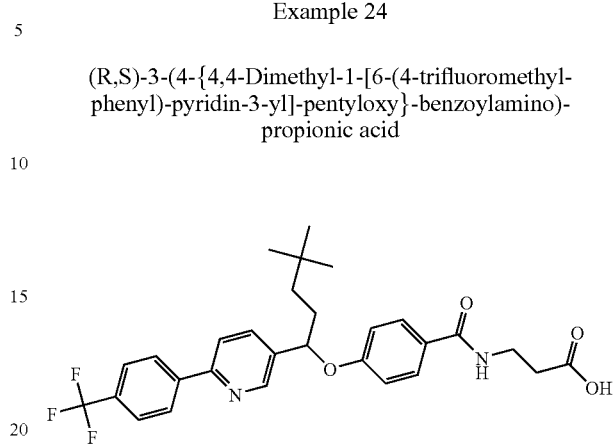

MS (ES): 527.19 [M+H]⁻, the structure is also confirmed by proton NMR.

Example 25

(R,S)-3-(4-{4,4,4-Trifluoro-1-[6-(4-trifluoromethyl-phenyl)-pyridin-3-yl]-butoxy}-benzoylamino)-propionic acid

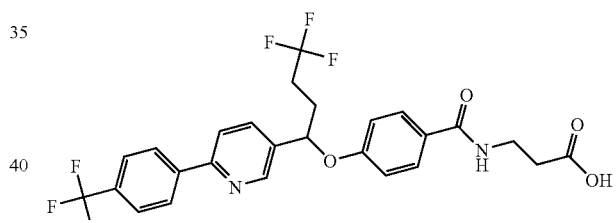

MS (ES): 539.1 [M+H]⁻, the structure is also confirmed by proton NMR.

Example 26

(R,S)-3-(4-{5,5,5-Trifluoro-1-[6-(4-trifluoromethyl-phenyl)-pyridin-3-yl]-pentyloxy}-benzoylamino)-propionic acid

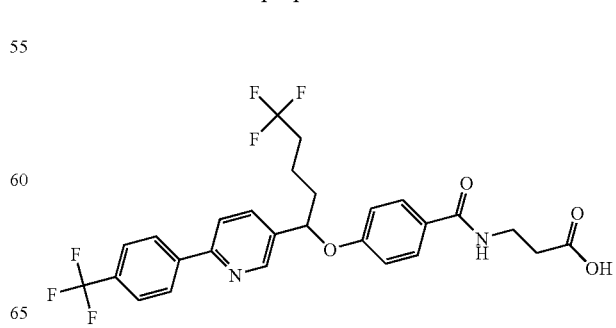

MS (ES): 553.1 [M+H]⁻, the structure is also confirmed by proton NMR.

Example 27

(R,S)-3-(4-{5,5,5-Trifluoro-1-[6-(4-trifluoromethyl-phenyl)-pyridin-3-yl]-pentylsulfanyl}-benzoylamino)-propionic acid

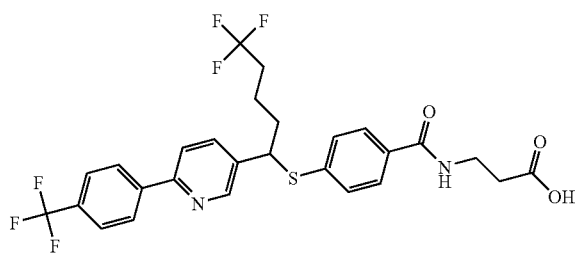

MS (ES): 569.14 [M+H]⁻, the structure is also confirmed by proton NMR.

Example 28

(R,S)-3-(4-{3,3-Dimethyl-1-[6-(4-trifluoromethyl-phenyl)-pyridin-3-yl]-butoxy}-benzoylamino)-propionic acid

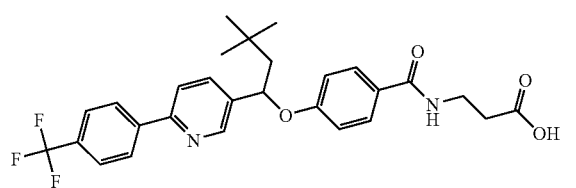

MS (ES): 513.16 [M+H]⁻, the structure is also confirmed by proton NMR.

Example 29

3-(4-{(4-tert-Butyl-phenyl)-[6-(4-trifluoromethyl-phenyl)-pyridin-3-yl]-methoxy}-benzoylamino)-propionic acid, Isomer 1

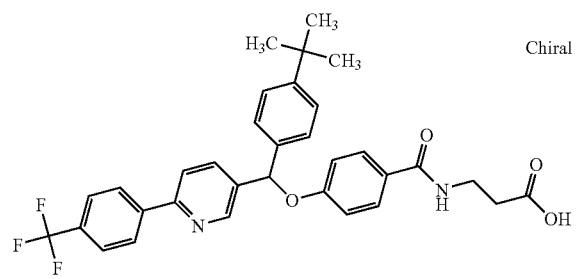

Chiral Separation

The racemic 3-(4-{(4-tert-Butyl-phenyl)-[6-(4-trifluoromethyl-phenyl)-pyridin-3-yl]-methoxy}-benzoylamino)-propionic acid methyl ester is resolved on a Chiralpak AD column (4.6×150 mm) with a flow rate of 0.6 mL/min. and detection at 260 nm. Eluted with methyl alcohol in heptane with 0.2% dimethyl-ethylamine and concentrated the fractions to provide a purified enantiomer ester (isomer 1, 98.9% ee). Hydrolysis of the purified enantiomer of the ester provides the title compound as a white solid. MS (ES): 577.34 [M+H]⁺, 575.34 [M+H]⁻, the structure is also confirmed by proton NMR.

The following enantiomeric compounds are obtained by chiral separation similar to Example 29 using Chiralcel OD column (4.6×250 mm), Chiralpak AD column (4.6×150 mm), or using Chiralcel OJ column (4.6×250 mm):

Example 30

3-(4-{(4-tert-Butyl-phenyl)-[6-(4-trifluoromethyl-phenyl)-pyridin-3-yl]-methoxy}-benzoylamino)-propionic acid, Isomer 2

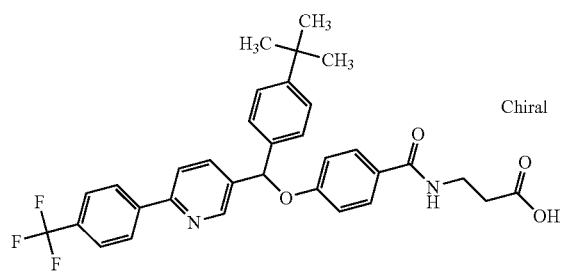

MS (ES): 575.34 [M+H]⁻, the structure is also confirmed by proton NMR.

Example 31

3-(4-{1-[6-(4-Trifluoromethyl-phenyl)-pyridin-3-yl]-hexyloxy}-benzoylamino)-propionic acid, Isomer 1

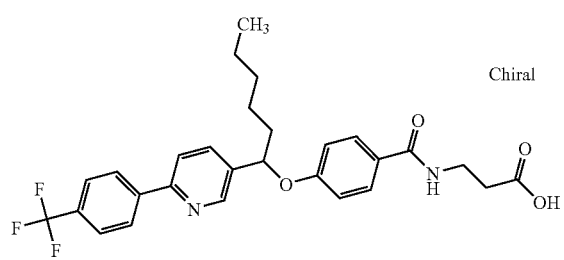

MS (ES): 513.28 [M+H]⁻, the structure is also confirmed by proton NMR.

Example 32

3-(4-{1-[6-(4-Trifluoromethyl-phenyl)-pyridin-3-yl]-hexyloxy}-benzoylamino)-propionic acid, Isomer 2

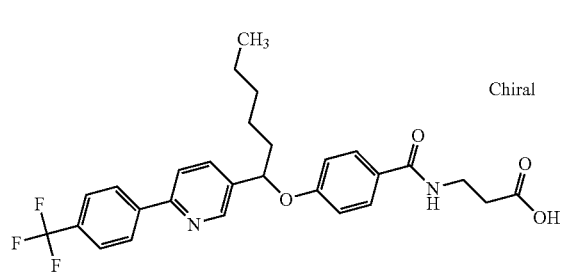

MS (ES): 473.16 [M+H]⁻, the structure is also confirmed by proton NMR.

Example 33

3-(4-{1-[6-(4-Trifluoromethyl-phenyl)-pyridin-3-yl]-butoxy}-benzoylamino)-propionic acid, Isomer 1

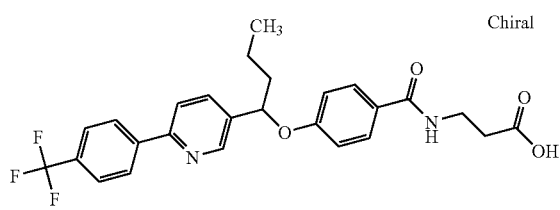

MS (ES): 485.2 [M+H]⁻, the structure is also confirmed by proton NMR.

Example 34

3-(4-{1-[6-(4-Trifluoromethyl-phenyl)-pyridin-3-yl]-butoxy}-benzoylamino)-propionic acid, Isomer 2

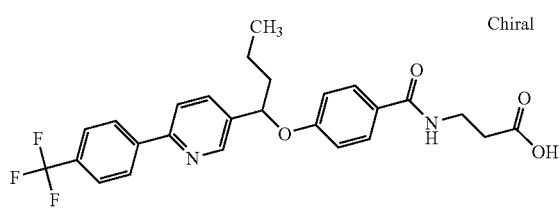

MS (ES): 485.2 [M+H]⁻, the structure is also confirmed by proton NMR.

Example 35

3-(4-{(3-Cyclohexyl-1-[6-(4-trifluoromethyl-phenyl)-pyridin-3-yl]-propoxy}-benzoylamino)-propionic acid, Isomer 1

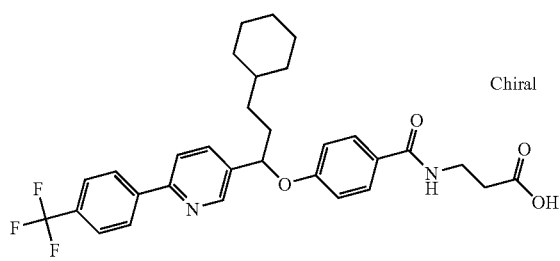

MS (ES): 553.24 [M+H]⁻, the structure is also confirmed by proton NMR.

Example 36

3-(4-{3-Cyclohexyl-1-[6-(4-trifluoromethyl-phenyl)-pyridin-3-yl]-propoxy}-benzoylamino)-propionic acid, Isomer 2

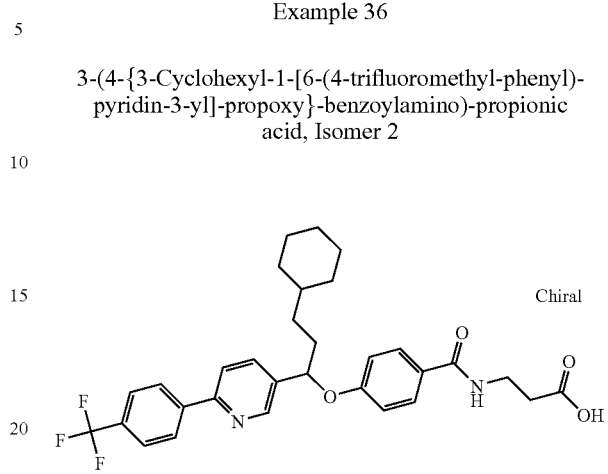

MS (ES): 553.24 [M+H]⁻, the structure is also confirmed by proton NMR.

Example 37

3-(4-{4,4-Dimethyl-1-[6-(4-trifluoromethyl-phenyl)-pyridin-3-yl]-pentyloxy}-benzoylamino)-propionic acid, Isomer 1

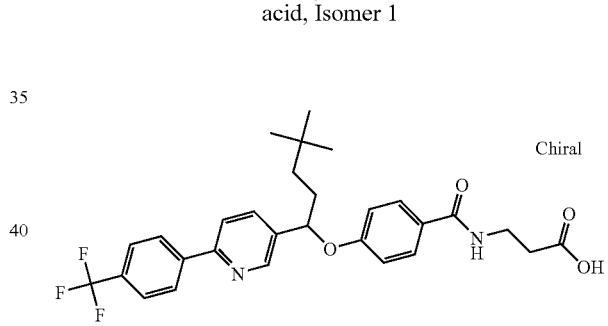

MS (ES): 527.17 [M+H]⁻, the structure is also confirmed by proton NMR.

Example 38

3-(4-{4,4-Dimethyl-1-[6-(4-trifluoromethyl-phenyl)-pyridin-3-yl]-pentyloxy}-benzoylamino)-propionic acid, Isomer 2

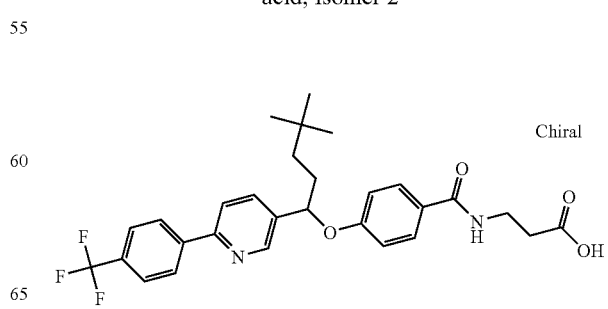

MS (ES): 527.2 [M+H]⁻, the structure is also confirmed by proton NMR.

Example 39

3-(4-{4,4,4-Trifluoro-1-[6-(4-trifluoromethyl-phenyl)-pyridin-3-yl]-butoxy}-benzoylamino)-propionic acid, Isomer 1

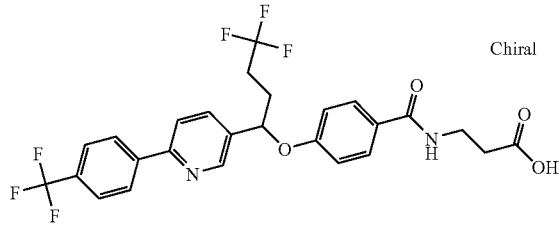

MS (ES): 539.13 [M+H]⁻, the structure is also confirmed by proton NMR.

Example 40

3-(4-{4,4,4-Trifluoro-1-[6-(4-trifluoromethyl-phenyl)-pyridin-3-yl]-butoxy}-benzoylamino)-propionic acid, Isomer 2

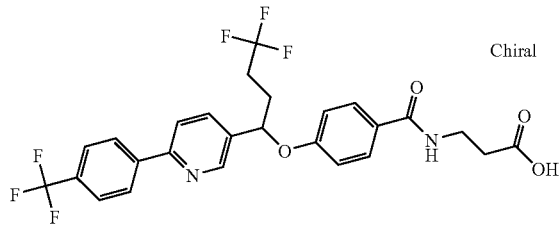

MS (ES): 539.13 [M+H]⁻, the structure is also confirmed by proton NMR.

Example 41

3-(4-{5,5,5-Trifluoro-1-[6-(4-trifluoromethyl-phenyl)-pyridin-3-yl]-pentyloxy}-benzoylamino)-propionic acid, Isomer 1

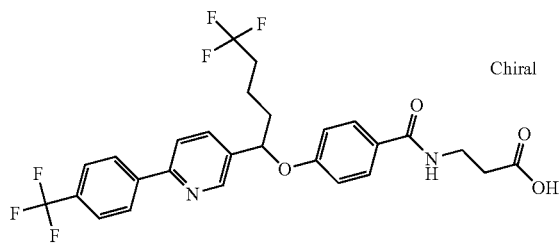

MS (ES): 553.11 [M+H]⁻, the structure is also confirmed by proton NMR.

Example 42

3-(4-{5,5,5-Trifluoro-1-[6-(4-trifluoromethyl-phenyl)-pyridin-3-yl]-pentyloxy}-benzoylamino)-propionic acid, Isomer 2

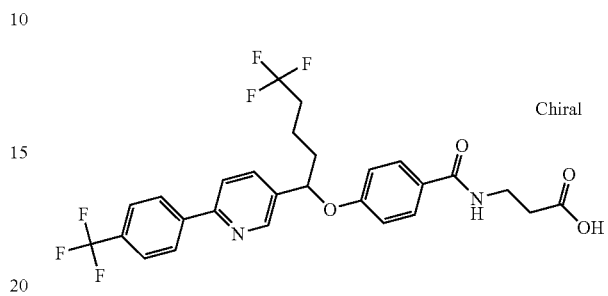

MS (ES): 553.11 [M+H]⁻, the structure is also confirmed by proton NMR.

Example 43

3-(4-{1-[6-(2-Trifluoromethyl-phenyl)-pyridin-3-yl]-hexyloxy}-benzoylamino)-propionic acid

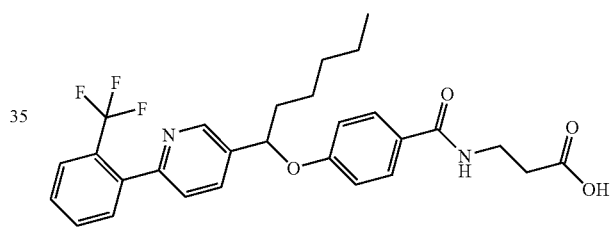

Step A.
6-Chloro-N-methoxy-N-methyl-nicotinamide

6-Chloro-nicotinic acid methyl ester (6 g, 34.97 mmol) is dissolved into anhydrous tetrahydrofuran (THF) (200 mL) and then cooled to −30° C. while stirring under nitrogen. N,O-dimethylhydroxylamine hydrochloride (5.12 g, 52.46 mmol) is then added to the solution in one portion. Isopropyl magnesium chloride (52 mL, 2M in THF, 105 mmol) is slowly added to the cooled suspension over 1 h. After complete consumption of starting material, then 30% solution of ammonium chloride is added with stirring. The reaction is diluted with diethyl ether and extracted. The organic layer is collected and washed with cold water (2×) and brine. The solution is then dried over anhydrous sodium sulfate, filtered, and concentrated. The 6-chloro-N-methoxy-N-methyl-nicotinamide (6.20 g, 30.90 mmol) is obtained in pure form after flash column chromatography. ¹H NMR (CDCL₃, 400 MHz): δ 8.78 (d, J=1.5 Hz, 1H), 8.02 (dd, J=1.5 and 8.3 Hz, 1H), 7.40 (d, J=8.3 Hz, 1H), 3.57 (s, 3H), 3.40 (s, 3H); MS m/z 218, 201, 188, 171.

Step B. 1-(6-Chloro-pyridin-3-yl)-hexan-1-one

6-Chloro-N-methoxy-N-methyl-nicotinamide (6.20 g, 30.90 mmol) is suspended in anhydrous tetrahydrofuran (200 mL), and cooled to 0° C. with stirring under nitrogen. N-pentyl magnesium bromide (23 mL, 2.0M in diethyl ether, 46 mmol) is slowly added to the reaction over 1 h. The reaction is allowed to warm slowly to room temperature and monitored by TLC. Upon complete consumption of starting material, the reaction is carefully neutralized with 1N hydrochloric acid, extracted with diethyl ether, washed, dried, and concentrated. The 1-(6-chloro-pyridin-3-yl)-hexan-1-one (5.2 g, 24.8 mmol) 80% yield, is used without further purification.

Step C. (R,S)-1-(6-Chloro-pyridin-3-yl)-hexan-1-ol 1-(6-Chloro-pyridin-3-yl)-hexan-1-one (5.2 g, 24.8 mmol) is dissolved in ethanol and cooled to 0° C. while stirring under nitrogen. To the flask is added sodium borohydride (938 mg, 24.8 mmol), and the reaction is kept at 0° C. for 1 h., then slowly warmed to room temperature. The reaction is monitored by HPLC. Upon complete consumption of starting material, the reaction is carefully quenched with water, the ethanol removed by rotary evaporator, and extracted with diethyl ether, washed, dried, and concentrated. The title compound is used in the next step without further purification.

Step D. (R,S)-3-{4-[1-(6-Chloro-pyridin-3-yl)-hexyloxy]-benzoylamino}-propionic acid tert-butyl ester A solution of 3-(4-hydroxy-benzoylamino)-propionic acid tert-butyl ester (2.50 g, 0.75 mmol) and 1-(6-chloro-pyridin-3-yl)-hexan-1-ol (2.0 g, 9.38 mmol) in toluene (40.0 mL) is degassed and filled with nitrogen for 3 times. Tributylphosphine (3.5 mL, 14 mmol) is added to the reaction mixture under nitrogen at 0° C., followed by addition of 1,1'-(azodicarbonyl)-dipiperidine (3.5 g, 14 mmol). The reaction mixture is allowed to warm to room temperature and stirred over night, the mixture is loaded on silica gel column. Chromatography gives the title compound (1.67 g).

Step E. (R,S)-3-(4-{1-[6-(2-Trifluoromethyl-phenyl)-pyridin-3-yl]-hexyloxy}-benzoylamino)-propionic acid tert-butyl ester 3-{4-[1-(6-Chloro-pyridin-3-yl)-hexyloxy]-benzoylamino}-propionic acid tert-butyl ester (359 mg, 0.781 mmol) is dissolved in toluene (2.5 mL), followed by palladium tetrakis triphenylphosphine (46 mg, 0.0395 mmol), 2-trifluoromethyl-phenyl boronic acid (163 mg, 0.860 mmol), and potassium fluoride (90.7 mg, 1.56 mmol). The reaction is purged with nitrogen and heated to reflux, then the water (2.5 mL) is added. The reaction is monitored by HPLC, and upon completion, allowed to cool to room temperature. The reaction is diluted with EtOAc and then celite added, followed by water. This mixture is then filtered through a pad of celite. The layers are separated, then the organic layer is washed with 0.1N sodium hydroxide, water, and brine. The organic layer is dried over anhydrous sodium sulfate, then concentrated. The product is purified by flash column chromatography (228 mg).

Step F. (R,S)-3-(4-{1-[6-(2-Trifluoromethyl-phenyl)-pyridin-3-yl]-hexyloxy}-benzoylamino)-propionic acid 3-(4-{1-[6-(2-Trifluoromethyl-phenyl)-pyridin-3-yl]-hexyloxy}-benzoylamino)-propionic acid tert-butyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 575.34 [M+H]⁻, the structure is also confirmed by proton NMR.

The following compounds are made in a manner substantially similar to Example 43:

Example 44

(R,S)-3-(4-{1-[6-(3-Trifluoromethyl-phenyl)-pyridin-3-yl]-hexyloxy}-benzoylamino)-propionic acid

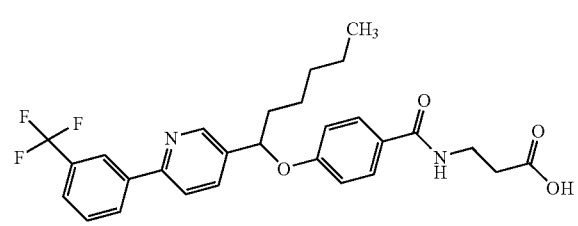

MS (ES): 513.28 [M+H]⁻, the structure is also confirmed by proton NMR.

Example 45

(R,S)-3-(4-{1-[6-(4-Fluoro-phenyl)-pyridin-3-yl]-hexyloxy}-benzoylamino)-propionic acid

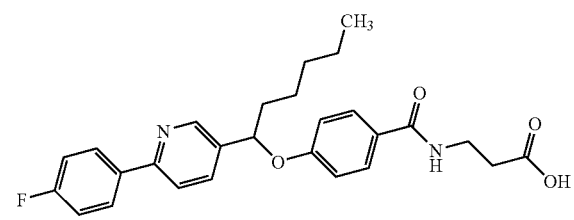

MS (ES): 463.21 [M+H]⁻, the structure is also confirmed by proton NMR.

Example 46

(R,S)-3-{4-[1-(6-p-Tolyl-pyridin-3-yl)-hexyloxy]-benzoylamino}-propionic acid

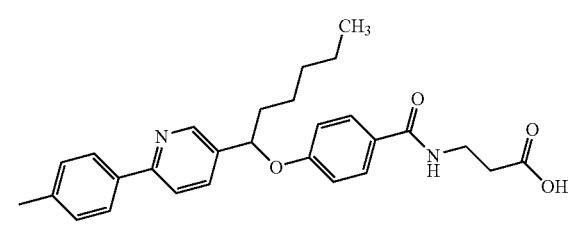

MS (ES): 459.27 [M+H]⁻, the structure is also confirmed by proton NMR.

Example 47

(R,S)-3-{4-[1-(6-Phenyl-pyridin-3-yl)-hexyloxy]-benzoylamino}-propionic acid

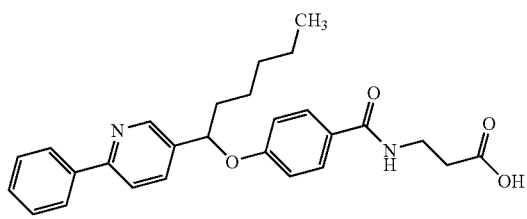

MS (ES): 445.18 [M+H]⁻, the structure is also confirmed by proton NMR.

Example 48

(R,S)-3-(4-{1-[6-(4-Trifluoromethoxy-phenyl)-pyridin-3-yl]-hexyloxy}-benzoylamino)-propionic acid

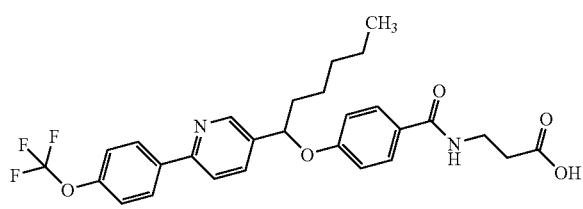

MS (ES): 529.3 [M+H]⁻, the structure is also confirmed by proton NMR.

Example 49

(R,S)-3-(4-{1-[6-(4-Methoxy-phenyl)-pyridin-3-yl]-hexyloxy}-benzoylamino)-propionic acid

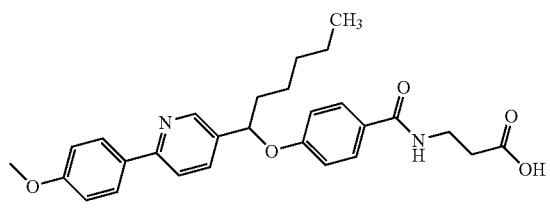

MS (ES): 475.22 [M+H]⁻, the structure is also confirmed by proton NMR.

Example 50

(R,S)-3-(4-{1-[6-(4-Isobutyl-phenyl)-pyridin-3-yl]-hexyloxy}-benzoylamino)-propionic acid

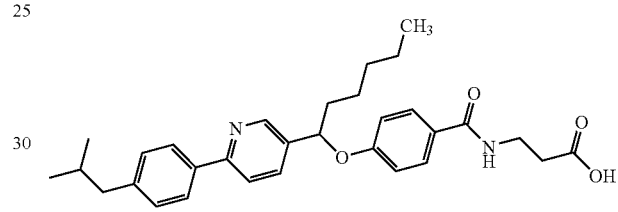

MS (ES): 501.29 [M+H]⁻, the structure is also confirmed by proton NMR.

Example 51

(R,S)-3-(4-{1-[6-(4-Cyclohexyl-phenyl)-pyridin-3-yl]-hexyloxy}-benzoylamino)-propionic acid

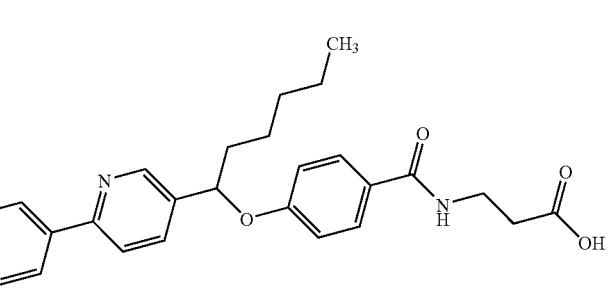

Example 52

(R,S)-3-(4-{1-[6-(4-Ethyl-phenyl)-pyridin-3-yl]-hexyloxy}-benzoylamino)-propionic acid

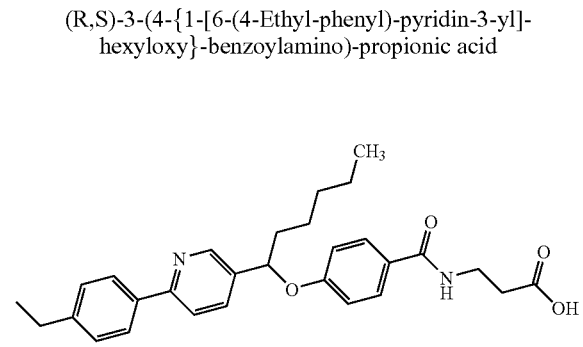

MS (ES): 473.25 [M+H]⁻, the structure is also confirmed by proton NMR.

Example 53

(R,S)-3-(4-{1-[6-(4-Pentyl-phenyl)-pyridin-3-yl]-hexyloxy}-benzoylamino)-propionic acid

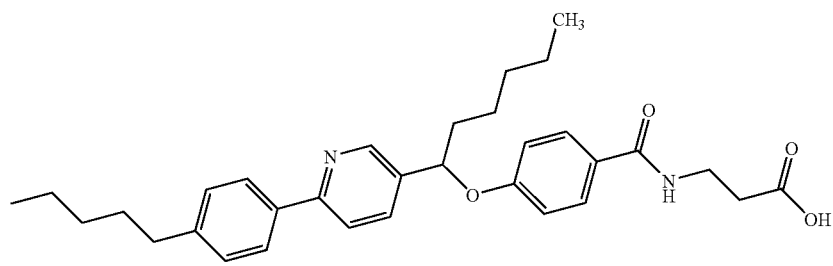

MS (ES): 515.31 [M+H]⁻, the structure is also confirmed by proton NMR.

Example 54

(R,S)-3-(4-{1-[6-(4-tert-Butyl-phenyl)-pyridin-3-yl]-hexyloxy}-benzoylamino)-propionic acid

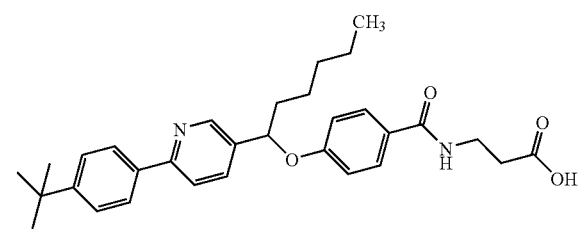

MS (ES): 527.3 [M+H]⁻, the structure is also confirmed by proton NMR.

Example 55

(R,S)-3-(4-{4,4-Dimethyl-1-[6-(2-trifluoromethyl-phenyl)-pyridin-3-yl]-pentyloxy}-benzoylamino)-propionic acid

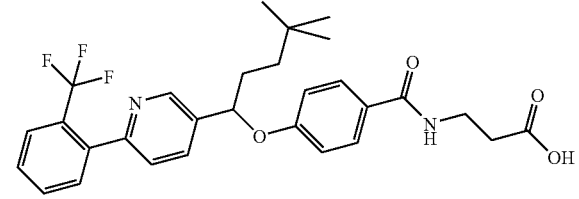

MS (ES): 527.2 [M+H]⁻, the structure is also confirmed by proton NMR.

Example 56

(R,S)-3-(4-{4,4-Dimethyl-1-[6-(3-trifluoromethyl-phenyl)-pyridin-3-yl]-pentyloxy}-benzoylamino)-propionic acid

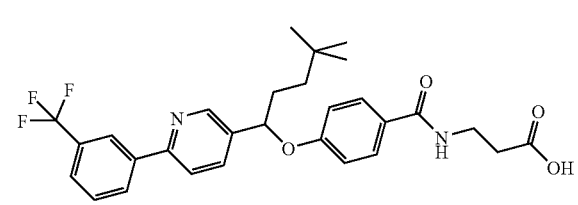

Example 57

(R,S)-3-(4-{1-[6-(3,5-Bis-trifluoromethyl-phenyl)-pyridin-3-yl]-4,4-dimethyl-pentyloxy}-benzoylamino)-propionic acid

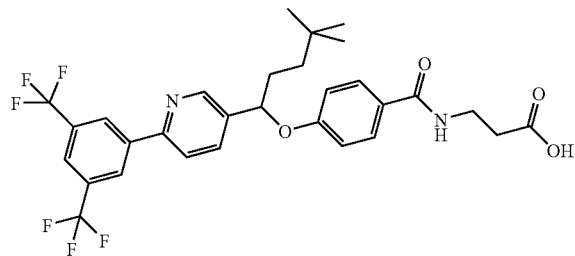

MS (ES): 595.14 [M+H]⁻, the structure is also confirmed by proton NMR.

Example 58

(R,S)-3-(4-{1-[6-(4-tert-Butyl-phenyl)-pyridin-3-yl]-4,4-dimethyl-pentyloxy}-benzoylamino)-propionic acid

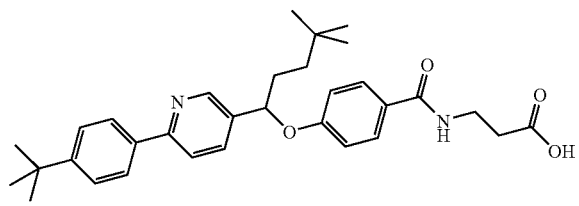

MS (ES): 515.25 [M+H]⁻, the structure is also confirmed by proton NMR.

Example 59

(R,S)-3-(4-{1-[6-(4-Isobutyl-phenyl)-pyridin-3-yl]-4,4-dimethyl-pentyloxy}-benzoylamino)-propionic acid

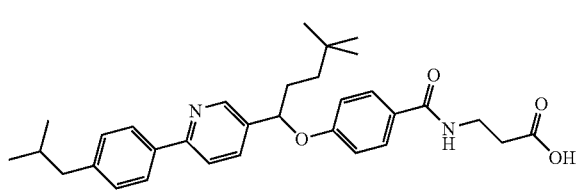

MS (ES): 515.27 [M+H]⁻, the structure is also confirmed by proton NMR.

Example 60

3-(4-{1-[6-(4-Trifluoromethoxy-phenyl)-pyridin-3-yl]-hexyloxy}-benzoylamino)-propionic acid, Isomer 1

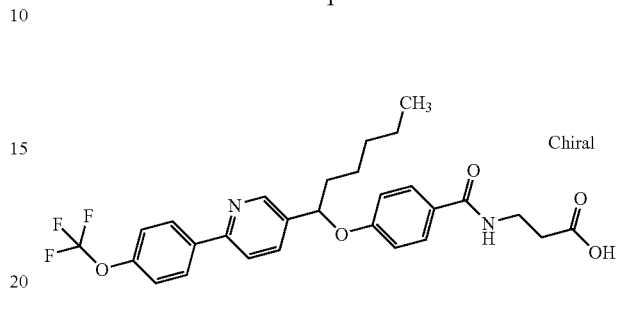

Chiral Separation

The racemic 3-(4-{1-[6-(4-trifluoromethoxy-phenyl)-pyridin-3-yl]-hexyloxy}-benzoylamino)-propionic acid tert-butyl ester is resolved on a Chiralpak AD column (4.6×150 mm) with a flow rate of 0.6 mL/min. and detection at 260 nm. Elute with methyl alcohol in heptane with 0.2% dimethylethylamine and concentrate the fractions to provide a purified enantiomer ester (isomer 1, 99.7% ee). Hydrolysis of the purified enantiomer of the ester provides the title compound as a white solid. MS (ES): 531.13 [M+H]⁺, 529.18 [M+H]⁻, the structure is also confirmed by proton NMR.

The following enantiomeric compounds are obtained by chiral separation similar to example 60 using Chiralcel OD column (4.6×250 mm), Chiralpak AD column (4.6×150 mm), or using Chiralcel OJ column (4.6×250 mm):

Example 61

3-(4-{1-[6-(4-Trifluoromethoxy-phenyl)-pyridin-3-yl]-hexyloxy}-benzoylamino)-propionic acid, Isomer 2

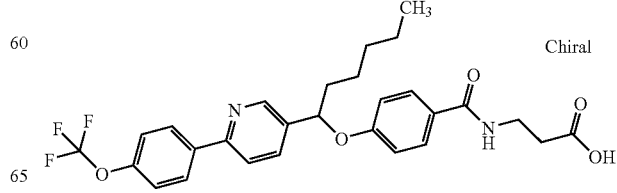

Example 62

3-(4-{1-[6-(4-tert-Butyl-phenyl)-pyridin-3-yl]-4,4-dimethyl-pentyloxy}-benzoylamino)-propionic acid, Isomer 1

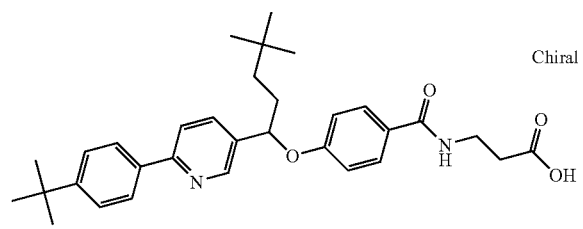

MS (ES): 515.26 [M+H]⁻, the structure is also confirmed by proton NMR.

Example 63

3-(4-{1-[6-(4-tert-Butyl-phenyl)-pyridin-3-yl]-4,4-dimethyl-pentyloxy}-benzoylamino)-propionic acid, Isomer 2

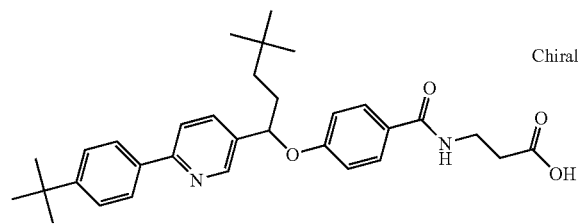

MS (ES): 515.27 [M+H]⁻, the structure is also confirmed by proton NMR.

Example 64

(R,S)-3-(4-{1-[2-(4-Trifluoromethyl-phenyl)-pyrimidin-5-yl]-heptyloxy}-benzoylamino)-propionic acid

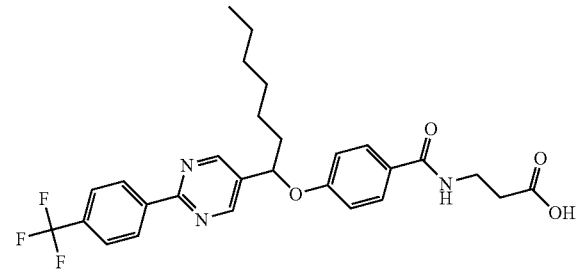

Step A. Sodium 3,3-dimethoxy-2-methoxycarbonylprop-1-en-1-oxide

A 250 mL, three neck, round bottom flask equipped with magnetic stirrer and a reflux condenser is purged with nitrogen. The flask is then charged sequentially with methyl 3,3-dimethoxyproprionate (5.22 g, 35.3 mmol), anhydrous 1,2-dimethoxyethane (25 mL), anhydrous methyl formate (5 mL), 60% NaH (1.70 g, 42.5 mmol), and the mixture is warmed to 40-50° C. until evolution of hydrogen gas is observed. The reaction mixture is immediately cooled in an ice water bath and slowly allowed to come to room temperature overnight with stirring. Anhydrous diethyl ether (25 mL) is added, and the resulting suspension is filtered under nitrogen, washed with anhydrous diethyl ether (10 mL), and vacuum dried for 2 hours to give 3.51 g (50%) of sodium 3,3-dimethoxy-2-carbomethoxyprop-1-en-1-oxide as a hydroscopic white powder.

Step B. 2-(4-Trifluoromethyl-phenyl)-pyrimidine-5-carboxylic acid methyl ester

To a solution of 4-Trifluoromethyl-benzamidine acetate salt (1.08 g, 4.35 mmol) in anhydrous dimethyl formamide (10 mL) is added sodium 3,3-dimethoxy-2-carbomethoxyprop-1-en-1-oxide 1.0 g, 5.2 mmol) and the reaction mixture is heated at 100° C. under nitrogen. The reaction is monitored by HPLC, and upon complete consumption of the amidine, is cooled to room temperature. Water (30 mL) is added, and the product precipitated out of solution. The solids are collected by filtration, washed with water (5 mL) and vacuum dried to yield 1.09 g of 2-(4-trifluoromethyl-phenyl)-)-pyrimidine-5-carboxylic acid methoxy-methyl-amide.

Step C. 2-(4-Trifluoromethyl-phenyl)-pyrimidine-5-carboxylic acid methoxy-methyl-amide 2-(4-Trifluoromethyl-phenyl)-pyrimidine-5-carboxylic acid methyl ester (5.6 g, 19.84 mmol) is dissolved into anhydrous tetrahydrofuran (THF) (100 mL) and then cooled to −30° C. while stirring under nitrogen. N,O-dimethylhydroxylamine hydrochloride (3.12 g, 32.0 mmol) is then added to the solution in one portion. Isopropyl magnesium chloride (30 mL, 2M in THF, 60 mmol) is slowly added to the cooled suspension over 1 h. After complete consumption of starting material, then 30% solution of ammonium chloride is added with stirring: The reaction is diluted with diethyl ether and extracted. The organic layer is collected and washed with cold water (2×) and brine. The solution is then dried over anhydrous sodium sulfate, filtered, and concentrated. The 2-(4-trifluoromethyl-phenyl)-pyrimidine-5-carboxylic acid methoxy-methyl-amide (2.46 g, 7.936 mmol) is obtained in pure form after flash column chromatography.

Step D. 1-[2-(4-Trifluoromethyl-phenyl)-pyrimidin-5-yl]-heptan-1-one 2-(4-Trifluoromethyl-phenyl)-pyrimidine-5-carboxylic acid methoxy-methyl-amide (2.46 g, 7.936 mmol) is suspended in anhydrous tetrahydrofuran (40 mL), and cooled to 0° C. with stirring under nitrogen. N-hexyl magnesium bromide (8.0 mL, 2.0 M in diethyl ether, 16 mmol) is slowly added to the reaction over 1 h. The reaction is allowed to warm slowly to room temperature and monitored by TLC. Upon complete consumption of starting material, the reaction is carefully neutralized with 1N hydrochloric acid, extracted with diethyl ether, washed, dried, and concentrated. The 1-[2-(4-Trifluoromethyl-phenyl)-pyrimidin-5-yl]-heptan-1-one (1.47 g, 4.36 mmol) is obtained in pure form after flash column chromatography.

Step E. racemic 1-[2-(4-Trifluoromethyl-phenyl)-pyrimidin-5-yl]-heptan-1-ol

1-[2-(4-Trifluoromethyl-phenyl)-pyrimidin-5-yl]-heptan-1-one (1.47 g, 4.36 mmol) is dissolved in ethanol and cooled to 0° C. while stirring under nitrogen. To the flask is added sodium borohydride (165 mg, 4.36 mmol), and the reaction is kept at 0° C. for 1 h., then slowly warmed to room temperature. The reaction is monitored by HPLC. Upon complete consumption of starting material, the reaction is carefully quenched with water, the ethanol removed by rotary evaporator, and extracted with diethyl ether, washed, dried, and concentrated. The title compound is used in the next step without further purification.

Step F. racemic 3-(4-{1-[2-(4-Trifluoromethyl-phenyl)-pyrimidin-5-yl]-heptyloxy}-benzoylamino)-propionic acid A solution of 3-(4-hydroxy-benzoylamino)-propionic acid methyl ester (1.17 g, 5.25 mmol) and 1-[2-(4-trifluoromethyl-phenyl)-pyrimidin-5-yl]-heptan-1-ol (1.42 g, 4.2 mmol) in toluene (20.0 mL) is degassed and filled with nitrogen for 3 times.

Tributylphosphine (1.6 mL, 6.30 mmol) is added to the reaction mixture under nitrogen at 0° C., followed by addition of 1,1'-(azodicarbonyl)-dipiperidine (1.59 g, 6.30 mmol). The reaction mixture is allowed to warm to room temperature and stirred over night, the mixture is loaded on silica gel column. Chromatography gives the title compound (912 mg).

Step G. (R,S)-3-(4-{1-[2-(4-Trifluoromethyl-phenyl)-pyrimidin-5-yl]-heptyloxy}-benzoylamino)-propionic acid 3-(4-{1-[2-(4-Trifluoromethyl-phenyl)-pyrimidin-5-yl]-heptyloxy}-benzoylamino)-propionic acid methyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 528.21 (M$^+$−1), the structure is also confirmed by proton NMR.

The following compounds are made in a manner substantially similar to Example 64:

Example 65

(R,S)-3-(4-{4,4,4-Trifluoro-1-[2-(4-trifluoromethyl-phenyl)-pyrimidin-5-yl]-butoxy}-benzoylamino)-propionic acid

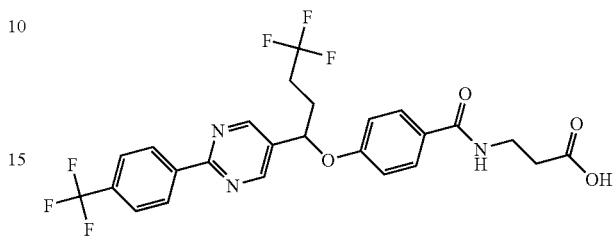

MS (ES): 540.1 [M+H]$^-$, the structure is also confirmed by proton NMR.

The following enantiomeric compounds are obtained by similar chiral separation techniques described herein, using Chiralcel OD column (4.6×250 mm), Chiralpak AD column (4.6×150 mm), or using Chiralcel OJ column (4.6×250 mm):

Example 66

3-(4-{1-[2-(4-Trifluoromethyl-phenyl)-pyrimidin-5-yl]-heptyloxy}-benzoylamino)-propionic acid, Isomer 1

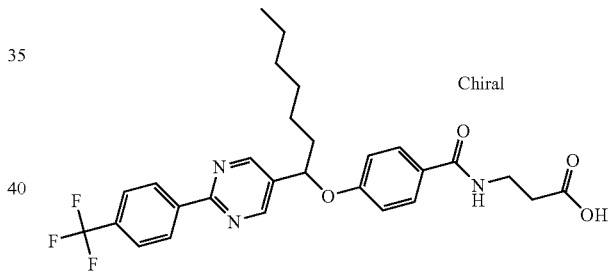

MS (ES): 528.19 [M+H]$^-$, the structure is also confirmed by proton NMR.

Example 67

3-(4-{1-[2-(4-Trifluoromethyl-phenyl)-pyrimidin-5-yl]-heptyloxy}-benzoylamino)-propionic acid, isomer 2

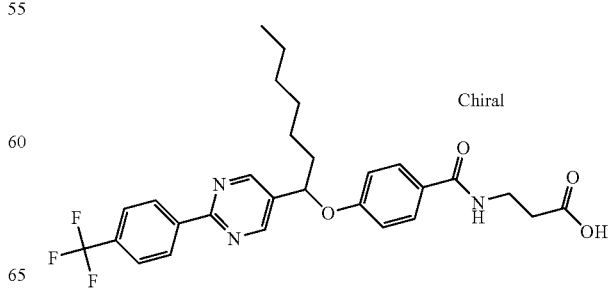

Example 68

3-(4-{4,4,4-Trifluoro-1-[2-(4-trifluoromethyl-phenyl)-pyrimidin-5-yl]-butoxy}-benzoylamino)-propionic acid, isomer 1

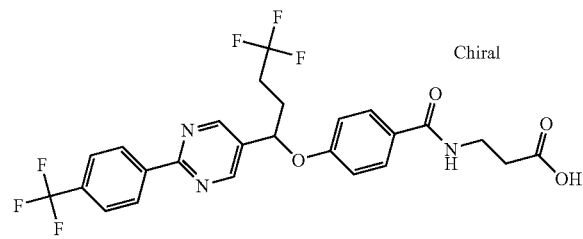

MS (ES): 540.1 [M+H]⁻, the structure is also confirmed by proton NMR.

Example 69

3-(4-{4,4,4-Trifluoro-1-[2-(4-trifluoromethyl-phenyl)-pyrimidin-5-yl]-butoxy}-benzoylamino)-propionic acid, Isomer 2

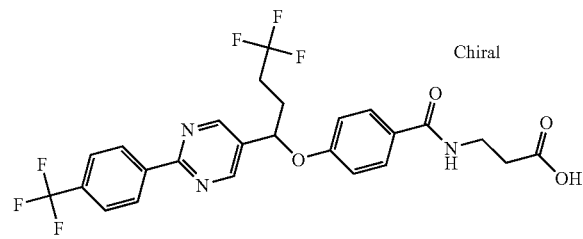

MS (ES): 541.4 [M+H]⁻, the structure is also confirmed by proton NMR.

Example 70

3-{4-[2-Cyclohexyl-1-(4'-trifluoromethyl-biphenyl-4-yl)-ethoxy]-benzoylamino}-propionic acid, Isomer 1

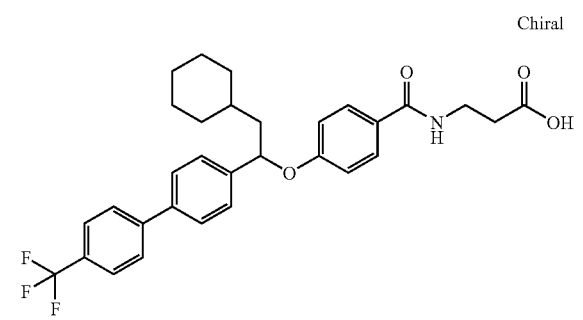

To a mixture of (±)-3-{4-[2-cyclohexyl-1-(4'-trifluoromethyl-biphenyl-4-yl)-ethoxy]-benzoylamino}-propionic acid tert-butyl ester (Isomer 1) (0.0999, 0.168 mmol) in THF (1.7 mL) is added LiOH (1 N aqueous, 1.7 mL) and stirred at 70° C. overnight. The reaction mixture is acidified with 1N HCl (2.0 mL) and extracted with EtOAc (3×10 mL). Combined organic extracts are dried over MgSO₄, filtered, and conc. to provide 3-{4-[2-cyclohexyl-1-(4'-trifluoromethyl-biphenyl-4-yl)-ethoxy]-benzoylamino}-propionic acid (Isomer 1) (0.0801 g, 88%) as a white solid. MS (ES): 540.0 [M+H]⁺.

Example 71

3-{4-[2-Cyclohexyl-1-(4'-trifluoromethyl-biphenyl-4-yl)-ethoxy]-benzoylamino}-propionic acid, Isomer 2

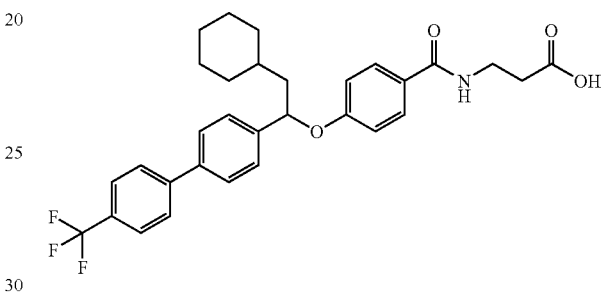

To a mixture of (±)-3-{4-[2-cyclohexyl-1-(4'-trifluoromethyl-biphenyl-4-yl)-ethoxy]-benzoylamino}-propionic acid tert-butyl ester (Isomer 2) (0.0865, 0.145 mmol) in THF (1.5 mL) is added LiOH (1 N aqueous, 1.4 mL) and stirred at 70° C. overnight. The reaction mixture is acidified with 1N HCl (1.5 mL) and extracted with EtOAc (3×10 mL). Combined organic extracts are dried over MgSO₄, filtered, and conc. to provide 3-{4-[2-cyclohexyl-1-(4'-trifluoromethyl-biphenyl-4-yl)-ethoxy]-benzoylamino}-propionic acid (Isomer 2) (0.0706 g, 90%) as a white solid. MS (ES): 540.0 [M+H]⁺.

Example 72

(±)-3-{4-[2-Cyclohexyl-1-(4'-trifluoromethyl-biphenyl-4-yl)-ethoxy]-benzoylamino}-propionic acid

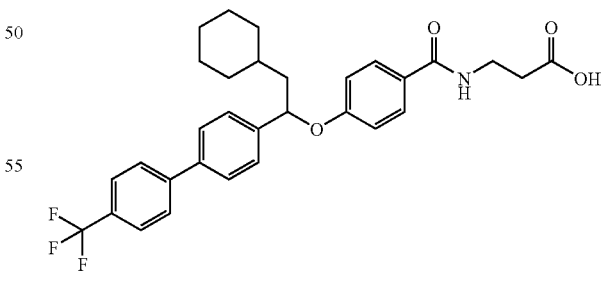

Step A. (R,S)-3-{4-[2-cyclohexyl-1-(4'-trifluoromethyl-biphenyl-4-yl)-ethoxy]-benzoylamino}-propionic acid methyl ester A solution of (±)-2-cyclohexyl-1-(4'-trifluoromethyl-biphenyl-4-yl)-ethanol (0.184 g, 0.527 mmol), 3-(4-hydroxybenzoylamino)-propionic acid methyl ester (0.136 g, 0.608 mmol), and triphenylphosphine (0.208 g, 0.791 mmol) in toluene (8.0 mL) is treated with 1,1'-(azodicarbonyl)dipiperidine (ADDP, 0.206 g, 0.817 mmol) and stirred overnight. The reaction mixture is filtered through Celite® diluted with EtOAc, washed with water (2×), brine (1×), dried over MgSO$_4$, filtered, and conc. The residue is loaded onto silica gel and eluted with hexanes using a gradient of 25% EtOAc to 100% EtOAc giving (±)-3-{4-[2-cyclohexyl-1-(4'-trifluoromethyl-biphenyl-4-yl)-ethoxy]-benzoylamino}-propionic acid methyl ester (0.091 g, 31%) as a white foam. MS (ES): 554.0 [M+H]$^+$.

Step B. (R,S)-3-{4-[2-cyclohexyl-1-(4'-trifluoromethyl-biphenyl-4-yl)-ethoxy]-benzoylamino}-propionic acid To a mixture of (±)-3-{4-[2-cyclohexyl-1-(4'-trifluoromethyl-biphenyl-4-yl)-ethoxy]-benzoylamino}-propionic acid methyl ester (0.0834, 0.151 mmol) in THF (1.0 mL) is added LiOH (1 N aqueous, 0.4 mL) and stirred at RT for 1 h. The reaction mixture is acidified with 1N HCl (0.5 mL) and extracted with EtOAc (3×5 mL). Combined organic extracts are dried over MgSO$_4$, filtered, and conc. to provide (±)-3-{4-[2-cyclohexyl-1-(4'-trifluoromethyl-biphenyl-4-yl)-ethoxy]-benzoylamino}-propionic acid (0.0814 g, 71%) as a white solid. MS (ES): 540.3 [M+H]$^+$.

The following compounds are made in a manner substantially similar to Example 72.

Example 73

(R,S)-3-[4-(4'-Trifluoromethyl-biphenyl-4-yl-methoxy)-benzoylamino]-propionic acid

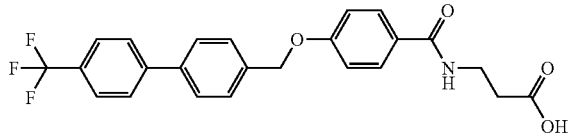

MS (ES): 442.2 [M–H]$^-$.

Example 74

(R,S)-3-{3-Methyl-4-[1-(4'-trifluoromethyl-biphenyl-4-yl)-propoxy]-benzoylamino}-propionic acid

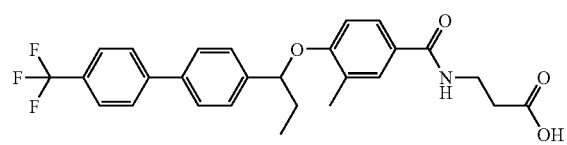

MS (ES): 484.3 [M–H]$^-$.

Example 75

(R,S)-3-{3-Allyl-4-[1-(4'-trifluoromethyl-biphenyl-4-yl)-propoxy]-benzoylamino}-propionic acid

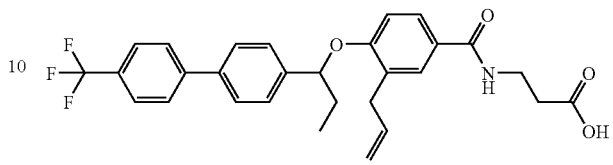

MS (ES): 510.3 [M–H]$^-$.

Example 76

(R,S)-3-{3-tert-Butyl-4-[1-(4'-trifluoromethyl-biphenyl-4-yl)-propoxy]-benzoylamino}-propionic acid

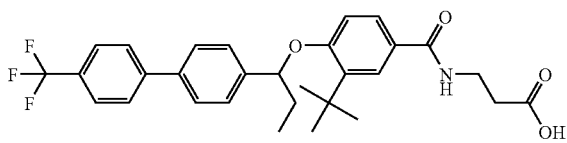

MS (ES): 526.3 [M–H]$^-$.

Example 77

(±)-3-({4-[2-Cyclohexyl-1-(4'-trifluoromethyl-biphenyl-4-yl)-ethoxy]-benzoyl}-methyl-amino)-propionic acid

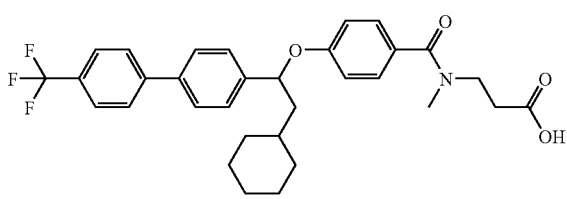

Step A. (R,S)-3-({4-[2-cyclohexyl-1-(4'-trifluoromethyl-biphenyl-4-yl)-ethoxy]-benzoyl}-methyl-amino)-propionic acid tert-butyl ester A solution of (±)-3-{4-[2-cyclohexyl-1-(4'-trifluoromethyl-biphenyl-4-yl)-ethoxy]-benzoylamino}-propionic acid tert-butyl ester (0.0910 g, 0.153 mmol) in dimethylformamide (1.0 mL) at 0° C. was treated with NaH (1 small spatula tip). After 25 min., MeI (0.0240 mL, 0.385 mmol) is added and the reaction is stirred for 1 h. The reaction mixture is quenched with saturated NH$_4$Cl (aq) (2 μL) and extracted with EtOAc (3×10 mL). Combined extracts are washed with brine (1×), dried over MgSO$_4$, filtered, and conc. The residue is loaded onto silica gel and eluted with hexanes using a gradient of 10% EtOAc to 60% EtOAc giving (±)-3-({4-[2-cyclohexyl-1-(4'-trifluoromethyl-biphenyl-4-yl)-ethoxy]- benzoyl}-methyl-amino)-propionic acid tert-butyl ester (7.4 mg, 8%) as a clear syrup. MS (ES): 554.0 [M+H-(t-Bu)]+.

Step B. (R,S)-3-({4-[2-cyclohexyl-1-(4'-trifluoromethyl-biphenyl-4-yl)-ethoxy]-benzoyl}-methyl-amino)-propionic acid To a mixture of (±)-3-({4-[2-cyclohexyl-1-(4'-trifluoromethyl-biphenyl-4-yl)-ethoxy]-benzoyl}-methyl-amino)-propionic acid tert-butyl ester (7.4 mg, 0.012 mmol) in THF (0.5 mL) is added LiOH (1 N aqueous, 0.5 mL) and stirred at 70° C. overnight. The reaction mixture is acidified with 1N HCl (1.0 mL), diluted with water, and extracted with EtOAc (3×5 mL). Combined organic extracts are dried over MgSO₄, filtered, and conc. to provide (±)-3-({4-[2-cyclohexyl-1-(4'-trifluoromethyl-biphenyl-4-yl)-ethoxy]-benzoyl}-methyl-amino)-propionic acid (4.6 mg, 68%) as a clear syrup. MS (ES): 554.2 [M+H]+.

Example 78

(R,S)-3-{4-[3-Ethyl-1-(4'-trifluoromethyl-biphenyl-4-yl)-hexyloxy]-benzoylamino}-2-hydroxy-propionic acid

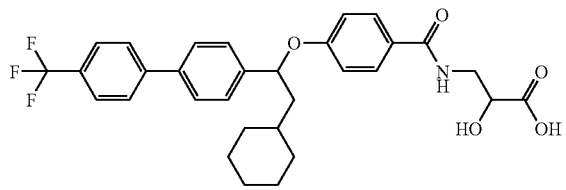

Step A. (R,S)-3-{4-[2-cyclohexyl-1-(4'-trifluoromethyl-biphenyl-4-yl)-ethoxy]-3-methyl-benzoylamino}-2-methyl-propionic acid ethyl ester A solution of (±)-4-[2-cyclohexyl-1-(4'-trifluoromethyl-biphenyl-4-yl)-ethoxy]-benzoic acid (0.0813 g, 0.174 mmol) in THF (1.7 mL) is treated with 2-chloro-4,6-dimethoxy-[1,3,5]triazine (CDMT, 0.0338 g, 0.193 mmol) and N-methyl morpholine (NMM, 0.020 mL, 0.27 mmol). The mixture is added to a flask containing (±)-3-amino-2-hydroxy-propionic acid ethyl ester (0.0465 g, 0.274 mmol). Additional NMM (0.030 mL, 0.273 mmol) and H₂O (0.4 mL) are added and the reaction is stirred overnight. The reaction mixture is dissolved in EtOAc (10 mL) and washed with 0.1 N HCl (2×10 mL), ph=7 phosphate buffer (1×), brine (1×), dried over MgSO₄, filtered, and conc. The residue is loaded onto silica gel and eluted with hexanes using a gradient of 10% EtOAc to 60% EtOAc giving (±)-3-{4-[2-cyclohexyl-1-(4'-trifluoromethyl-biphenyl-4-yl)-ethoxy]-3-methyl-benzoylamino}-2-methyl-propionic acid ethyl ester (0.0568 g, 56%) as a white foam. MS (ES): 582.3 [M−H]−.

Step B. (R,S)-3-{4-[2-cyclohexyl-1-(4'-trifluoromethyl-biphenyl-4-yl)-ethoxy]-benzoylamino}-2-hydroxy-propionic acid To a mixture of (±)-3-{4-[2-cyclohexyl-1-(4'-trifluoromethyl-biphenyl-4-yl)-ethoxy]-3-methyl-benzoylamino}-2-methyl-propionic acid ethyl ester (0.0571 g, 0.0978 mmol) in THF (1.0 mL) is added LiOH (1N aqueous, 1.0 mL) and stirred at RT for 4 d. The reaction mixture is acidified with 1N HCl (1.0 mL) and extracted with EtOAc (3×10 mL). Combined organic extracts are dried over Na₂SO₄, filtered, and conc. to provide (±)-3-{4-[2-cyclohexyl-1-(4'-trifluoromethyl-biphenyl-4-yl)-ethoxy]-benzoylamino}-2-hydroxy-propionic acid (0.0474 g, 87%) as a white foam. MS (ES): 554.3 [M−H]−.

The following compounds are made in a manner substantially similar to Example 78.

Example 79

2-(S)-Hydroxy-3-{4-[1-(4'-trifluoromethyl-biphenyl-4-yl)-propoxy]-benzoylamino}-propionic acid

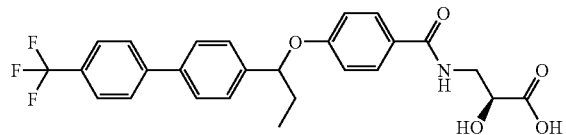

MS (ES): 486.3 [M−H]−.

Example 80

2-(R)-Hydroxy-3-{4-[1-(4'-trifluoromethyl-biphenyl-4-yl)-propoxy]-benzoylamino}-propionic acid

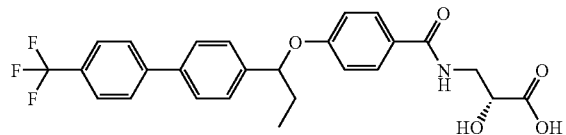

MS (ES): 486.3 [M−H]−.

Example 81

(R,S)-3-{4-[1-(3-Methyl-4'-trifluoromethylbiphenyl-4-yl)ethoxy]benzoyl-amino}propionic acid

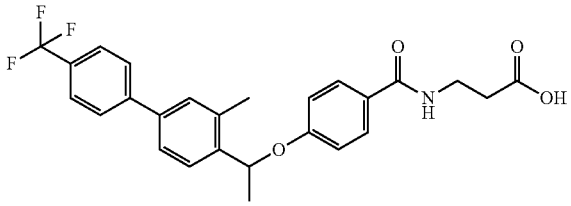

Step A. (R,S)-Methyl (3-{4-[1-(3-methyl-4'-trifluoromethylbiphenyl-4-yl)butoxy]benzoylamino})propionate To a solution of (R,S)-1-(3-methyl-4'-trifluoromethylbiphenyl-4-yl)butan-1-ol (157 mg, 0.56 mmol) in toluene (5.6 mL) is added 1,1'-(azodicarbonyl)dipiperidine (ADDP, 212 mg, 0.84 mmol) at room temperature, followed by the addition of triphenylphosphine (220 mg, 0.84 mmol) and methyl 3-(4-hydroxybenzoylamino)propionate (125 mg, 0.56 mmol). The reaction mixture is stirred overnight. The mixture is treated with water, extracted into dichloromethane, dried and concentrated, then loaded onto silica gel and eluted using hexanes with an ethyl acetate gradient from 0% to 65% giving (R,S)-methyl(3-{4-[1-(3-methyl-4'-trifluoromethylbiphenyl-4-yl)-butoxy]benzoylamino})propionate (114 mg).

Step B. (R,S)-3-{4-[1-(3-Methyl-4'-trifluoromethyl-biphenyl-4-yl)-ethoxy]benzoylamino}propionic acid To a mixture of (R,S)-methyl(3-{4-[1-(3-methyl-4'-trifluoromethylbiphenyl-4-yl)-butoxy]benzoylamino})propionate (110 mg, 0.227 mmol) in methanol (2.27 mL) is added sodium hydroxide (5 N aqueous, 0.228 mL) at room temperature, and stirred overnight. The reaction mixture is acidified by 1 N HCl (1.2 mL), resulting in precipitation of the title compound, which was filtered, washed with water, and dried under vacuum (66 mg). MS (ES): 471.9 [M+H]$^+$.

The following compounds are made in a manner substantially similar to Example 81.

Example 82

(R,S)-3-{4-[1-(3-Methyl-4'-trifluoromethylbiphenyl-4-yl)butoxy]benzoyl-amino}propionic acid

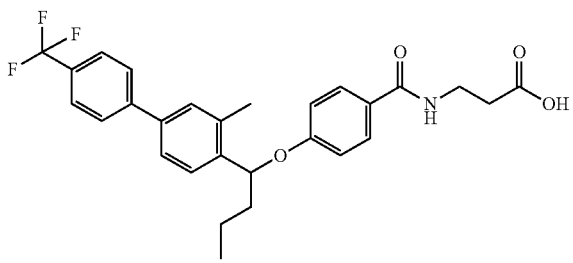

MS (ES): 499.9 [M+H]$^+$.

Example 83

(R,S)-3-{4-[2-Methyl-1-(3-methyl-4'-trifluoromethylbiphenyl-4-yl)propoxy]benzoylamino}-propionic acid

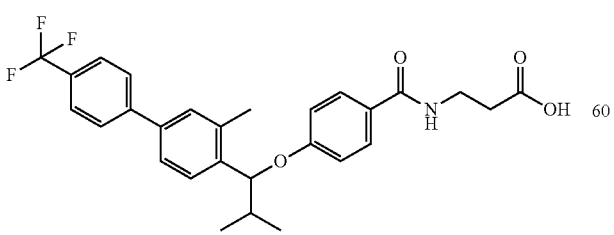

MS (ES): 499.8 [M+H]$^+$.

Example 84

(R,S)-3-{4-[3-Methyl-1-(3-methyl-4'-trifluoromethylbiphenyl-4-yl)butoxy]benzoyl-amino}propionic acid

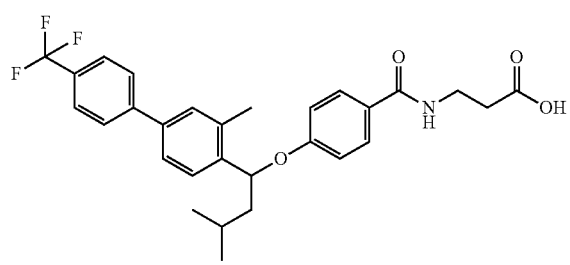

MS (ES): 514.0 [M+H]$^+$.

Example 85

(R,S)-3-{4-[2-Cyclohexyl-1-(2'-trifluoromethylbiphenyl-4-yl)ethoxy]benzoyl-amino}propionic acid

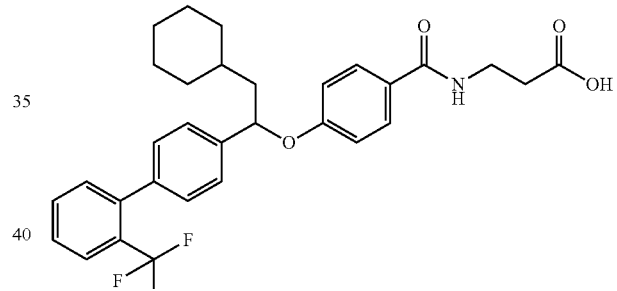

MS (ES): 539.9 [M+H]$^+$.

Example 86

(R,S)-3-{4-[2-Cyclohexyl-1-(3'-trifluoromethylbiphenyl-4-yl)ethoxy]benzoyl-amino}propionic acid

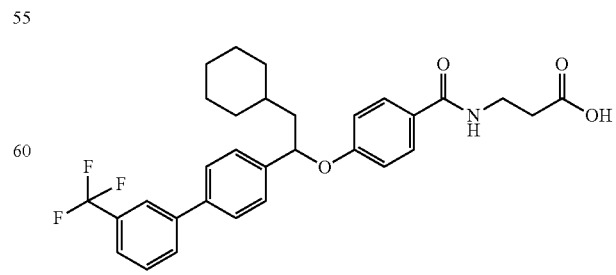

MS (ES): 540.0 [M+H]$^+$.

Example 87

(R,S)-3-{4-[1-(4'-Trifluoromethylbiphenyl-4-yl)ethoxy]benzoylamino}propionic acid

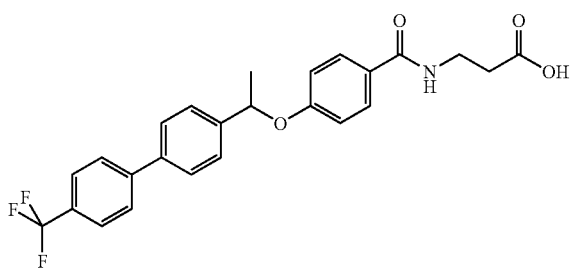

MS (ES): 457.9 [M+H]⁺.

Example 88

(R,S)-3-{4-[1-(4'-Trifluoromethylbiphenyl-4-yl)propoxy]benzoylamino}propionic acid

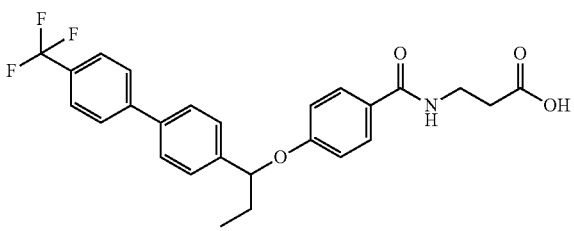

MS (ES): 471.6 [M+H]⁺.

Example 89

(R,S)-3-{4-[2-Methyl-1-(4'-trifluoromethylbiphenyl-4-yl)propoxy]benzoylamino}propionic acid

MS (ES): 486.0 [M+H]⁺.

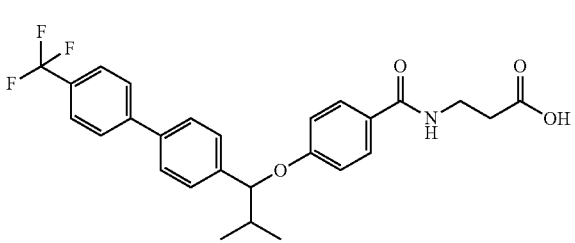

Example 90

(R,S)-3-{4-[3-Methyl-1-(4'-trifluoromethylbiphenyl-4-yl)butoxy]benzoyl-amino}propionic acid

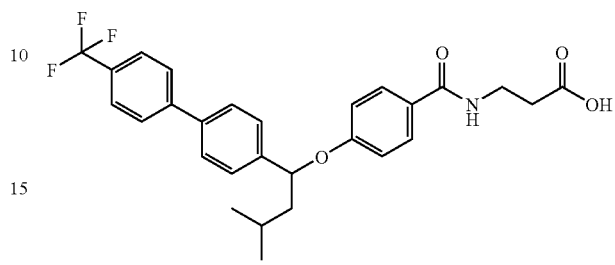

MS (ES): 500.0 [M+H]⁺.

Example 91

(R,S)-3-{4-[1-(4'-Trifluoromethylbiphenyl-4-yl)butoxy]benzoylamino}propionic acid

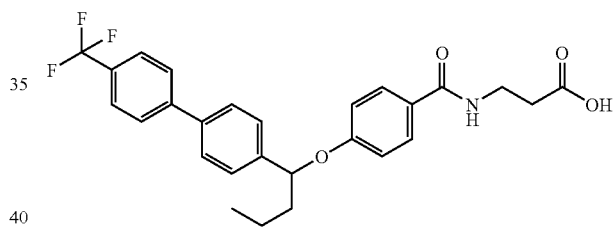

MS (ES): 485.9 [M+H]⁺.

Example 92

(R,S)-3-{4-[1-(4'-Trifluoromethylbiphenyl-4-yl)pentyloxy]benzoylamino}propionic acid

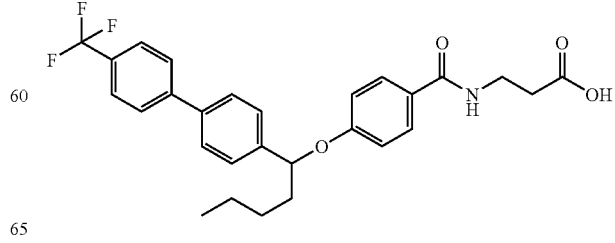

MS (ES): 499.6 [M+H]⁺.

Example 93

(R,S)-3-{4-[1-(4'-Trifluoromethylbiphenyl-4-yl)hexyloxy]benzoylamino}propionic acid

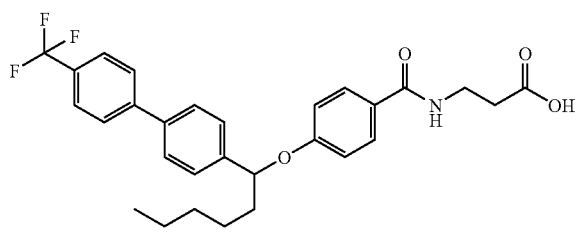

MS (ES): 513.9 [M+H]⁺.

Example 94

(R,S)-3-{4-[1-(4'-Trifluoromethybiphenyl-4-yl)heptyloxy]benzoylamino}propionic acid

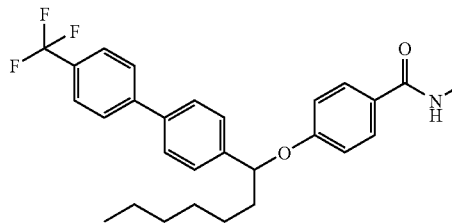

MS (ES): 527.8 [M+H]⁺.

Example 95

(R,S)-3-{4-[1-(4'-Trifluoromethylbiphenyl-4-yl)undecyloxy]benzoylamino}propionic acid

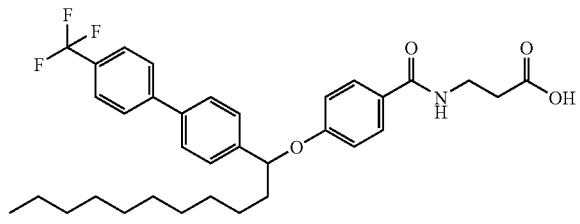

MS (ES): 584.2 [M+H]⁺.

Example 96

3-{4-[Bis-(4'-trifluoromethylbiphenyl-4-yl)methoxy]benzoylamino}propionic acid

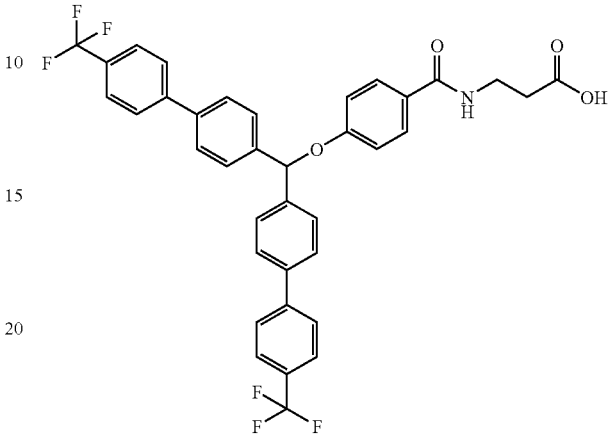

MS (ES): 664.2 [M+H]⁺.

Example 97

(R,S)-3-{4-[Phenyl-(4'-trifluoromethylbiphenyl-4-yl)methoxy]benzoylamino}propionic acid

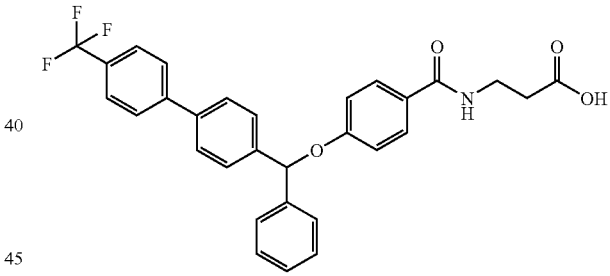

MS (ES): 519.9 [M+H]⁺.

Example 98

3-{4-[1-(4'-Trifluoromethylbiphenyl-4-yl)propoxy]benzoylamino}propionic acid, Isomer 1

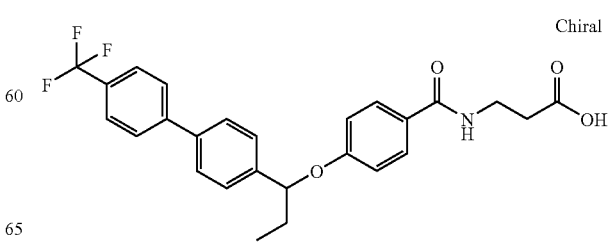

Step A. Ethyl 3-{4-[1-(4'-trifluoromethylbiphenyl-4-yl)propoxy]benzoylamino}propionate (Isomer 1)

(R,S)-Ethyl 3-{4-[1-(4'-trifluoromethylbiphenyl-4-yl)propoxy]benzoylamino}-propionate (224.3 mg) is separated by chiral HPLC (column: Chiralpak AD 4.6×150 mm; eluent: 40% isopropanol in heptane; flow rate: 0.6 mL/min; UV absorbance wavelength: 250 nm) to provide ethyl 3-{4-[1-(4'-trifluoromethylbiphenyl-4-yl)propoxy]benzoylamino}propionate (Isomer 1) (51 mg). HPLC retention time: 8.3 min.

Step B. 3-{4-[1-(4'-Trifluoromethylbiphenyl-4-yl)propoxy]benzoylamino}propionic acid (Isomer 1)

A solution of ethyl 3-{4-[1-(4'-trifluoromethylbiphenyl-4-yl)propoxy]benzoylamino}propionate (Isomer 1) (51 mg, 0.105 mmol) in THF (1.05 mL) is treated with 5 N NaOH (0.106 mL) and shaken at RT overnight. The reaction is neutralized with 1 N HCl (0.53 mL), and extracted into dichloromethane (3×). The combined organic layers are dried and concentrated, giving the title compound (10.1 mg).
MS (ES): 471.9 [M+H]$^+$.

Example 99

3-{4-[1-(4'-Trifluoromethylbiphenyl-4-yl)propoxy]benzoylamino}propionic acid, Isomer 2

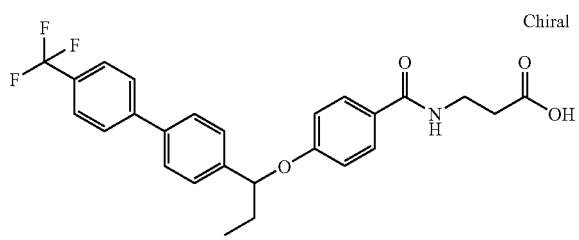

Step A. Ethyl 3-{4-[1-(4'-trifluoromethylbiphenyl-4-yl)propoxy]benzoylamino}propionate, Isomer 2

(R,S)-Ethyl 3-{4-[1-(4'-trifluoromethylbiphenyl-4-yl)propoxy]benzoylamino}propionate (224.3 mg) is separated by chiral HPLC (column: Chiralpak AD 4.6×150 mm; eluent: 40% isopropanol in heptane; flow rate: 0.6 mL/min; UV absorbance wavelength: 250 nm) to provide ethyl 3-{4-[1-(4'-trifluoromethylbiphenyl-4-yl)propoxy]benzoylamino}propionate (Isomer 2) (90 mg). HPLC retention time: 11.45 min.

Step B. 3-{4-[1-(4'-Trifluoromethylbiphenyl-4-yl)propoxy]benzoylamino}propionic acid, Isomer 2

A solution of ethyl 3-{4-[1-(4'-trifluoromethylbiphenyl-4-yl)propoxy]benzoylamino}propionate (Isomer 2) (90 mg, 0.185 mmol) in THF (1.85 mL) is treated with 5 N NaOH (0.186 mL) and shaken at RT overnight. The reaction is neutralized with 1 N HCl (0.93 mL), and extracted into dichloromethane (3×). The combined organic layers are dried and concentrated, giving the title compound (79 mg). MS (ES): 472.1 [M+H]$^+$.

Example 100

(R,S)-3-[4-(1-Biphenyl-4-yl-propoxy)benzoylamino]propionic acid

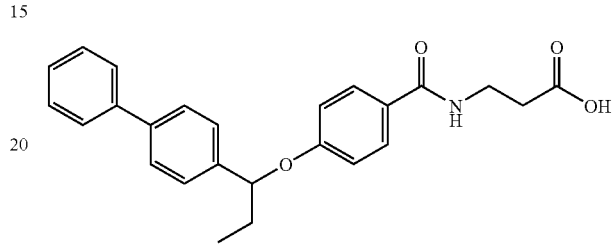

Step A. (R,S)-tert-Butyl-3-[4-(1-biphenyl-4-yl-propoxy)benzoylamino]propionate To a solution of (R,S)-tert-butyl-3-{4-[1-(4-bromophenyl)propoxy]benzoylamino}propionate (329.5 mg, 0.713 mmol) in toluene/ethanol (14.3/14.3 mL) is added phenylboronic acid (96 mg, 0.784 mmol) and tetrakis(triphenylphosphine)palladium (41.2 mg, 0.036 mmol). The mixture is heated to reflux, and 2 N potassium carbonate (0.713 mL) is added. The reaction mixture is heated for 4 h. After cooling to RT, the reaction mixture is partitioned between ethyl acetate and water. The aqueous layer is back-extracted with ethyl acetate, the combined organic layers are dried and concentrated, then loaded onto silica gel and eluted using hexanes with an ethyl acetate gradient from 0% to 70% giving (R,S)-tert-butyl-3-[4-(1-biphenyl-4-yl-propoxy)benzoylamino]propionate (290.4 mg).

Step B. (R,S)-3-[4-(1-Biphenyl-4-yl-propoxy)benzoylamino]propionic acid

A solution of (R,S)-tert-butyl-3-[4-(1-biphenyl-4-yl-propoxy)benzoylamino]propionate (41 mg, 0.089 mmol) in THF (0.89 mL) is treated with 5 N NaOH (0.178 mL) and heated at reflux overnight. The reaction is neutralized with 1 N HCl (0.89 mL), cooled to RT, treated with water, and extracted into dichloromethane. The combined organic layers are dried and concentrated, giving the title compound (35.8 mg). MS (ES): 403.9 [M+H]$^+$.

The following compound is made in a manner substantially similar to Example 100.

Example 101

(R,S)-3-{4-[1-(4'-Trifluoromethoxybiphenyl-4-yl)propoxy]benzoylamino}propionic acid

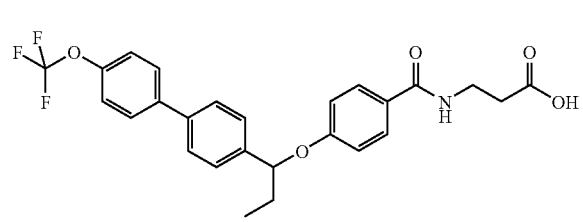

MS (ES): 487.9 [M+H]$^+$.

Example 102

(R,S)-3-{4-[1-(2'-Fluorobiphenyl-4-yl)propoxy]benzoylamino}propionic acid

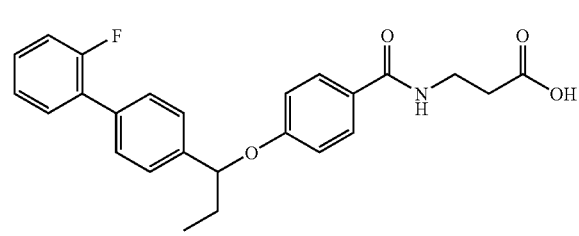

Step A. (R,S)-tert-Butyl-3-{4-[1-(2'-fluorobiphenyl-4-yl)propoxy]benzoylamino}propionate To a solution of (R,S)-tert-butyl-3-{4-[1-(4-bromophenyl)propoxy]benzoylamino}propionate (257.5 mg, 0.556 mmol) in THF (2.22 mL) is added 2-fluorophenylboronic acid (117 mg, 0.834 mmol), potassium fluoride (80 mg, 1.67 mmol), palladium(II) acetate (3.7 mg, 0.017 mmol), and 2-(dicyclohexylphosphino)biphenyl (11.7 mg, 0.033 mmol). The reaction mixture is heated to reflux for 4 h. After cooling to RT, the reaction mixture is partitioned between dichloromethane and water. The aqueous layer is back-extracted with dichloromethane, the combined organic layers are dried and concentrated, then loaded onto silica gel and eluted using hexanes with an ethyl acetate gradient from 0% to 70% giving (R,S)-tert-butyl-3-{4-[1-(2'-fluorobiphenyl-4-yl)propoxy]benzoylamino}propionate (222 mg).

Step B. (R,S)-3-{4-[1-(2'-Fluorobiphenyl-4-yl)propoxy]benzoylamino}propionic acid A solution of (R,S)-tert-butyl-3-{4-[1-(2'-fluorobiphenyl-4-yl)propoxy]benzoylamino}propionate (64.5 mg, 0.135 mmol) in THF (1.35 mL) is treated with 5 N NaOH (0.270 mL) and heated at reflux overnight. The reaction is neutralized with 1 N HCl (1.35 mL), cooled to RT, treated with water, and extracted into dichloromethane. The combined organic layers are dried and concentrated, giving the title compound (28.7 mg). MS (ES): 421.9 [M+H]$^+$.

The following compounds are made in a manner substantially similar to Example 102.

Example 103

(R,S)-3-{4-[1-(2',4'-Difluorobiphenyl-4-yl)propoxy]benzoylamino}propionic acid

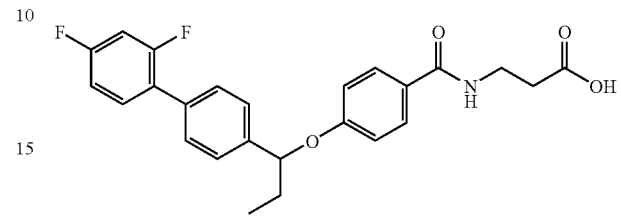

Example 104

(R,S)-3-{4-[1-(2',4'-Bistrifluoromethylbiphenyl-4-yl)propoxy]benzoylamino}-propionic acid

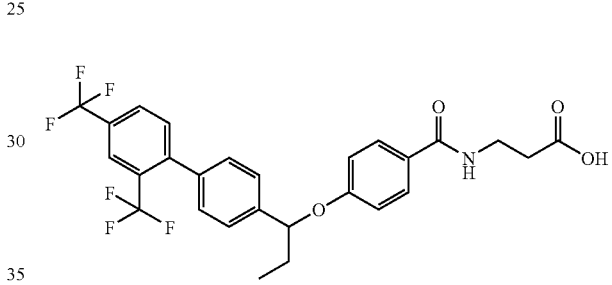

MS (ES): 540.0 [M+H]$^+$.

Example 105

(R,S)-3-(Methyl-{4-[1-(4'-trifluoromethylbiphenyl-4-yl)butoxy]benzoyl}amino) propionic acid

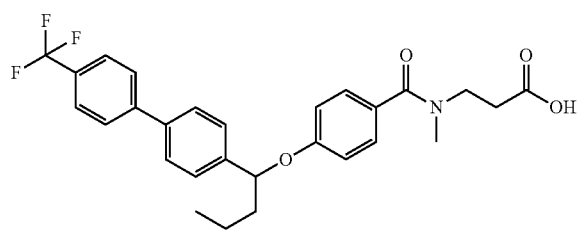

Step A. (R,S)-3-(Methyl-{4-[1-(4'-trifluoromethylbiphenyl-4-yl)butoxy]benzoyl}amino)propionate A solution of (R,S)-3-{4-[1-(4'-trifluoromethylbiphenyl-4-yl)butoxy]benzoylamino}propionic acid (105 mg, 9.217 mmol) in DMF (2.1 mL) under N$_2$ is treated with NaH (60% in mineral oil, 17 mg, 0.434 mmol), and stirred for 15 min. Iodomethane (0.026 mL, 0.434 mmol) is then added to the reaction mixture, which is stirred overnight, quenched by NH$_4$Cl aq., extracted with ethyl acetate, dried and concentrated, then loaded onto silica gel and eluted using hexanes with an ethyl acetate gradient from 0% to 70% giving (R,S)-methyl 3-(methyl-{4-[1-(4'-trifluoromethylbiphenyl-4-yl)butoxy]benzoyl}amino)propionate (17 mg).

Step B. (R,S)-3-(Methyl-{4-[1-(4'-trifluoromethylbiphenyl-4-yl)butoxy]benzoyl}amino)propionic acid To a mixture of (R,S)-methyl 3-(methyl-{4-[1-(4'-trifluoromethylbiphenyl-4-yl) butoxy]benzoyl}-amino)propionate (16 mg, 0.031 mmol) in methanol (1 mL) is added sodium hydroxide (5 N aqueous, 0.032 mL) at room temperature, and stirred overnight. The reaction mixture is acidified by 1 N HCl, extracted into dichloromethane, then dried and concentrated to give the title compound (10.1 mg). MS (ES): 500.0 [M+H]$^+$.

Example 106

(R,S)-3-{4-[1-(4'-Trifluoromethyl-biphenyl-4-yl)-heptyl]-benzoylamino}-propionic acid

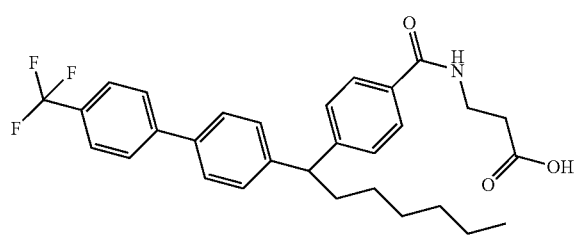

Step A. (R,S)-4-[1-(4-Bromo-phenyl)-1-hydroxy-heptyl]-benzoic acid

To a solution of 4-(4-Bromo-benzoyl)-benzoic acid ethyl ester (2.0 g, 6 mmol) in THF (20 mL) at 0° C. is added hexylmagnesium bromide (2M, 3.3 mL). After stirring at room temperature for 2 hours, it is quenched with saturated ammonium chloride, extracted with EtOAc. The organic is concentrated and purified by column chromatography to give 4-[1-(4-Bromo-phenyl)-1-hydroxy-heptyl]-benzoic acid ethyl ester (0.48 g, 19%), which is taken into methanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving to afford the titled compound (0.47 g).

Step B. (R,S)-3-{4-[1-(4-Bromo-phenyl)-1-hydroxy-heptyl]-benzoylamino}-propionic acid methyl ester To a mixture of 4-[1-(4-bromo-phenyl)-1-hydroxy-heptyl]-benzoic acid (0.47 g, 1.2 mmol) in methylene chloride (12 mL) is added triethyl amine (3.61 mmol, 0.5 mL), followed by the addition of DMAP (5 mg), 3-amino-propionic acid methyl ester HCl salt (252 mg, 1.8 mmol) and EDCI (693 mg, 3.61 mmol). After stirring at room temperature overnight, the reaction mixture is loaded on silica gel column, eluted with hexanes with a gradient from 0% of ethyl acetate to 100% of ethyl acetate to afford the titled compound colorless oil (0.35 g).

Step C. (R,S)-3-{4-[1-Hydroxy-1-(4'-trifluoromethyl-biphenyl-4-yl)-heptyl]-benzoylamino}-propionic acid methyl ester 3-{4-[1-(4-Bromo-phenyl)-1-hydroxy-heptyl]-benzoylamino}-propionic acid methyl ester (350 mg, 0.74 mmol), potassium carbonate (304 mg, 2.2 mmol), 4-trifluoromethylphenyl boronic acid (279 mg, 1.5 mmol) and tetrakis(triphenylphosphine)palladium (86 mg, 0.074 mmol) are place in a flask. After the reaction is purged with N$_2$ for several times, THF/H$_2$O (20 mL/5 mL) is added. The resulting solution is refluxed overnight, loaded on silica gel, eluted with hexane and ethyl acetate to give 3-{4-[1-Hydroxy-1-(4'-trifluoromethyl-biphenyl-4-yl)-heptyl]-benzoylamino}-propionic acid methyl ester (220 mg) as yellow oil.

Step D. 3-{4-[1-(4'-Trifluoromethyl-biphenyl-4-yl)-hept-1-enyl]-benzoylamino}-propionic acid methyl ester

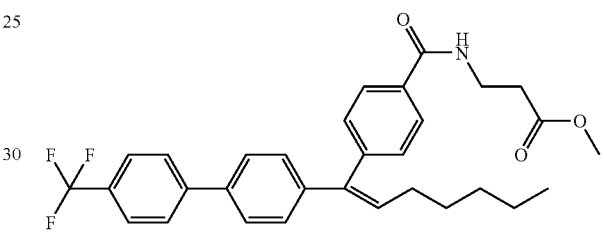

To a solution of 3-{4-[1-Hydroxy-1-(4'-trifluoromethyl-biphenyl-4-yl)-heptyl]-benzoylamino}-propionic acid methyl ester (150 mg, 0.28 mmol) in dichlormethane (10 mL) is added TFA (160 mg, 1.4 mmol) dropwise, followed by the addition of triethylsilane (161 mg, 1.4 mmol). After 2 h, the reaction is quenched by 1N HCl, extracted with ethyl acetate, dried, concentrated, and purified by column chromatography to afford the titled compound (130 mg).

Step E. (R,S)-3-{4-[1-(4'-Trifluoromethyl-biphenyl-4-yl)-heptyl]-benzoylamino}-propionic acid methyl ester To a solution of 3-{4-[1-(4'-Trifluoromethyl-biphenyl-4-yl)-hept-1-enyl]-benzoylamino}-propionic acid methyl ester (90 mg) in ethanol (30 mL) is added Pd/C (10 mg, 10%). The system is purged with nitrogen, followed by the introduction of hydrogen (30 PSI). After 2 h, the mixture is filtered through celites, washed methanol, concentrated, and purified by column chromatography to afford the titled compound (90 mg).

Step F. (R,S)-3-{4-[1-(4'-Trifluoromethyl-biphenyl-4-yl)-heptyl]-benzoylamino}-propionic acid 3-{4-[1-(4'-Trifluoromethyl-biphenyl-4-yl)-heptyl]-benzoylamino}-propionic acid methyl ester (90 mg) is taken into MeOH (2 mL), treated with NaOH (5N, 0.5 mL) for 5 h. The mixture is concentrated, diluted with ethyl acetate, acidified with 5 N HCl (0.5 mL), extracted with ethyl acetate. The organic layers are dried and concentrated giving to afford the titled compound (89 mg). MS (ES): 510.2 [M+H]⁻.

Example 107

3-{4-[1-(4'-Trifluoromethyl-biphenyl-4-ylmethyl)-propoxy]-benzoylamino}-propionic acid

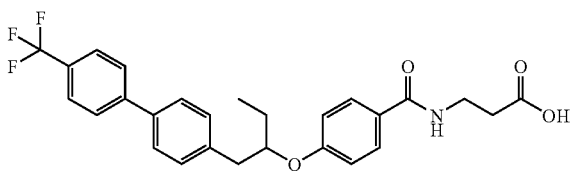

Step A. (4'-Trifluoromethyl-biphenyl-4-yl)-methanol

To a solution of 4'-trifluoromethyl-biphenyl-4-carboxylic acid methyl ester (3.71 g, 13.3 mmol) in tetrahydro-furan (30 mL) is added lithium aluminum hydride (14.6 mmol, 1.0 M in tetrahydro-furan) at 0° C. under inert atmosphere of nitrogen. After the reaction is stirred at 0° C. for 10 minutes following completion of hydride addition, it is quenched with ethyl acetate (10 mL) followed by potassium hydrogen sulfate (1.0 M, 15 mmol) slowly at 0° C., diluted mixture with ethyl ether and filtered. Organic layers are washed with brine, dried over sodium sulfate, filtered, and then concentrated under reduced pressure. Column chromatography (silica gel) with 20-80% ethyl acetate/hexane gradient gives 3.1 g (12.3 mmol, 93%) of title compound.

Step B. 4'-Bromomethyl-4-trifluoromethyl-biphenyl

Phosphorous tribromide (8.67 mmol, 1.0M in dichloromethane) is added to a stirred solution of 4'-trifluoromethyl-biphenyl-4-yl)-methanol (2.08 g, 8.25 mmol) in ethyl ether (40 mL) at 0° C. under inert atmosphere of nitrogen. The reaction is stirred at 0° C. for two hours, quenched at 0° C. with water, diluted mixture with ethyl acetate, washed with water, then brine. Organics are dried over sodium sulfate, filtered and concentrated under reduced pressure. The residue is purified by column (silica gel) in 0-40% ethyl acetate/hexane gradient to give 1.68 g (5.33 mmol, 65%) of title compound.

Step C. (4'-Trifluoromethyl-biphenyl-4-yl)-acetonitrile

A mixture of 4'-bromomethyl-4-trifluoromethyl-biphenyl (0.797 g, 2.53 mmol) and potassium cyanide (0.181 g, 2.78 mmol) in N,N-dimethyl-formamide (6 mL) is stirred for eighty-eight hours at room temperature. The mixture is diluted with ethyl acetate and water. Organic phase is washed with water twice then brine, dried over sodium sulfate, filtered and concentrated. Column chromatography on silica gel with 0-40% ethyl acetate/hexane gradient gives 0.295 g (1.13 mmol, 45%) of title compound.

Step D. (4'-Trifluoromethyl-biphenyl-4-yl)-acetic acid

Concentrated hydrochloric acid (37%, 1 mL) is added to a solution of (4'-trifluoromethyl-biphenyl-4-yl)-acetonitrile (0.290 g, 1.11 mmol) in [1,4]dioxane (2 mL), heated at 110° C. for six hours, cooled to room temperature and adjust pH to 3 using 5.0 N sodium hydroxide, extracted with ethyl acetate three times. Organics are dried over sodium sulfate, filtered and concentrated to provide 0.280 g (11.0 mmol, 90%) of title compound.

Step E. N-Methoxy-N-methyl-2-(4'-trifluoromethyl-biphenyl-4-yl)-acetamide

To a solution of (4'-trifluoromethyl-biphenyl-4-yl)-acetic acid (0.276 g, 0.99 mmol) in tetrahydro-furan (1 mL) is added imidazol-1-yl-pyrazol-1-yl-methanone (0.176 g, 1.1 mmol) and stirred for thirty minutes. A solution of O, N-dimethyl-hydroxylamine hydrochloride (0.107 g, 1.1 mmol) and tri-ethyl-amine (0.15 mL, 1.1 mmol) in N,N-dimethyl-formamide (4 mL) is added to (4'-trifluoromethyl-biphenyl-4-yl)-acetic acid solution and stir sixteen hours, diluted with ethyl acetate, washed with water two times then brine. Organics are dried over sodium sulfate, filtered and concentrated. Column chromatography on silica gel with 0-60% ethyl acetate/hexane gradient gives 0.250 g (0.77 mmol, 78%) of title compound.

Step F. 1-(4'-Trifluoromethyl-biphenyl-4-yl)-butan-2-one

Ethyl magnesium bromide (1.15 mmol, 3.0M in ethyl ether) is added drop-wise to a tetrahydro-furan (3 mL) solution of N-methoxy-N-methyl-2-(4'-trifluoromethyl-biphenyl-4-yl)-acetamide (0.248 g, 0.77 mmol) at −45° C. and stirred for one hour. Gradually raise temperature to −20° C. and stirred for one hour. The reaction is quenched by saturated ammonium chloride solution (1 mL) at 0° C., extracted with ethyl acetate and washed with water and brine. Organics are dried over sodium sulfate, filtered and concentrated. Column chromatography on silica gel with 0-30% ethyl acetate/hexane gradient gives 0.095 g (0.33 mmol, 42%) of the title compound.

Step G. 1-(4'-Trifluoromethyl-biphenyl-4-yl)-butan-2-ol

To an ethanol (2 mL) solution of 1-(4'-trifluoromethyl-biphenyl-4-yl)-butan-2-one (0.093 g, 0.32 mmol) is added sodium borohydride (0.048 g, 1.27 mmol) at 0° C. The reaction mixture is stirred one hour at 0° C., quenched by saturated sodium bicarbonate solution (1 mL) and stirred for five minutes, extracted with ethyl acetate. Organic phase is washed with saturated sodium bicarbonate and brine dried over sodium sulfate, filtered and concentrated to give 0.088 g (0.30 mmol, 94%) of title compound.

Step H. 4-[1-(4'-Trifluoromethyl-biphenyl-4-ylmethyl)-propoxy]-benzoic acid methyl ester 1-(4'-Trifluoromethyl-biphenyl-4-yl)-butan-2-ol (0.088 g, 0.30 mmol) and 4-hydroxy-benzoic acid ethyl ester (0.062 g, 0.37 mmol) are dissolved in toluene (2 mL) under an inert atmosphere of nitrogen. 1,1'-(Azodicarbonyl)dipiperidine (0.114 g, 0.45 mmol) is added, followed by tributyl-phosphane (0.1 mL, 0.45 mmol) at 0° C. The reaction is stirred for eighteen hours at room temperature, diluted with ethyl acetate, filtered and concentrated. Column chromatography on silica gel with 0-40% ethyl acetate/hexane gradient gives 0.050 g (0.11 mmol, 38%) of title compound.

Step I. 4-[1-(4'-Trifluoromethyl-biphenyl-4-ylmethyl)-propoxy]-benzoic acid

To a solution of 4-[1-(4'-trifluoromethyl-biphenyl-4-ylmethyl)-propoxy]-benzoic acid methyl ester (0.048 g, 0.11 mmol) in ethanol (3 mL) is added sodium hydroxide (5.0N, 0.11 mL, 0.54 mmol) and stirred for four hours, acidified with 1.0 N HCl and extracted ethyl acetate three times. Organic layers are dried with sodium sulfate, filtered and concentrated under reduced pressure to provide 0.04 g (0.1 mmol, 89%) of title compound.

Step J. 3-{4-[1-(4'-Trifluoromethyl-biphenyl-4-ylmethyl)-propoxy]-benzoylamino}-propionic acid methyl ester 4-[1-(4'-Trifluoromethyl-biphenyl-4-ylmethyl)-propoxy]-benzoic acid (0.018 g, 0.04 mmol), PyBOP (0.027 g, 0.05 mmol), 3-amino-propionic acid methyl ester hydrochloride (0.011 g, 0.08 mmol), and ethyl-diisopropyl-amine (0.03 mL, 0.18 mmol) are dissolved in N,N-dimethyl-formamide (1 mL) and stirred for sixteen hours. The mixture is diluted with ethyl acetate, washed with water two times then brine. Organic layers are dried over sodium sulfate, filtered and concentrated under reduced pressure. Column chromatography on silica gel with 0-70% ethyl acetate/hexane gradient affords 0.012 g (0.02 mmol, 60%) of title compound.

Step K. 3-{4-[1-(4'-Trifluoromethyl-biphenyl-4-ylmethyl)-propoxy]-benzoylamino}-propionic acid (ME9-A05818-197)

To a solution of 3-{4-[1-(4'-trifluoromethyl-biphenyl-4-ylmethyl)-propoxy]-benzoylamino}-propionic acid methyl ester (0.012 g, 0.02 mmol) in methanol (1 mL) is added sodium hydroxide (5.0N, 0.02 mL, 0.12 mmol) and stirred for three hours. The mixture is acidified with 1.0 N HCl and extracted with ethyl acetate three times. Organic layers are dried over sodium sulfate, filtered and concentrated under reduced pressure provided 0.009 g (0.019 mmol, 77%) of title compound. MS (ESI) m/z 486.2 [M+H]$^+$.

Example 108

(R,S)-3-(4-{1-[6-(4-Trifluoromethyl-phenyl)-pyridin-3-ylmethyl]-propoxy}-benzoylamino)-propionic acid

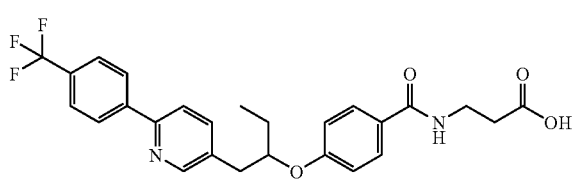

This compound is made in a substantially similar manner to Example 107 using 3-(4-{1-[6-(4-Trifluoromethyl-phenyl)-pyridin-3-ylmethyl]-propoxy}-benzoylamino)-propionic acid as starting material. MS (ESI) m/z 487.3 [M+H]$^+$.

Example 109

(R,S)-3-(4-{2-[6-(4-Trifluoromethyl-phenyl)-pyridin-3-yl]-octyloxy}-benzoylamino)-propionic acid

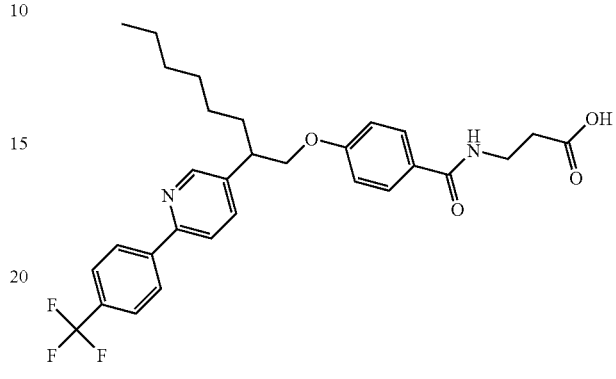

Step A.
2-Chloro-5-(1-methoxymethylene-heptyl)-pyridine (Methoxymethyl)triphenylphosphinium chloride (6.5 g, 20.0 mmol) is suspended in anhydrous toluene (50 mL) and potassium tert-butoxide (2.24 g, 20.0 mmol) carefully added. The solution is allowed to cool and stir at room temperature for 1 h. 1-(6-Chloro-pyridin-3-yl)-heptan-1-one (3.0 g, 13.3 mmol) is then dissolved into anhydrous toluene (50 mL) and added to the reaction mixture by syringe. The reaction is allowed to stir at room temperature for several hours and is monitored by HPLC. Upon complete consumption of starting material, the reaction is carefully quenched with saturated ammonium chloride solution, extracted with diethyl ether, washed, dried, and concentrated. The 2-chloro-5-(1-methoxymethylene-heptyl)-pyridine is purified using flash column chromatography.

Step B. 2-(6-Chloro-pyridin-3-yl)-octanal

2-Chloro-5-(1-methoxymethylene-heptyl)-pyridine is dissolved into anhydrous tetrahydrofuran (20 mL) and concentrated hydrochloric acid (2 mL) are added with stirring under nitrogen. The reaction is heated to 50° C. and monitored by HPLC. Upon complete consumption of starting material, the reaction is carefully neutralized with sodium hydroxide, extracted with diethyl ether, washed, dried, and concentrated. The 2-(6-Chloro-pyridin-3-yl)-octanal (1.02 g, 4.26 mmol), 32% two steps, is obtained in purified form after flash column chromatography.

Step C. 2-(6-Chloro-pyridin-3-yl)-octan-1-ol 2-(6-Chloro-pyridin-3-yl)-octanal (1.02 g, 4.26 mmol) is dissolved into denatured ethanol (20 mL) at room temperature then cooled to 0° C. in an ice bath. Sodium borohydride (0.162 g, 4.26 mmol) is then carefully added in small portions. The reaction is allowed to warm slowly to room temperature and is monitored by HPLC. Upon complete consumption of starting material, the reaction is carefully quenched with water and diluted with ethyl acetate. The ethanol is removed and the residue is extracted with ethyl acetate, washed, dried, and concentrated. The 2-(6-Chloro-pyridin-3-yl)-octan-1-ol (0.856 g, 3.55 mmol), 83%, is obtained in purified form after flash column chromatography.

Step D. 3-{4-[2-(6-Chloro-pyridin-3-yl)-octyloxy]-benzoylamino}-propionic acid tert-butyl ester A solution of 3-(4-hydroxy-benzoylamino)-propionic acid tert-butyl ester (1.17 g, 4.4 mmol) and 2-(6-Chloro-pyridin-3-yl)-octan-1-ol (0.852 g, 3.55 mmol) in toluene (10.0 mL) is degassed and filled with nitrogen for 3 times. Tributylphosphine (1.34 mL, 5.32 mmol) is added to the reaction mixture under nitrogen at 0° C., followed by addition of 1,1'-(azodicarbonyl)-dipiperidine (1.34 g, 5.32 mmol). The reaction mixture is allowed to warm to room temperature and stirred over night, the mixture is loaded on silica gel column. Chromatography gives the title compound (180 mg).

Step E. 3-(4-{2-[6-(4-Trifluoromethyl-phenyl)-pyridin-3-yl]-octyloxy}-benzoylamino)-propionic acid tert-butyl ester 3-{4-[2-(6-Chloro-pyridin-3-yl)-octyloxy]-benzoylamino}-propionic acid tert-butyl ester (180 mg, 0.369 mmol) is dissolved in toluene (2.5 mL), followed by palladium tetrakis triphenylphosphine (23 mg, 0.0197 mmol), 4-trifluoromethyl-phenyl boronic acid (81 mg, 0.43 mmol), and potassium fluoride (46 mg, 0.75 mmol). The reaction is purged with nitrogen and heated to reflux, then the water (2.5 mL) is added. The reaction is monitored by HPLC, and upon completion, allowed to cool to room temperature. The reaction is diluted with EtOAc and then celite added, followed by water. This mixture is then filtered through a pad of celite. The solution is separated in a separatory funnel, then the organic layer is washed with 0.1N sodium hydroxide, water, and brine. The organic layer is dried over anhydrous sodium sulfate, then concentrated. The product is purified by flash column chromatography (110 mg).

Step F. 3-(4-{2-[6-(4-Trifluoromethyl-phenyl)-pyridin-3-yl]-octyloxy}-benzoylamino)-propionic acid 3-(4-{2-[6-(4-Trifluoromethyl-phenyl)-pyridin-3-yl]-octyloxy}-benzoylamino)-propionic acid tert-butyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 541.19 [M+H]⁻, the structure is also confirmed by proton NMR.

Example 110

(R,S)-3-(4-{5,5,5-Trifluoro-2-[6-(4-trifluoromethyl-phenyl)-pyridin-3-yl]-pentyloxy}-benzoylamino)-propionic acid

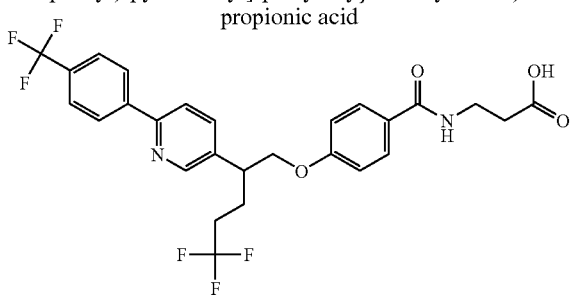

This compounds is made in a manner substantially similar to example 109 using 1-(6-Chloro-pyridin-3-yl)-4,4,4-trifluoro-butan-1-one as starting material in Step A. MS (ES): 553.3 [M+H]⁻, the structure is also confirmed by proton NMR.

Example 111

(R,S)-3-{4-[2-Cyclohexyl-1-(4'-trifluoromethyl-biphenyl-2-yl)-ethoxy]-benzoylamino}-propionic acid

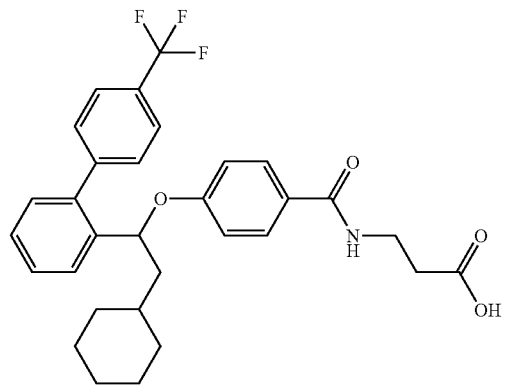

This compound is made in a manner substantially similar to Example 72 using 2-Cyclohexyl-1-(4'-trifluoromethyl-biphenyl-2-yl)-ethanol as starting material in step A. MS (ES): 538.3 [M−H]⁻.

Example 112

(R,S)-3-(4-{1-[4-(5-Trifluoromethyl-pyridin-2-yl)-phenyl]-pentyloxy}-benzoylamino)-propionic acid

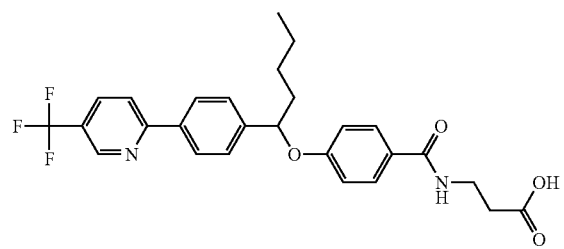

Step A. 1-[4-(5-Trifluoromethyl-pyridin-2-yl)-phenyl]-pentan-1-ol

To a solution of 4-(5-trifluoromethyl-pyridin-2-yl)-benzaldehyde (1.0 g, 3.98 mmol) in andhydrous tetrahydrifuran (THF) (25 mL) that had been cooled to 0° C. in an ice bath is added n-butyl magnesium bromide (8.0 mL, 16.0 mmol) dropwise with stirring under nitrogen. The mixture is allowed to warm slowly to room temperature. The reaction is monitored by HPLC, and upon complete consumption of the aldehyde, quenched with 1N HCl. The mixture is diluted with ethyl ether and water, then extracted. The organic layer is washed with water and brine, dried over anhydrous sodium sulfate and concentrated. The title compound is obtained after column chromatography (1.10 g or 3.20 mmol) at 80% yield.

Step A. 3-(4-{1-[4-(5-Trifluoromethyl-pyridin-2-yl)-phenyl]-pentyloxy}-benzoylamino)-propionic acid methyl ester A solution of 3-(4-hydroxy-benzoylamino)-propionic acid methyl ester (232 mg, 1.04 mmol) and 1-[4-(5-trifluoromethyl-pyridin-2-yl)-phenyl]-pentan-1-ol (258 mg, 0.830 mmol) in toluene (5.0 mL) is degassed and filled with nitrogen for 3 times. Tributyl-phosphine (0.310 mL, 1.50 mmol) is added to the reaction mixture under nitrogen at 0° C., followed by addition of 1,1'-(azodicarbonyl)-dipiperidine (316 mg, 1.50 mmol). The reaction mixture is allowed to warm to room temperature and stirred over night, the mixture is loaded on silica gel column. The 3-(4-{1-[4-(5-trifluoromethyl-pyridin-2-yl)-phenyl]-pentyloxy}-benzoylamino)-propionic acid methyl ester (205 mg, 0.40 mmol), 47%, is obtained in purified form after flash column chromatography.

Step B. 3-(4-{1-[4-(5-Trifluoromethyl-pyridin-2-yl)-phenyl]-pentyloxy}-benzoylamino)-propionic acid 3-(4-{1-[4-(5-trifluoromethyl-pyridin-2-yl)-phenyl]-pentyloxy}-benzoylamino)-propionic acid methyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 499.2 [M+H]⁻, the structure is also confirmed by proton NMR.

Example 113

3-{4-[4-(5-Trifluoromethyl-pyridin-2-yl)-benzyloxy]-benzoylamino}-propionic acid

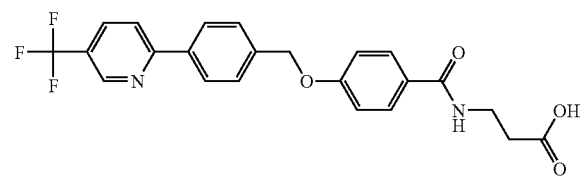

This compound is made in a manner substantially similar to Example 112 using [4-(5-Trifluoromethyl-pyridin-2-yl)-phenyl]-methanol as starting material at Step B. MS (ES): 443.1 [M+H]⁻, the structure is also confirmed by proton NMR.

Example 114

(R,S)-3-(4-{1-[4-(5-Trifluoromethyl-pyridin-2-yl)-phenyl]-butoxy}-benzoylamino)-propionic acid

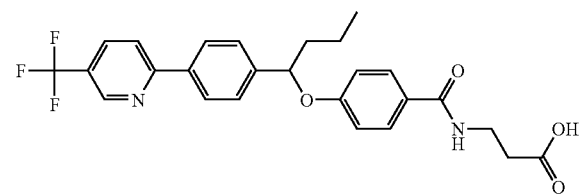

This compound is made in a manner substantially similar to Example 112 using PrMgCl as starting material at Step A. MS (ES): 485.2 [M+H]⁻, the structure is also confirmed by proton NMR.

Example 115

(R,S)-3-(4-{4,4,4-Trifluoro-1-[4-(5-trifluoromethyl-pyridin-2-yl)-phenyl]}-butoxy-benzoylamino)-propionic acid

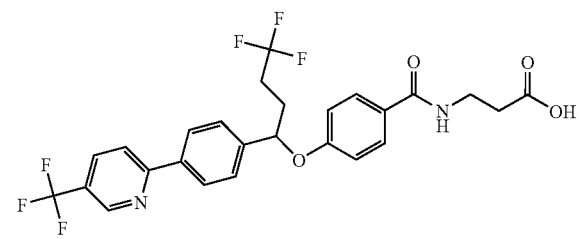

This compound is made in a manner substantially similar to Example 112 using CF₃CH₂CH₂MgBr as starting material at Step A. MS (ES): 539.2 [M+H]⁻, the structure is also confirmed by proton NMR.

Example 116

3-(4-{1-[4-(5-Trifluoromethyl-pyridin-2-yl)-phenyl]-pentyloxy}-benzoylamino)-propionic acid, Isomer 1

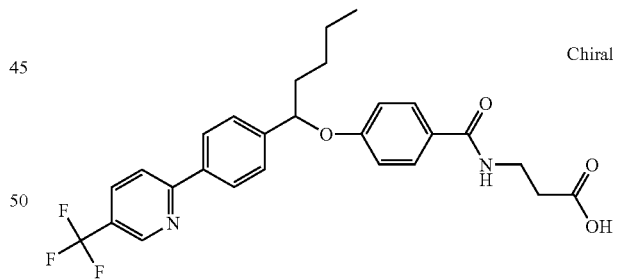

The racemic 3-(4-{1-[4-(5-Trifluoromethyl-pyridin-2-yl)-phenyl]-pentyloxy}-benzoylamino)-propionic acid methyl ester is resolved on a Chiralpak AD-H column (0.46×15 cm) with a flow rate of 0.6 mL/min. and detection at 260 nm. Eluted with isopropyl alcohol in heptane and concentrated the fractions to provide a purified enantiomer ester (isomer 1, >99% ee). Hydrolysis of the purified enantiomer of the ester provided the title compound as a white solid. MS (ES): 501.2 [M+H]⁺, 499.2 [M+H]⁻, the structure is also confirmed by proton NMR.

Example 117

3-(4-{1-[4-(5-Trifluoromethyl-pyridin-2-yl)-phenyl]-pentyloxy}-benzoylamino)-propionic acid, Isomer 2

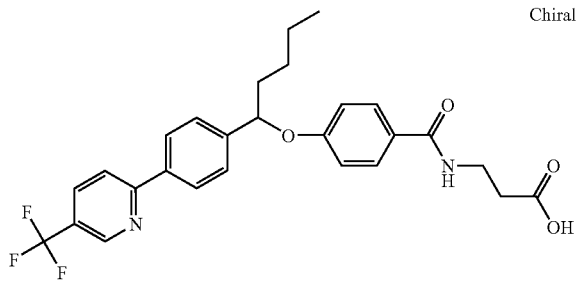

This compound is made by the general method as exemplified in example 116 by resolving racemic 3-(4-{1-[4-(5-Trifluoromethyl-pyridin-2-yl)-phenyl]-pentyloxy}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 2, >99% ee). MS (ES): 499.2 [M+H]⁻, the structure is also confirmed by proton NMR.

Example 118

3-(4-{4,4,4-Trifluoro-1-[4-(5-trifluoromethyl-pyridin-2-yl)-phenyl]-butoxy}-benzoylamino)-propionic acid, Isomer 1

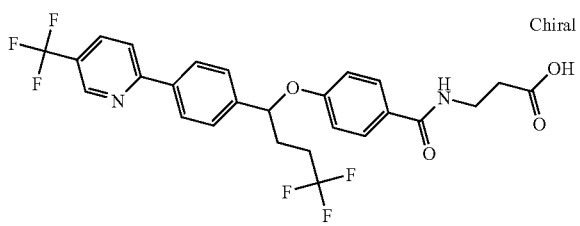

This compound is made by the general method as exemplified in example 116 by resolving racemic 3-(4-{4,4,4-Trifluoro-1-[4-(5-trifluoromethyl-pyridin-2-yl)-phenyl]butoxy}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 1, 100% ee). MS (ES): 539.2 [M+H]⁻, the structure is also confirmed by proton NMR.

Example 119

3-(4-{4,4,4-Trifluoro-1-[4-(5-trifluoromethyl-pyridin-2-yl)-phenyl]-butoxy}-benzoylamino)-propionic acid, Isomer 2

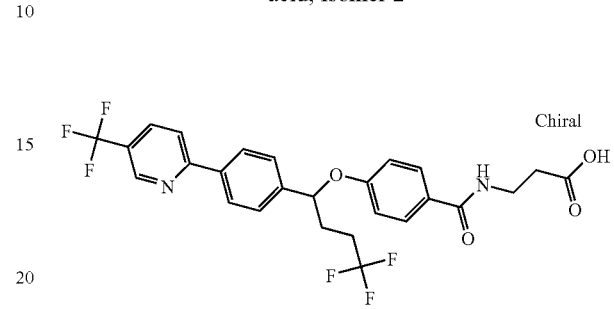

This compound is made by the general method as exemplified in example 64 by resolving racemic 3-(4-{4,4,4-Trifluoro-1-[4-(5-trifluoromethyl-pyridin-2-yl)-phenyl]-butoxy}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 2, 99.4% ee). MS (ES): 539.2 [M+H]⁻, the structure is also confirmed by proton NMR.

Example 120

3-(4-{1-[4-(5-Trifluoromethyl-pyridin-2-yl)-phenyl]-butoxy}-benzoylamino)-propionic acid, Isomer 1

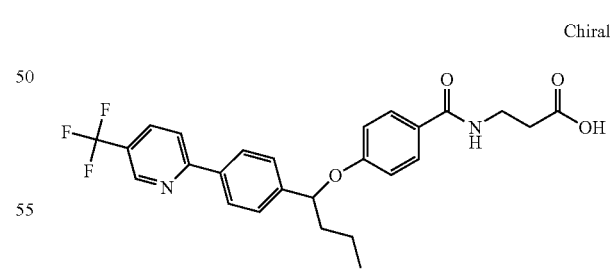

This compound is made by the general method as exemplified in example 116 by resolving racemic 3-(4-{1-[4-(5-Trifluoromethyl-pyridin-2-yl)-phenyl]-butoxy}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 1, 100% ee). MS (ES): 485.2 [M+H]⁻, the structure is also confirmed by proton NMR.

Example 121

3-(4-{1-[4-(5-Trifluoromethyl-pyridin-2-yl)-phenyl]-butoxy}-benzoylamino)-propionic acid, Isomer 2

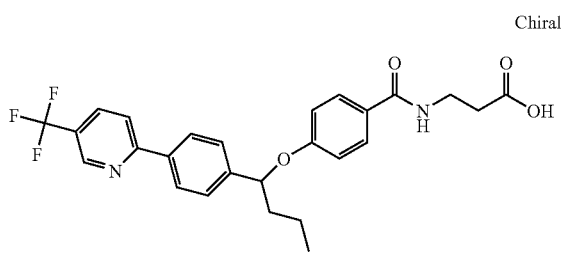

This compound is made by the general method as exemplified in example 116 by resolving racemic 3-(4-{1-[4-(5-Trifluoromethyl-pyridin-2-yl)-phenyl]-butoxy}-benzoylamino)-propionic acid methyl ester on a Chiralpak AD-H column (0.46×15 cm) with a flow rate of 0.6 mL/min. and detection at 260 nm. Eluted with isopropyl alcohol in heptane (isomer 2, 98.6% ee). MS (ES): 485.2 [M+H]⁻, the structure is also confirmed by proton NMR.

Example 122

(R,S)—Cis-3-(4-{6,6,6-Trifluoro-3-[6-(4-trifluoromethyl-phenyl)-pyridin-3-yl]-hex-1-enyl}-benzoylamino)-propionic acid

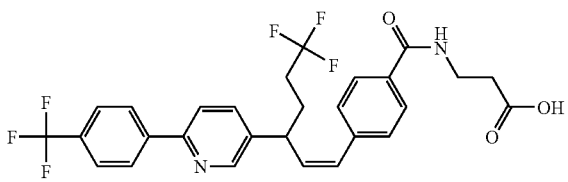

Step A. N-Methoxy-N-methyl-6-(4-trifluoromethyl-phenyl)-nicotinamide 6-(4-Trifluoromethyl-phenyl)-nicotinic acid methyl ester (20 g, 71.2 mmol) is dissolved into anhydrous tetrahydrofuran (TVF) (300 mL) and then cooled to −30° C. while stirring under nitrogen. N,O-dimethylhydroxylamine hydrochloride (10.4 g, 107 mmol) is then added to the solution in one portion. Isopropyl magnesium chloride (107 mL, 2M soln. in THF, 252 mmol) is slowly added to the cooled suspension over 2 h. After complete consumption of starting material, 30% solution of ammonium chloride is added with stirring. The reaction is diluted with diethyl ether, water, and extracted. The organic layer is collected and washed with cold water (2×) and brine. The solution is then dried over anhydrous sodium sulfate, filtered, and concentrated. The N-Methoxy-N-methyl-6-(4-trifluoromethyl-phenyl)-nicotinamide (22 g, 71 mmol) is obtained in purified form after flash column chromatography.

Step B. 4,4,4-Trifluoro-1-[6-(4-trifluoromethyl-phenyl)-pyridin-3-yl]-butan-1-one N-Methoxy-N-methyl-6-(4-trifluoromethyl-phenyl)-nicotinamide (2.0 g, 6.45 mmol) is suspended in anhydrous tetrahydrofuran (25.0 mL), and cooled to 0° C. with stirring under nitrogen. 1,1,1-Trifluoro-butyl magnesium bromide (11.3 mL, 1.14M in tetrahydrofuran, 12.9 mmol) is slowly added to the reaction over 1 h. The reaction is allowed to warm slowly to room temperature and monitored by TLC. Upon complete consumption of starting material, the reaction is carefully acidified with 1N hydrochloric acid, extracted with diethyl ether, washed, dried, and concentrated. The 4,4,4-Trifluoro-1-[6-(4-trifluoromethyl-phenyl)-pyridin-3-yl]-butan-1-one (1.80 g, 5.19 mmol) 80% yield, is used without further purification.

Step C. 5-(4,4,4-Trifluoro-1-methoxymethylene-butyl)-2-(4-trifluoromethyl-phenyl)-pyridine Methoxymethyltriphenylphosphonium chloride (7.4 g, 21.6 mmol) is suspended in anhydrous toluene (25 mL) and potassium tert-butoxide (2.4 g, 21.6 mmol) is added at room temperature in one portion. The mixture is allowed to stir under nitrogen for 1 h. Meanwhile, 4,4,4-Trifluoro-1-[6-(4-trifluoromethyl-phenyl)-pyridin-3-yl]-butan-1-one (5.0 g, 14.4 mmol) is dissolved in another portion of the toluene (25 mL), and kept at room temperature. The mixture is then cooled to 0° C. with ice water, and then the ketone is transferred by cannula. The reaction is allowed to stir at 0° C. for 10 min, then the ice bath is removed. The reaction is allowed to warm to room temperature and monitored by HPLC. Upon complete conversion, the reaction is carefully quenched with saturated ammonium chloride solution, and diluted with ethyl acetate, then extracted. The organic layer is washed with water and brine, dried over anhydrous sodium sulfate, then filtered and concentrated. The 5-(4,4,4-Trifluoro-1-methoxymethylene-butyl)-2-(4-trifluoromethyl-phenyl)-pyridine (4.1 g, 10.9 mmol) is isolated as a mixture of regioisomers after column chromatography, 76% yield.

Step D. 5,5,5-Trifluoro-2-[6-(4-trifluoromethyl-phenyl)-pyridin-3-yl]-pentanal

A solution of 5-(4,4,4-trifluoro-1-methoxymethylene-butyl)-2-(4-trifluoromethyl-phenyl)-pyridine (4.1 g, 10.9 mmol) and tetrahydrofuran (50 mL) is treated with concentrated hydrochloric acid (5 mL) and heated to reflux under nitrogen. The reaction is monitored by HPLC and allowed to cool upon completion. The solution is neutralized with 20% NaOH solution and diluted with diethyl ether. The two phases are separated and the organic layer washed with brine and water. The organic layer is dried over anhydrous sodium sulfate, filtered, and concentrated. Chromatography gives purified 5,5,5-trifluoro-2-[6-(4-trifluoromethyl-phenyl)-pyridin-3-yl]-pentanal (3.6 g, 10 mmol) 79% yield.

Step E. 4-{6,6,6-Trifluoro-3-[6-(4-trifluoromethyl-phenyl)-pyridin-3-yl]-hex-1-enyl}-benzoic acid methyl ester (4-Methoxycarbonyl-benzyl)-triphenyl-phosphonium chloride (6.7 g, 15 mmol) is suspended in anhydrous toluene (25 mL) and potassium tert-butoxide (1.7 g, 15 mmol) is added at room temperature in one portion. The mixture is allowed to stir under nitrogen for 1 h. Meanwhile, 5,5,5-trifluoro-2-[6-(4-trifluoromethyl-phenyl)-pyridin-3-yl]-pentanal (3.61 g, 10.0 mmol) is dissolved in another portion of the toluene (25 mL), and kept at room temperature. The mixture is then cooled to 0° C. with ice water, and then the ketone is transferred by cannula. The reaction is allowed to stir at 0° C. for 10 min, then the ice bath is removed. The reaction is allowed to warm to room temperature and monitored by HPLC. Upon complete conversion, the reaction is carefully quenched with saturated ammonium chloride solution, and diluted with ethyl acetate, then extracted. The organic layer is washed with water and brine, dried over anhydrous sodium sulfate, then filtered and concentrated. The cis and trans 4-{6,6,6-Trifluoro-3-[6-(4-trifluoromethyl-phenyl)-pyridin-3-yl]-hex-1-enyl}-benzoic acid methyl ester (2.0 g, 4.1 mmol) are isolated as pure regioisomers (1:1) after column chromatography, 31% total yield.

Step F. Cis-4-{6,6,6-Trifluoro-3-[6-(4-trifluoromethyl-phenyl)-pyridin-3-yl]-hex-1-enyl}-benzoic acid Cis-4-{6,6,6-Trifluoro-3-[6-(4-trifluoromethyl-phenyl)-pyridin-3-yl]-hex-1-enyl}-benzoic acid methyl ester (1.0 g, 2.0 mmol) is taken into THF (5.0 mL) and treated with NaOH (2.5 mL, 5.0 N), then refluxed under nitrogen. The reaction mixture is neutralized with HCl (2.5 mL, 5.0 N), extracted with ethyl ether, dried over sodium sulfate. Concentration gives the title compound.

Step G. Cis-3-(4-{6,6,6-Trifluoro-3-[6-(4-trifluoromethyl-phenyl)-pyridin-3-yl]-hex-1-enyl}-benzoylamino)-propionic acid methyl ester The cis-4-{6,6,6-Trifluoro-3-[6-(4-trifluoromethyl-phenyl)-pyridin-3-yl]-hex-1-enyl}-benzoic acid (214 mg, 0.45 mmol), chloro-dimethoxy-triazine (CDMT) (81 mg, 0.46 mmol), and 4-methylmorpholine (50 uL, 0.47 mmol) are combined in anhydrous DCM under nitrogen. The reaction is allowed to stir under nitrogen at room temperature overnight. Beta-alanine hydrochloride (68 mg, 0.49 mmol) and 4-methylmorpholine (100 uL, 0.94 mmol) is then added to the reaction mixture, and allowed to stir at room temperature. Some water (<10% volume) is added to help solubility. The reaction is monitored by HPLC, and upon complete consumption of the acid, the reaction is diluted with DCM and water and rinsed with 1N HCl. The organic layer is washed with water and brine, dried over anhydrous sodium sulfate, then filtered and concentrated. The cis-3-(4-{6,6,6-trifluoro-3-[6-(4-trifluoromethyl-phenyl)-pyridin-3-yl]-hex-1-enyl}-benzoylamino)-propionic acid methyl ester (197 mg, 0.35 mmol) is isolated after column chromatography, 78% yield.

Step H. Cis-3-(4-{6,6,6-Trifluoro-3-[6-(4-trifluoromethyl-phenyl)-pyridin-3-yl]-hex-1-enyl}-benzoylamino)-propionic acid Cis-3-(4-{6,6,6-Trifluoro-3-[6-(4-trifluoromethyl-phenyl)-pyridin-3-yl]-hex-1-enyl}-benzoylamino)-propionic acid methyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 549.3 [M+H]⁻, the structure is also confirmed by proton NMR.

Example 123

(R,S)-Trans-3-(4-{6,6,6-Trifluoro-3-[6-(4-trifluoromethyl-phenyl)-pyridin-3-yl]-hex-1-enyl}-benzoylamino)-propionic acid

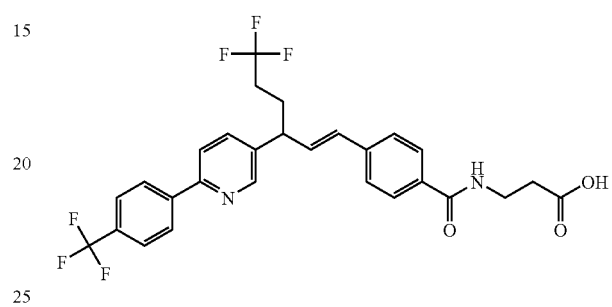

This compound is made in a similar method as example 122 using the trans isomer as starting material at Step F. MS (ES): 549.3 [M+H]⁻, the structure is also confirmed by proton NMR.

Example 124

3-(4-{4,4-Dimethyl-1-[6-(4-trifluoromethyl-phenyl)-pyridin-3-yl]-pentyloxy}-benzoylamino)-butyric acid

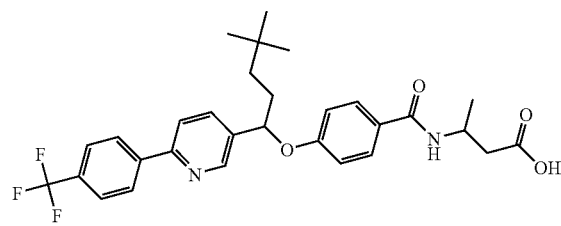

MS (ES): 541.3 [M+H]⁻, the structure is also confirmed by proton NMR.

Step A. 4-{4,4-Dimethyl-1-[6-(4-trifluoromethyl-phenyl)-pyridin-3-yl]-pentyloxy}-benzoic acid methyl ester 4,4-Dimethyl-1-[6-(4-trifluoromethyl-phenyl)-pyridin-3-yl]-pentan-1-ol (231 mg, 0.69 mmol) and methyl 4-hydrxyl benzoate (130 mg, 0.86 mmol) are dissolved into anhydrous toluene (5 μL). The mixture is degassed and filled with nitrogen for 3 times. Tributyl-phosphine (0.250 mL, 1.03 mmol) is added to the reaction mixture under nitrogen at 0° C., followed by addition of 1,1'-(azodicarbonyl)-dipiperidine (259 mg, 1.03 mmol). The reaction is allowed to warm to room temperature and stirred over night, the mixture is loaded on silica gel column. The 4-{4,4-Dimethyl-1-[6-(4-trifluoromethyl-phenyl)-pyridin-3-yl]-pentyloxy}-benzoic acid methyl ester is obtained in pure form after flash column chromatography.

Step B. Chiral Separation

The racemic 4-{4,4-Dimethyl-1-[6-(4-trifluoromethyl-phenyl)-pyridin-3-yl]-pentyloxy}-benzoic acid methyl ester is resolved on a Chiralpak AD-H column (0.46×15 cm) with a flow rate of 0.6 mL/min. and detection at 260 nm. Eluted acetonitrile in 3A alcohol and concentrated the fractions to provide a purified enantiomer ester (isomer 1, >99% ee and isomer 2, >99% ee).

Step C. 4-{4,4-Dimethyl-1-[6-(4-trifluoromethyl-phenyl)-pyridin-3-yl]-pentyloxy}-benzoic acid 4-{4,4-Dimethyl-1-[6-(4-trifluoromethyl-phenyl)-pyridin-3-yl]-pentyloxy}-benzoic acid methyl ester (isomer 2) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound, (180 mg, 0.38 mmol), 55%.

Step D. 3-(4-{4,4-Dimethyl-1-[6-(4-trifluoromethyl-phenyl)-pyridin-3-yl]-pentyloxy}-benzoylamino)-butyric acid methyl ester The 4-{4,4-Dimethyl-1-[6-(4-trifluoromethyl-phenyl)-pyridin-3-yl]-pentyloxy}-benzoic acid (95 mg, 0.21 mmol), chloro-dimethoxy-triazine (CDMT) (37 mg, 0.21 mmol), and 4-methylmorpholine (25 uL, 0.23 mmol) are combined in anhydrous DCM under nitrogen. The reaction is allowed to stir under nitrogen at room temperature overnight. 3-Aminobutyric acid methyl ester (26 mg, 0.23 mmol) and 4-methylmorpholine (50 uL, 0.47 mmol) is then added to the reaction mixture, and allowed to stir at room temperature. Some water (<10% volume) is added to help solubility. The reaction is monitored by HPLC, and upon complete consumption of the acid, the reaction is diluted with DCM and water and rinsed with 1N HCl. The organic layer is washed with water and brine, dried over anhydrous sodium sulfate, then filtered and concentrated. The 3-(4-{4,4-dimethyl-1-[6-(4-trifluoromethyl-phenyl)-pyridin-3-yl]-pentyloxy}-benzoylamino)-butyric acid methyl ester is isolated after column chromatography.

Step E. 3-(4-{4,4-Dimethyl-1-[6-(4-trifluoromethyl-phenyl)-pyridin-3-yl]-pentyloxy}-benzoylamino)-butyric acid 3-(4-{4,4-Dimethyl-1-[6-(4-trifluoromethyl-phenyl)-pyridin-3-yl]-pentyloxy}-benzoylamino)-butyric acid methyl ester are taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound, (163 mg, 0.15 mmol) 72% 2 steps. MS (ES): 541.3 [M+H]⁻, the structure is also confirmed by proton NMR.

Example 125

3-(4-{4,4-Dimethyl-1-[6-(4-trifluoromethyl-phenyl)-pyridin-3-yl]-pentyloxy}-benzoylamino)-butyric acid

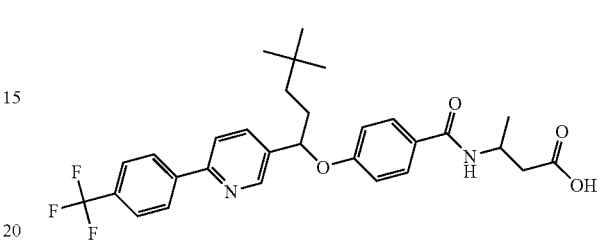

This compound is made in a similar method as example 124 using isomer 1 as starting material at Step C. MS (ES): 541.3 [M+H]⁻, the structure is also confirmed by proton NMR.

Example 126

(R,S)-3-{4-[2-(4'-Trifluoromethylbiphenyl-4-yl)butoxy]benzoylamino}propionic acid

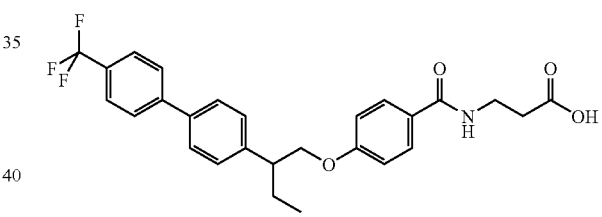

This compound is made in similar manner as example 72 using 2-(4'-trifluoromethylbiphenyl-4-yl)butan-1-ol as starting material in step A. MS (ES): 485.9 [M+H]⁺.

Example 127

(R,S)-3-(4-{1-[5-(3,5-Bis-trifluoromethyl-phenyl)-pyridin-3-yl]-heptyloxy}-benzoylamino)-propionic acid

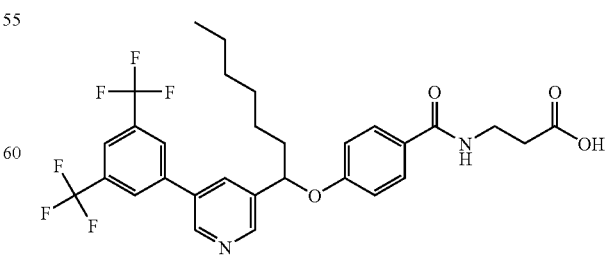

This compound is made in a similar manner as example 25 using 5-bromo-nicotinic acid methyl ester as starting material in step A, n-hexylmagnesium bromide as reagent in step B and 3,5-bistrifluoromethylphenyl boronic acid as reagent in step E. MS (ES): 595.15 [M+H]⁻, the structure is also confirmed by proton NMR.

Example 128

(R,S)-3-(4-{1-[5-(4-Isobutyl-phenyl)-pyridin-3-yl]-heptyloxy}-benzoylamino)-propionic acid

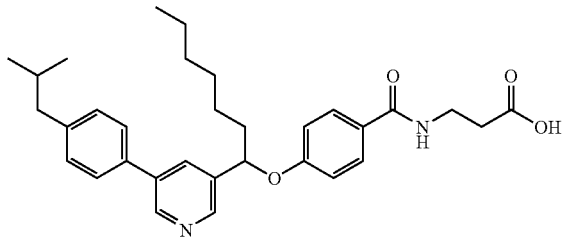

This compound is made in a similar manner as example 24 using 5-bromo-nicotinic acid methyl ester as starting material in Step A, n-hexylmagnesium bromide as reagent in Step B and 4-isobutylphenyl boronic acid as reagent in step E. MS (ES): 515.26 [M+H]⁻, the structure is also confirmed by proton NMR.

Example 129

(R,S)-3-(4-{1-[5-(4-tert-Butyl-phenyl)-pyridin-3-yl]-heptyloxy}-benzoylamino)-propionic acid

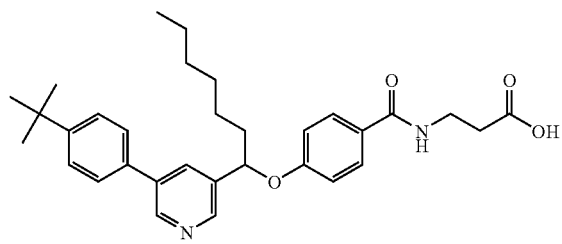

This compound is made in a similar manner as example 25 using 5-bromo-nicotinic acid methyl ester as starting material in Step A, n-hexylmagnesium bromide as reagent in Step B and 4-tert-butylphenyl boronic acid as reagent in step E. MS (ES): 515.27 [M+H]⁻, the structure is also confirmed by proton NMR.

Example 130

(R,S)-3-(4-{1-[5-(4-Ethyl-phenyl)-pyridin-3-yl]-heptyloxy}-benzoylamino)-propionic acid

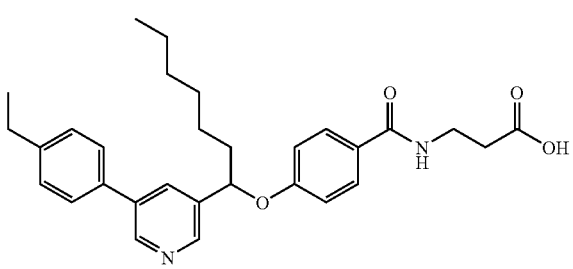

This compound is made in a similar manner as example 25 using 5-bromo-nicotinic acid methyl ester as starting material in Step A, n-hexylmagnesium bromide as reagent in step B, and 4-ethylphenyl boronic acid as reagent in step E. MS (ES): 487.24 [M+H]⁻, the structure is also confirmed by proton NMR.

Example 131

(R,S)-3-{4-[2-Cyclohexyl-1-(4'-trifluoromethyl-biphenyl-3-yl)-ethoxy]-benzoylamino}-propionic acid

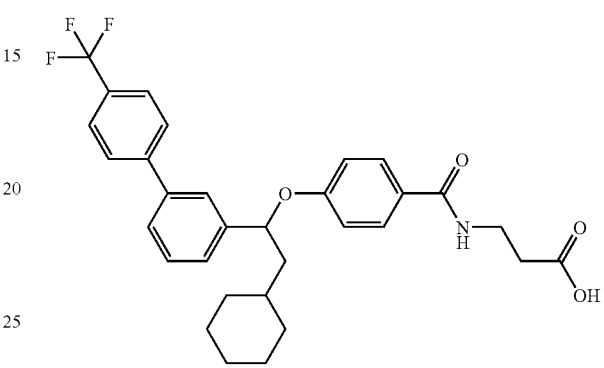

This compound is made in similar manner as example 72 using 2-cyclohexyl-1-(4'-trifluoromethyl-biphenyl-3-yl)-ethanol as starting material in Step A. MS (ES): 538.3 [M−H]⁻.

Example 132

(R,S)-3-{4-[2-Cyclohexyl-1-(3-methyl-4'-trifluoromethyl-biphenyl-4-yl)-ethoxy]-benzoylamino}-propionic acid

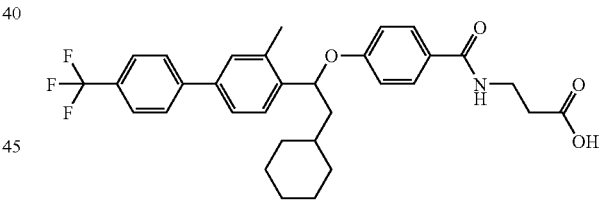

This compound is made in similar manner as example 72 using 2-cyclohexyl-1-(3-methyl-4'-trifluoromethyl-biphenyl-4-yl)-ethanol as starting material in Step A. MS (ES): 552.3 [M−H]⁻.

Example 133

(R,S)-3-(4-{1-[4-(2,3,5,6-Tetramethyl-benzyloxy)-phenyl]-propoxy}-benzoylamino)-propionic acid

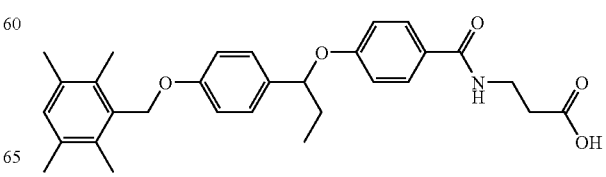

To a solution of Racemic 1-[4-(2,3,5,6-tetramethyl-benzyloxy)-phenyl]-propan-1-ol (596 mg, 2 mmol) in toluene (10 mL) is added 1,1'-(Azodicarbonyl)dipiperidine (ADDP, 756 mg, 3 mmol) at 0° C., followed by the addition of tributylphosphine (0.75 mL, 3 mmol) and methyl 3-(4-Hydroxybenzoylamino)propionate (669 mg, 3 mmol). The reaction mixture is warmed up to room temperature and stirred overnight. The mixture is loaded on silica gel, eluted with hexanes with a gradient from 0% of ethyl acetate to 50% of ethyl acetate giving methyl 3-(4-{1-[4-(2,3,5,6-tetramethyl-benzyloxy)-phenyl]-propoxy}-benzoylamino)-propionic acid ester. The ester product is taken into methanol (2 mL), treated with sodium hydroxide (5N aqueous, 1 mL) for 3 h at room temperature. The mixture is concentrated, diluted with ethyl acetate, acidified with 5 N HCl (1.1 mL), extracted with ethyl acetate. The organic layers are dried and concentrated giving the titled compound (89 mg). MS (ES): 490.29 [M+H]$^+$.

The following compound is made in a manner substantially similar to Example 133:

Example 134

(R,S)-{4-[1-(4-Pentamethylphenylmethoxy-phenyl)-propoxy]-benzoylamino}-propionic acid

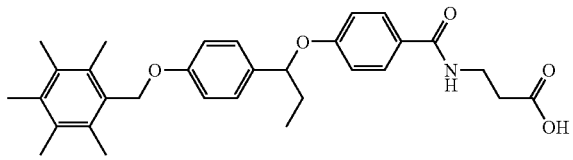

MS (ES): 502.2 [M+H]$^+$.

Example 135

3-(4-{1-[4-(2,3,5,6-Tetramethyl-benzyloxy)-phenyl]-propoxy}-benzoylamino)-propionic acid, Isomer 1

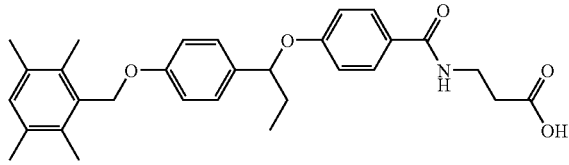

Chiral Separation

The racemic (3-(4-{1-[4-(2,3,5,6-tetramethyl-benzyloxy)-phenyl]-propoxy}-benzoylamino)-propionic acid methyl ester is resolved on a Chiralpak AD column (4.6×150 mm). Eluted with 3A Alcohol/Heptane (15/85) and concentrated the fractions to provide a purified enantiomer ester (isomer 1, 99.8% ee). Hydrolysis of the purified enantiomer of the ester provides the title compound as a white solid. MS (ES): 490.31 [M+H]$^+$.

The following enantiomerically purified compound is obtained by similar chiral separation using Chiralpak AD column (4.6×150 mm):

Example 136

3-(4-{1-[4-(2,3,5,6-Tetramethyl-benzyloxy)-phenyl]-propoxy}-benzoylamino)-propionic acid, Isomer 1

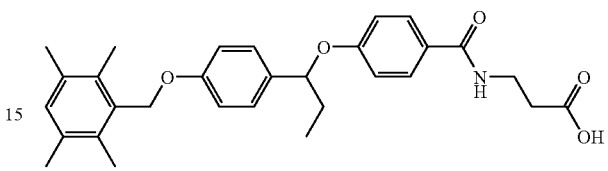

MS (ES): 490.30 [M+H]$^+$.

Example 137

(R,S)-3-(4-{1-[6-(4-Trifluoromethyl-phenoxy)-pyridin-3-yl]-heptyloxy}-benzoylamino)-propionic acid

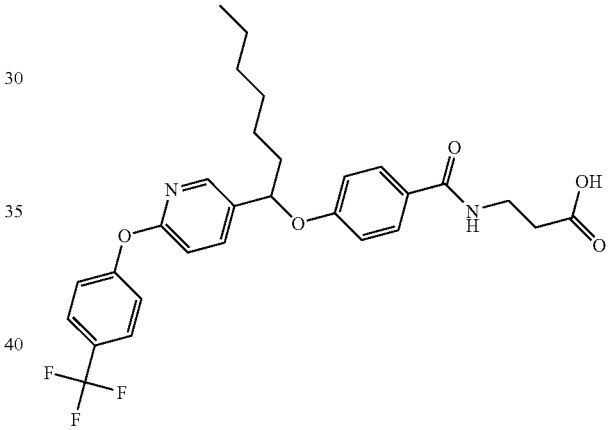

Step A. 1-[6-(4-Trifluoromethyl-phenoxy)-pyridin-3-yl]-heptan-1-one

To a solution of 1-(6-chloro-pyridin-3-yl)-heptan-1-one (2.5 g, 11.1 mmol) in anhydrous 1-methyl-2-pyrrolidinone (NMP) (50 mL) is added ααα-trifluoro creosol (3.6 g, 22.2 mmol) followed by cesium carbonate (7.8 g, 22.2 mmol) with stirring under nitrogen. The mixture is heated to 100° C. under nitrogen. The reaction is monitored by HPLC, and upon complete consumption of the chloride is allowed to cool to room temperature. The mixture is diluted with ethyl acetate and water, then extracted against 0.1N NaOH solution. The organic layer is washed with water and brine, dried over anhydrous sodium sulfate, then concentrated. The title compound is obtained after column chromatography (1.45 g or 37% yield).

Step B. 1-[6-(4-Trifluoromethyl-phenoxy)-pyridin-3-yl]-heptan-1-ol

1-[6-(4-Trifluoromethyl-phenoxy)-pyridin-3-yl]-heptan-1-one (1.45 g, 4.13 mmol) is dissolved into denatured ethanol (20 mL) at room temperature then cooled to 0° C. in an ice bath. Sodium borohydride (0.132 g, 4.13 mmol) is then carefully added in small portions. The reaction is allowed to warm slowly to room temperature and is monitored by HPLC. Upon complete consumption of starting material, the reaction is carefully quenched with water and diluted with ethyl acetate. The ethanol is removed and the residue is extracted with ethyl acetate, washed, dried, and concentrated. The 1-[6-(4-trifluoromethyl-phenoxy)-pyridin-3-yl]-heptan-1-ol (1.29 g, 3.65 mmol, 88%), is obtained in purified form after flash column chromatography.

Step C. 3-(4-{1-[2-(4-Trifluoromethyl-phenyl)-pyrimidin-5-yl]-heptyloxy}-benzoylamino)-propionic acid methyl ester A solution of 3-(4-hydroxy-benzoylamino)-propionic acid methyl ester (140 mg, 0.62 mmol) and 1-[6-(4-trifluoromethyl-phenoxy)-pyridin-3-yl]-heptan-1-ol (175 mg, 0.496 mmol) in toluene (2.0 mL) is degassed and filled with nitrogen for 3 times. Tributyl-phosphine (0.187 mL, 0.744 mmol) is added to the reaction mixture under nitrogen at 0° C., followed by addition of 1,1'-(azodicarbonyl)-dipiperidine (187 mg, 0.744 mmol). The reaction mixture is allowed to warm to room temperature and stirred over night, the mixture is loaded on silica gel column. Chromatography gives the title compound (136 mg).

Step D. (R,S)-3-(4-{(4-tert-Butyl-phenyl)-[6-(4-trifluoromethyl-phenyl)-pyridin-3-yl]-methoxy}-benzoylamino)-propionic acid 3-(4-{1-[2-(4-Trifluoromethyl-phenyl)-pyrimidin-5-yl]-heptyloxy}-benzoylamino)-propionic acid methyl ester (50 mg) is taken into THF (1.0 mL) and treated with NaOH (1.0 mL, 5.0 N), then refluxed under nitrogen. The reaction mixture is neutralized with HCl (1.0 mL, 5.0 N), extracted with ethyl ether, dried over sodium sulfate. Concentration gives the title compound. MS (ES): 543.2 [M+H]⁻, the structure is also confirmed by proton NMR.

The following compounds are made in a manner substantially similar to Example 137:

Example 138

(R,S)-3-{4-[1-(4-Trifluoromethyl-3,4,5,6-tetrahydro-2H-[1,2']bipyridinyl-5'-yl)-heptyloxy]-benzoylamino}-propionic acid

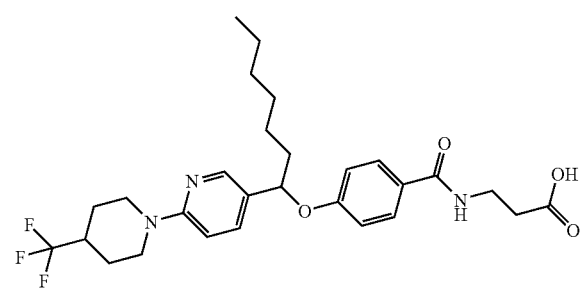

MS (ES): 534.24 [M+H]⁻, the structure is also confirmed by proton NMR.

Example 139

(R,S)-3-{4-[1-(2,6-Dimethyl-4'-trifluoromethyl-biphenyl-4-yl)-3-methyl-butoxy]-benzoylamino}-propionic acid

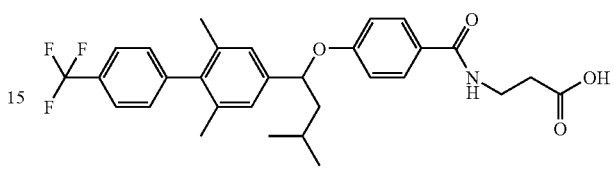

To a solution of 1-(2,6-dimethyl-4'-trifluoromethyl-biphenyl-4-yl)-3-methyl-butan-1-ol (270 mg, 0.8 mmol) in toluene (8 mL) is added 1,1'-(azodicarbonyl) dipiperidine (ADDP, 304 mg, 1.21 mmol) at 0° C., followed by the addition of tributylphosphine (0.3 mL, 12.1 mmol) and 3-(4-hydroxy-benzoylamino)-propionic acid methyl ester (215 mg, 0.96 mmol). The reaction mixture is warmed up to room temperature and stirred overnight. The mixture is loaded on silica gel, eluted with hexanes with a gradient from 0% of ethyl acetate to 100% of ethyl acetate giving 3-{4-[1-(2,6-dimethyl-4'-trifluoromethyl-biphenyl-4-yl)-3-methyl-butoxy]-benzoylamino}-propionic acid methyl ester. The ester product is taken into methanol (2 mL), treated with sodium hydroxide (5N aqueous, 1 mL) for 5 h at room temperature. The mixture is concentrated, diluted with ethyl acetate, acidified with 5 N HCl (1.1 mL), extracted with ethyl acetate. The organic layers are dried and concentrated to afford 51 mg of the titled compound. MS (ES): 528.3 [M+H]⁺.

Example 140

(R,S)-3-{4-[1-Hydroxy-1-(4'-trifluoromethyl-biphenyl-4-yl)-heptyl]-benzoylamino}-propionic acid

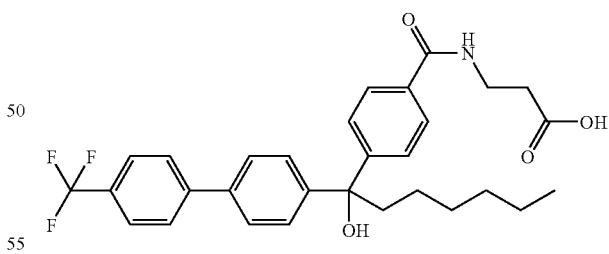

Step A.
4-[1-(4-Bromo-phenyl)-1-hydroxy-heptyl]-benzoic acid

To a solution of 4-(4-bromo-benzoyl)-benzoic acid ethyl ester (2.0 g, 6 mmol) in TBF (20 mL) at 0° C. is added isobutyl magnesium bromide (2M, 3.3 mL). After stirring at room temperature for 2 hours, it is quenched with saturated ammonium chloride, extracted with EtOAc. The organic is concentrated to give 4-[1-(4-bromo-phenyl)-1-hydroxy-heptyl]- benzoic acid ethyl ester (0.48 g, 19%), which was hydrolyzed by 5N NaOH (1 mL) in MeOH (2 mL) to afford the titled compound: 470 mg (99%).

Step B. (R,S)-3-{4-[1-(4-Bromo-phenyl)-1-hydroxy-heptyl]-benzoylamino}-propionic acid methyl ester To a mixture of 4-[1-(4-bromo-phenyl)-1-hydroxy-heptyl]-benzoic acid (470 mg, 1.2 mmol) in methylene chloride (12 mL) are added triethyl amine (0.5 mL, 3.61 mmol), DMAP (5.0 mg), 3-amino-propionic acid methyl ester (252 mg, 1.8 mmol) and EDCI (693 mg, 3.61 mmol) at room temperature. The reaction mixture is stirred at room temperature overnight, loaded on silica gel, eluted with eluted with hexanes with a gradient from 0% of ethyl acetate to 100% of ethyl acetate giving the titled compound as colorless oil (350 mg).

Step C. (R,S)-3-{4-[1-Hydroxy-1-(4'-trifluoromethyl-biphenyl-4-yl)-heptyl]-benzoylamino}-propionic acid methyl ester 3-{4-[1-(4-bromo-phenyl)-1-hydroxy-heptyl]-benzoylamino}-propionic acid methyl ester (350 mg, 0.735 mmol), potassium carbonate (304 mg, 2.2 mmol), 4-trifluoromethoxylphenyl boronic acid (279 mg, 1.47 mmol) and tetrakis(triphenylphosphine)palladium (86 mg, 0.074 nmol) are place in a flask. After the reaction is purged with $N_2$ for several times, THF/$H_2O$ (20 mL/5 mL) is added. The resulting solution is refluxed overnight, loaded on silica gel, eluted with hexane and ethyl acetate to give the titled compound (294 mg) as yellow oil.

Step D. (R,S)-3-{4-[1-Hydroxy-1-(4'-trifluoromethyl-biphenyl-4-yl)-heptyl]-benzoylamino}-propionic acid To a mixture of 3-{4-[1-hydroxy-1-(4'-trifluoromethyl-biphenyl-4-yl)-heptyl]-benzoylamino}-propionic acid methyl ester (50 mg) in methanol (2 mL) is added sodium hydroxide (5 N aqueous, 0.5 mL) and stirred for 5 h. The reaction mixture is concentrated and acidified by 5 N HCl (0.5 mL), extracted with ethyl acetate. Combined organic layers are washed with water and brine, dried over sodium sulfate. Concentration gives the title compound (48 mg). MS (ES): 526.2 [M+H]$^-$.

Example 141

3-{4-[1-(4'-Trifluoromethyl-biphenyl-4-yl)-hept-1-enyl]-benzoylamino}-propionic acid

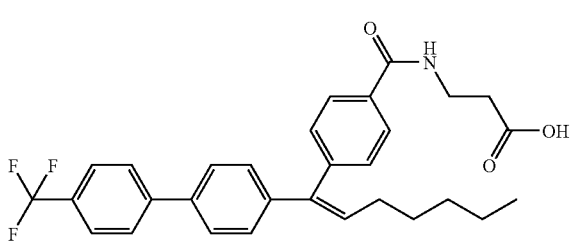

Step A. 3-{4-[1-(4'-Trifluoromethyl-biphenyl-4-yl)-hept-1-enyl]-benzoylamino}-propionic acid methyl ester To a solution of 3-{4-[1-hydroxy-1-(4'-trifluoromethyl-biphenyl-4-yl)-heptyl]-benzoylamino}-propionic acid methyl ester (150 mg, 0.277 mmol) in dichlorormethane (10 mL) is added TFA (160 mg, 1.4 mmol). 5 min later, triethylsilane (161 mg, 1.4 mmol) is added dropwise. 5 h later, the reaction mixture is diluted with ethyl acetate, washed with 1N NaOH, water, brine, dried over sodium sulfate, concentrated and purified by column chromatography to give the title compound (40 mg).

Step B. 3-{4-[1-(4'-Trifluoromethyl-biphenyl-4-yl)-hept-1-enyl]-benzoylamino}-propionic acid To a mixture of 3-{4-[1-(4'-trifluoromethyl-biphenyl-4-yl)-hept-1-enyl]-benzoylamino}-propionic acid methyl ester (40 mg) in methanol (2 mL) is added sodium hydroxide (5 N aqueous, 0.5 mL) and stirred for 5 h. The reaction mixture is concentrated and acidified by 5 NHCl (0.5 mL), extracted with ethyl acetate. Combined organic layers are washed with water and brine, dried over sodium sulfate. Concentration gives the title compound (30 mg). MS (ES): 508.3 [M+H]$^-$.

Example 142

(R,S)-3-{4-[1-(6-Methoxy-4'-trifluoromethyl-biphenyl-3-yl)-heptyl]-benzoylamino}-propionic acid

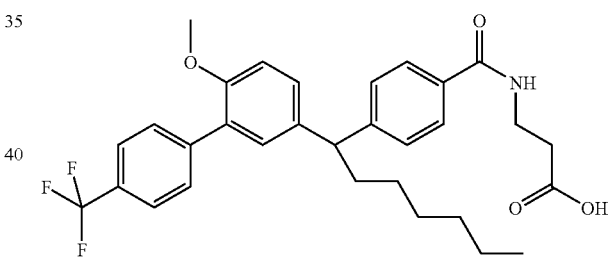

Step A. 4-(4-Methoxy-benzoyl)-benzoic acid methyl ester

To a solution of anisole (3.24 g, 30 mmol) and acid chloride (6 g, 30 mmol) in chloroform (20 mL) is added AlCl$_3$ (3.99 g, 30 mL) in one portion. The mixture is refluxed overnight. And the reaction is quenched with water, extracted with ethyl acetate, dried, concentrated and purified by column chromatography to afford the titled compound: 3.4 g (42%).

Step B. 4-(3-Bromo-4-methoxy-benzoyl)-benzoic acid methyl ester

To the solution of 4-(4-methoxy-benzoyl)-benzoic acid methyl ester (3.4 g, 12.6 mmol) in dichloromethane (10 mL) is added bromine (2.4 g, 15.1 mmol). The solution is stirred at room temperature till the starting material is gone. Then the mixture is diluted with dichlormethane, washed with 1N NaOH, water, brine, dried, and purified with column chromatography to give the titled compound as a yellow solid: 4.42 g (100%).

Step C. 4-[1-(3-Bromo-4-methoxy-phenyl)-1-hydroxy-heptyl]-benzoic acid methyl ester To a solution of 4-(3-bromo-4-methoxy-benzoyl)-benzoic acid methyl ester (4.42 g, 12.66 mmol) in THF (20 mL) at 0° C. is added isobutylmagnesium bromide (2M, 7.6 mL). After stirring at room temperature for 2 hours, it is quenched with saturated ammonium chloride, extracted with EtOAc. The organic is concentrated to give 4-[1-(3-bromo-4-methoxy-phenyl)-1-hydroxy-heptyl]-benzoic acid methyl ester (0.572 g, 10%)

Step D. 4-[1-(3-Bromo-4-methoxy-phenyl)-hept-1-enyl]-benzoic acid

To a solution of 4-[1-(3-bromo-4-methoxy-phenyl)-1-hydroxy-heptyl]-benzoic acid methyl ester (572 mg, 1.31 mmol) in dichloromethane (10 mL) is added TFA (749 mg, 6.57 mmol). 5 min later, triethylsilane (763 mg, 6.57 mmol) is added dropwise. 5 h later, the reaction mixture is diluted with ethyl acetate, washed with 1N NaOH, water, brine, dried over sodium sulfate, concentrated and purified by column chromatography to give 4-[1-(3-bromo-4-methoxy-phenyl)-hept-1-enyl]-benzoic acid methyl ester (380 mg), which is hydrolyzed by 5N NaOH (1 mL) to afford the titled compound (380 mg).

Step E. 3-{4-[1-(3-Bromo-4-methoxy-phenyl)-hept-1-enyl]-benzoylamino}-propionic acid methyl ester To a mixture of 4-[1-(3-bromo-4-methoxy-phenyl)-hept-1-enyl]-benzoic acid (380 mg, 0.94 mmol) in methylene chloride (9 mL) are added triethyl amine (0.39 mL, 2.81 mmol), DMAP (5.0 mg), 3-amino-propionic acid methyl ester (197 mg, 1.41 mmol) and EDCI (541 mg, 2.81 mmol) at room temperature. The reaction mixture is stirred at room temperature overnight, loaded on silica gel, eluted with eluted with hexanes with a gradient from 0% of ethyl acetate to 100% of ethyl acetate giving the titled compound (321 mg).

Step F. 3-{4-[1-(6-Methoxy-4'-trifluoromethyl-biphenyl-3-yl)-hept-1-enyl]-benzoylamino}-propionic acid methyl ester 3-{4-[1-(3-bromo-4-methoxy-phenyl)-hept-1-enyl]-benzoylamino}-propionic acid methyl ester (321 mg, 0.66 mmol), potassium carbonate (2734 mg, 1.98 mmol), 4-trifluoromethoxylphenyl boronic acid (249 mg, 1.31 mmol) and tetrakis(triphenylphosphine)palladium (76 mg, 0.066 mmol) are place in a flask. After the reaction is purged with N₂ for several times, THF/H2O (20 mL/5 mL) is added. The resulting solution is refluxed overnight, loaded on silica gel, eluted with hexane and ethyl acetate to give the titled compound (370 mg).

Step G. (R,S)-3-{4-[1-(6-Methoxy-4'-trifluoromethyl-biphenyl-3-yl)-heptyl]-benzoylamino}-propionic acid To a solution of 3-{4-[1-(6-methoxy-4'-trifluoromethyl-biphenyl-3-yl)-hept-1-enyl]-benzoylamino}-propionic acid methyl ester (330 mg) in ethanol (10 mL) is added Pd/C (5%, 20 mg). The system is purged with N₂, filled with H₂ (30 PSI), stirred at room temperature for 5 h. Then the mixture is filtered through celites, and the filtrate is concentrated to give 3-{4-[1-(6-methoxy-4'-trifluoromethyl-biphenyl-3-yl)-heptyl]-benzoylamino}-propionic acid methyl ester (290 mg), hydrolyze by 5N NaOH (0.5 mL) to afford the titled compound. MS (ES): 540.3 [M+H]⁻.

Example 143

3-{4-[1-(2,6-Dimethyl-4'-trifluoromethyl-biphenyl-4-yl)-3-methyl-butoxy]-benzoylamino}-propionic acid, Isomer 1

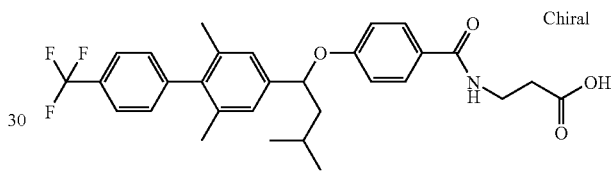

Chiral Separation

The racemic 3-{4-[1-(2,6-dimethyl-4'-trifluoromethyl-biphenyl-4-yl)-3-methyl-butoxy]-benzoylamino}-propionic acid methyl ester was resolved on a Chiralpak AD column (4.6×150 mm). Eluted with Isopropyl Alcohol/Heptane (10/90) and concentrated the fractions to provide a purified enantiomer ester (isomer 1, >95% ee). Hydrolysis of the purified enantiomer of the ester provided the title compound as a white solid. MS (ES): 528.3 [M+H]⁺.

The following enantiomerically purified compounds were obtained by substantially similar chiral separation using Chiralpak AD column (4.6×150 mm) followed by hydrolysis:

Example 144

3-{4-[1-(2,6-Dimethyl-4'-trifluoromethyl-biphenyl-4-yl)-3-methyl-butoxy]-benzoylamino}-propionic acid, Isomer 2

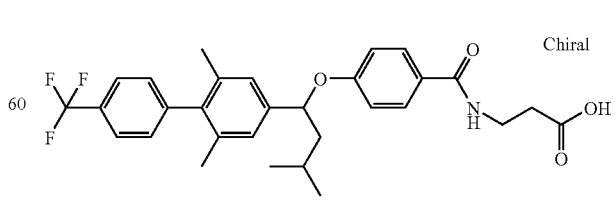

This compound is prepared by resolving racemic 3-{4-[1-(2,6-dimethyl-4'-trifluoromethyl-biphenyl-4-yl)-3-methylbutoxy]-benzoylamino}-propionic acid methyl ester on Chiralpak AD column (4.6×150 mm). MS (ES): 528.3 [M+H]+.

Example 145

3-{4-[1-(6-Methoxy-4'-trifluoromethyl-biphenyl-3-yl)-heptyl]-benzoylamino}-propionic acid, Isomer 1

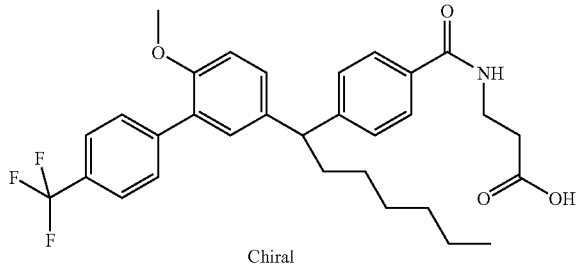

This compound is made prepared by resolving 3-{4-[1-(6-Methoxy-4'-trifluoromethyl-biphenyl-3-yl)-heptyl]-benzoylamino}-propionic acid methyl ester on Chiralpak AD column (4.6×150 mm). MS (ES): 540.3 [M+H]−.

Example 146

3-{4-[1-(6-Methoxy-4'-trifluoromethyl-biphenyl-3-yl)-heptyl]-benzoylamino}-propionic acid, Isomer 2

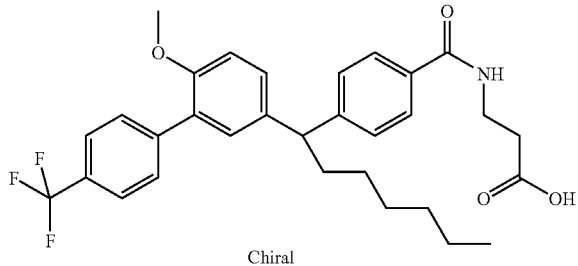

This compound is prepared by resolving 3-{4-[1-(6-methoxy-4'-trifluoromethyl-biphenyl-3-yl)-heptyl]-benzoylamino}-propionic acid methyl ester on Chiralpak AD column (4.6×150 mm). MS (ES): 540.3 [M+H]−.

Example 147

(R,S)-3-(3-Fluoro-4-{1-[6-(4-trifluoromethyl-phenyl)-pyridin-3-yl]-heptyloxy}-benzoylamino)-propionic acid

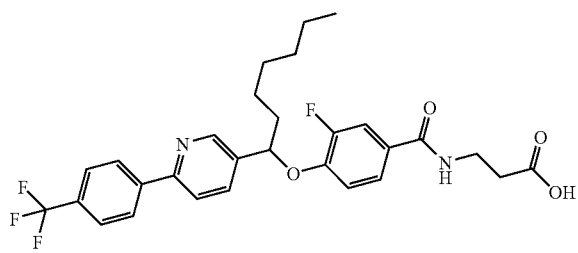

Step A. 3-Fluoro-4-{1-[6-(4-trifluoromethyl-phenyl)-pyridin-3-yl]-heptyloxy}-benzoic acid methyl ester Combine 1-[6-(4-trifluoromethyl-phenyl)-pyridin-3-yl]-heptan-1-ol (0.050 g, 0.15 mmol) and 3-fluoro-4-hydroxy-benzoic acid methyl ester (0.030 g, 0.18 mmol) in toluene (0.5 mL). Add 1,1'-(diazocarbonyl)dipiperidine (0.057 g, 0.23 mmol) followed by tributyl-phosphine (0.06 mL, 0.23 mmol) under inert atmosphere. Stir at room temperature for 16 hours. Dilute reaction with ethyl acetate filter and remove solvent under reduced pressure. Purify on silica gel chromatography (0-40% ethyl acetate/hexane gradient) to provide 0.04 g of title compound (57%).

Step B. 3-Fluoro-4-{1-[6-(4-trifluoromethyl-phenyl)-pyridin-3-yl]-heptyloxy}-benzoic acid Add sodium hydroxide (5.0N, 0.09 mL, 0.42 mmol) to 3-fluoro-4-{1-[6-(4-trifluoromethyl-phenyl)-pyridin-3-yl]-heptyloxy}-benzoic acid methyl ester (0.04 g, 0.085 mmol) in methanol (2 mL). Add tetrahydro-furan (1 ml) and stir for four hours. Acidify with 1.0 N HCl and extract desired compound with ethyl acetate three times. Dry organic fractions with $Na_2SO_4$, filter and concentrate under reduced pressure to provide 0.035 g (90%) of title compound.

Step C. 3-(3-Fluoro-4-{1-[6-(4-trifluoromethyl-phenyl)-pyridin-3-yl]-heptyloxy}-benzoylamino)-propionic acid methyl ester Combine 3-Fluoro-4-{1-[6-(4-trifluoromethyl-phenyl)-pyridin-3-yl]-heptyloxy}-benzoic acid (0.033 g, 0.07 mmol), PyBOP (0.044 g, 0.084 mmol), 3-amino-propionic acid methyl ester hydrochloride (0.0195 g, 0.14 mmol) and tri-ethyl-amine (0.04 mL, 0.28 mmol) in N,N-dimethyl-formamide (1.5 mL). Stir for sixteen hours at room temperature. Dilute reaction with ethyl acetate and water. Wash organic layer with water two times then wash with saturated sodium chloride solution. Dry organic fraction with $Na_2SO_4$, filter and concentrate under reduced pressure. Purify on silica gel chromatography (30-80% Ethyl acetate/hexanes gradient) to provide 0.04 g of title compound (99%).

Step D. 3-(3-Fluoro-4-{1-[6-(4-trifluoromethyl-phenyl)-pyridin-3-yl]-heptyloxy}-benzoylamino)-propionic acid Add sodium hydroxide (5.0N, 0.07 mL, 0.34 mmol) to 3-(3-fluoro-4-{1-[6-(4-trifluoromethyl-phenyl)-pyridin-3-yl]-heptyloxy}-benzoylamino)-propionic acid methyl ester (0.038 g, 0.07 mmol) in methanol (0.5 mL) and stir for three hours. Acidify with 1.0 N HCl and extract desired compound with ethyl acetate three times. Dry organic fractions with $Na_2SO_4$, filter and concentrate under reduced pressure to provide 0.025 g (66%) of title compound. MS (ESI) m/z 547.2 (M++H).

Example 148

(R,S)-3-{3-Fluoro-4-[1-(4'-trifluoromethyl-biphenyl-4-yl)-heptyloxy]-benzoylamino}-propionic acid

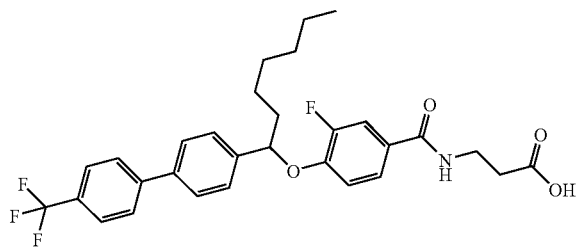

Add sodium hydroxide (5.0N, 0.03 mL, 0.15 mmol) to 3-{3-fluoro-4-[1-(4'-trifluoromethyl-biphenyl-4-yl)-heptyloxy]-benzoylamino}-propionic acid ethyl ester (0.0172 g, 0.03 mmol) in ethanol (0.5 mL) and stir for three hours. Acidify with 1.0 N HCl and extract desired compound with ethyl acetate three times. Dry organic fractions with $Na_2SO_4$, filter and concentrate under reduced pressure to provide 0.015 g (92%) of title compound. MS (ESI) m/z 546.3 (M++H).

Example 149

(R,S)-3-{3-Fluoro-4-[1-(2-methyl-4'-trifluoromethyl-biphenyl-4-yl)-heptyloxy]-benzoylamino}-propionic acid

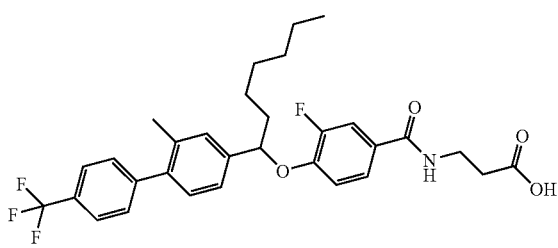

Add sodium hydroxide (5.0N, 0.03 mL, 0.15 mmol) to 3-{3-fluoro-4-[1-(2-methyl-4'-trifluoromethyl-biphenyl-4-yl)-heptyloxy]-benzoylamino}-propionic acid ethyl ester (0.024 g, 0.041 mmol) in ethanol (5 mL) and stir for three hours. Acidify with 1.0 N HCl and extract desired compound with ethyl acetate three times. Wash organic phase with saturated sodium chloride solution, dry over $Na_2SO_4$, filter, and concentrate under reduced pressure to provide 0.019 g (83%) of title compound. MS (ESI) m/z 560.2 (M$^+$+H).

Example 150

(R,S)-3-{4-[1-(4'-Isopropyl-2-methyl-biphenyl-4-yl)-5-methyl-hexyloxy]-benzoylamino}-propionic acid

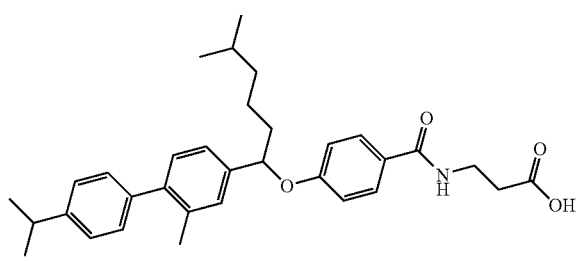

Step A.
4-Bromo-N-methoxy-3,N-dimethyl-benzamide

4-Bromo-3-methyl-benzoic acid methyl ester (6 g, 26.19 mmol) was dissolved into anhydrous tetrahydrofuran (THF) (200 mL) and then cooled to −30° C. while stirring under nitrogen. N,O-dimethylhydroxylamine hydrochloride (3.81 g, 39.29 mmol) was then added to the solution in one portion. Isopropyl magnesium chloride (39 mL, 2M soln. in THF, 78.6 mmol) was slowly added to the cooled suspension over 1 h. After complete consumption of starting material, then 30% solution of ammonium chloride was added with stirring. The reaction was diluted with diethyl ether and extracted. The organic layer was collected and washed with cold water (2×) and brine. The solution was then dried over anhydrous sodium sulfate, filtered, and concentrated. The 4-Bromo-N-methoxy-3,N-dimethyl-benzamide (5.94 g, 23.05 mmol) was obtained in purified form after flash column chromatography.

Step B. 1-(4-Bromo-3-methyl-phenyl)-5-methyl-hexan-1-one

4-Bromo-N-methoxy-3,N-dimethyl-benzamide (5.94 g, 23.05 mmol) was suspended in anhydrous tetrahydrofuran (200 mL), and cooled to 0° C. with stirring under nitrogen. 1-magnesium bromo-4-methyl-pentane (23 mL, 1.5M in tetrahydrofuran, 34.8 mmol) was slowly added to the reaction over 1 h. The reaction was allowed to warm slowly to room temperature and monitored by TLC. Upon complete consumption of starting material, the reaction was carefully neutralized with 1N hydrochloric acid, extracted with diethyl ether, washed, dried, and concentrated. The 1-(4-Bromo-3-methyl-phenyl)-5-methyl-hexan-1-one (5.2 g, 18.4 mmol) 80% yield, was used without further purification.

Step C. 1-(4-Bromo-3-methyl-phenyl)-5-methyl-hexan-1-ol 1-(4-Bromo-3-methyl-phenyl)-5-methyl-hexan-1-one (3.5 g, 12.4 mmol) was dissolved in ethanol and cooled to 0° C. while stirring under nitrogen. To the flask was added sodium borohydride (469 mg, 12.4 mmol), and the reaction was kept at 0° C. for 1 h., then slowly warmed to room temperature. The reaction was monitored by HPLC. Upon complete consumption of starting material, the reaction is carefully quenched with water, the ethanol removed by rotary evaporator, and extracted with diethyl ether, washed, dried, and concentrated. The title compound (3.33 g, 11.72 mmol), is used in the next step without further purification.

Step D. 3-{4-[1-(4-Bromo-3-methyl-phenyl)-5-methyl-hexyloxy]-benzoylamino}-propionic acid methyl ester A solution of 3-(4-hydroxy-benzoylamino)-propionic acid methyl ester (805 mg, 3.61 mmol) and 1-(4-Bromo-3-methyl-phenyl)-5-methyl-hexan-1-ol (824 mg, 2.89 mmol) in toluene (15.0 mL) was degassed and filled with nitrogen for 3 times. Tributylphosphine (1.1 mL, 4.33 mmol) was added to the reaction mixture under nitrogen at 0° C., followed by addition of 1,1'-(azodicarbonyl)-dipiperidine (1.1 g, 4.33 mmol). The reaction mixture was allowed to warm to room temperature and stirred over night, the mixture was loaded on silica gel column. Chromatography gave the title compound (890 mg, 1.82 mmol).

Step E. 3-{4-[1-(4'-Isopropyl-2-methyl-biphenyl-4-yl)-5-methyl-hexyloxy]-benzoylamino}-propionic acid methyl ester 3-{4-[1-(4-Bromo-3-methyl-phenyl)-5-methyl-hexyloxy]-benzoylamino}-propionic acid methyl ester (460 mg, 0.940 mmol) was dissolved in toluene (2.5 mL), followed by palladium tetrakis triphenylphosphine (46 mg, 0.0395 mmol), 4-isopropyl-phenyl boronic acid (308 mg, 1.88 mmol), and potassium fluoride (109 mg, 1.88 mmol). The reaction was purged with nitrogen and heated to reflux, then the water (2.5 mL) was added. The reaction was monitored by HPLC, and upon completion, allowed to cool to room temperature. The reaction was diluted with EtOAc and then celite added, followed by water. This mixture was then filtered through a pad of celite. The solution was separated in a separatory funnel, then the organic layer was washed with 0.1N sodium hydroxide, water, and brine. The organic layer was dried over anhydrous sodium sulfate, then concentrated. The product was purified by flash column chromatography (444 mg, 0.800 mmol).

Step F. 3-{4-[1-(4'-Isopropyl-2-methyl-biphenyl-4-yl)-5-methyl-hexyloxy]-benzoylamino}-propionic acid 3-{4-[1-(4'-Isopropyl-2-methyl-biphenyl-4-yl)-5-methyl-hexyloxy]-benzoylamino}-propionic acid methyl ester (50 mg) was taken into THF (1.0 mL) and treated with NaOH (1.0 mL, 5.0 N), then refluxed under nitrogen. The reaction mixture was neutralized with HCl (1.0 mL, 5.0 N), extracted with ethyl ether, dried over sodium sulfate. Concentration gave the title compound. MS (ES): 516.7 [M+H]$^+$, the structure was also confirmed by proton NMR.

Example 151

(R,S)-3-{4-[1-(4'-tert-Butyl-2-methyl-biphenyl-4-yl)-5-methyl-hexyloxy]-benzoylamino}-propionic acid

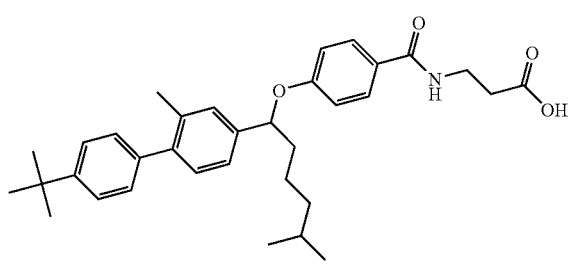

The titled compound is made in a manner substantially similar to Example 150, step E starting with 3-{4-[1-(4-Bromo-3-methyl-phenyl)-5-methyl-hexyloxy]-benzoylamino}-propionic acid methyl ester and 4-tBu-phenyl boronic acid. MS (ES): 530.7 [M+H]$^+$, the structure was also confirmed by proton NMR.

Example 152

(R,S)-3-{4-[1-(4'-tert-Butyl-2-methyl-biphenyl-4-yl)-heptyloxy]-benzoylamino}-propionic acid

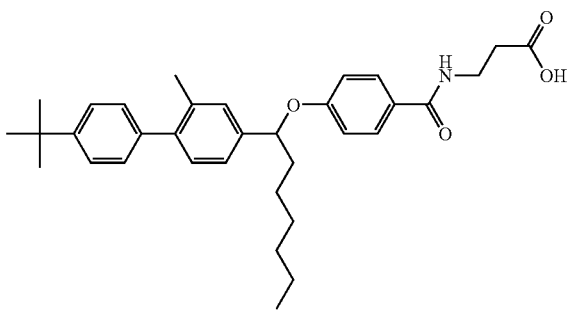

The titled compound is made in a manner substantially similar to Example 150, step D, starting with 1-(4-bromo-3-methyl-phenyl)-heptan-1-ol and 3-(4-Hydroxy-benzoylamino)-propionic acid methyl ester. MS (ES): 530.7 [M+H]$^+$, the structure was also confirmed by proton NMR.

Example 153

(R,S)-3-{4-[(4'-tert-Butyl-2-methyl-biphenyl-4-yl)-cyclohexyl-methoxy]-benzoylamino}-propionic acid

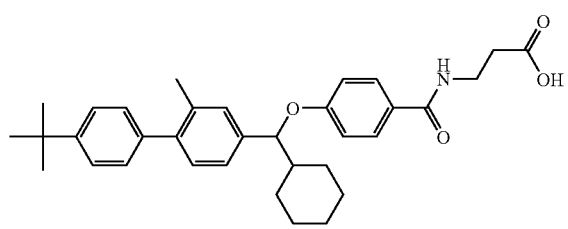

The titled compound is made in a manner substantially similar to Example 150, step D starting with (4-bromo-3-methyl-phenyl)-cyclohexyl-methanol and 3-(4-hydroxy-benzoylamino)-propionic acid methyl ester. MS (ES): 528.7 [M+H]$^+$, the structure was also confirmed by proton NMR.

Example 154

3-{4-[(4'-tert-Butyl-2-methyl-biphenyl-4-yl)-cyclohexyl-methoxy]-benzoylamino}-propionic acid, Isomer 1

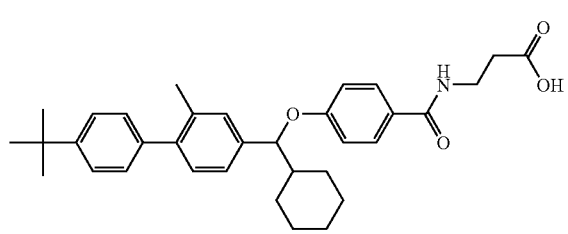

MS (ES): 528.7 [M+H]$^+$, the structure was also confirmed by proton NMR

Chiral Separation Procedure:

The racemic 3-{4-[(4'-tert-Butyl-2-methyl-biphenyl-4-yl)-cyclohexyl-methoxy]-benzoylamino}-propionic acid was resolved on a Chiralcel OD column (4.6×250 mm). Eluted with isopropyl alcohol in heptane with 0.2% dimethylethylamine and concentrated the fractions to provide a purified enantiomer ester (isomer 1, 94.9% ee).

Hydrolysis of the purified enantiomer of the ester provided the title compound as a white solid. MS (ES): 528.7 [M+H]$^+$, the structure was also confirmed by proton NMR.

The following enantiomeric purified compounds were obtained by similar chiral separation using Chiralcel OD column (4.6×250 mm) or using Chiralcel OJ column (4.6×250 mm):

Example 155

3-{4-[(4'-tert-Butyl-2-methyl-biphenyl-4-yl)-cyclohexyl-methoxy]-benzoylamino}-propionic acid, Isomer 2

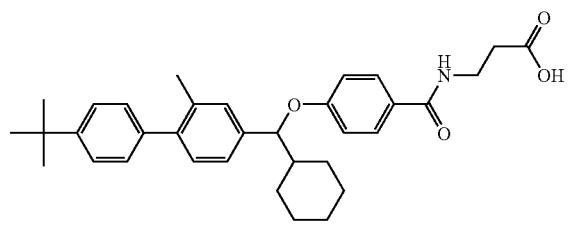

MS (ES): 528.7 [M+H]$^+$, the structure was also confirmed by proton NMR

Example 156

3-{4-[1-(4'-tert-Butyl-2-methyl-biphenyl-4-yl)-heptyloxy]-benzoylamino}-propionic acid, isomer 1

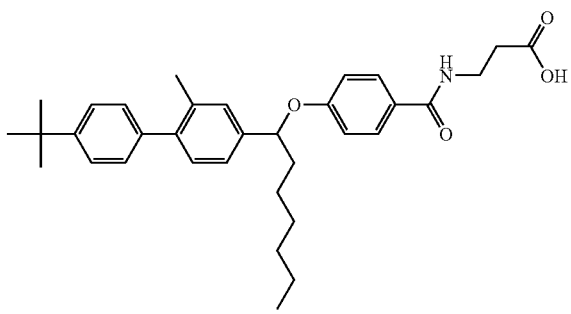

MS (ES): 530.7 [M+H]$^+$, the structure was also confirmed by proton NMR

Example 157

3-{4-[1-(4'-tert-Butyl-2-methyl-biphenyl-4-yl)-heptyloxy]-benzoylamino}-propionic acid, Isomer 2

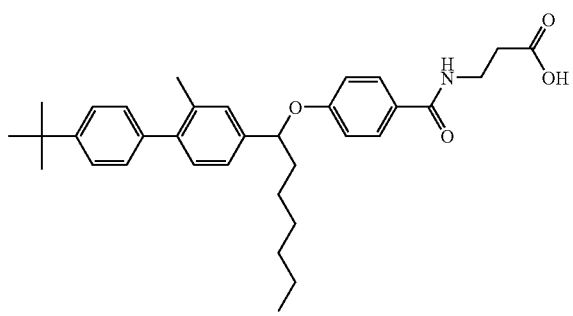

MS (ES): 530.7 [M+H]$^+$, the structure was also confirmed by proton NMR

Example 158

3-{4-[5-Methyl-1-(2-methyl-4'-trifluoromethyl-biphenyl-4-yl)-hexyloxy]-benzoylamino}-propionic acid, Isomer 1

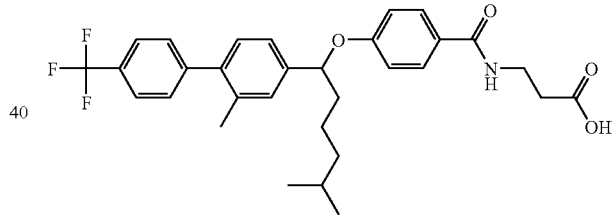

MS (ES): 542.6 [M+H]$^+$, the structure was also confirmed by proton NMR.

Example 159

3-{4-[5-Methyl-1-(2-methyl-4'-trifluoromethyl-biphenyl-4-yl)-hexyloxy]-benzoylamino}-propionic acid, Isomer 2

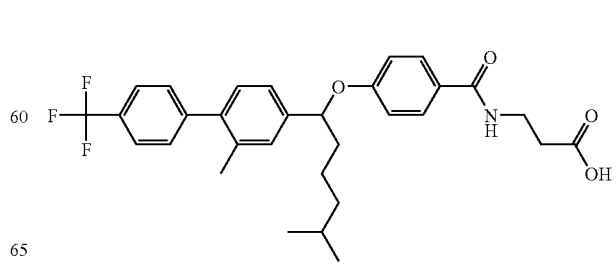

MS (ES): 542.6 [M+H]+, the structure was also confirmed by proton NMR.

Example 160

3-{4-[1-(4'-Isopropyl-2-methyl-biphenyl-4-yl)-5-methyl-hexyloxy]-benzoylamino}-propionic acid, Isomer 1

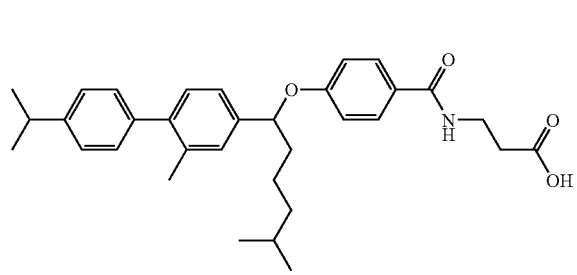

MS (ES): 516.7 [M+H]+, the structure was also confirmed by proton NMR.

Example 161

3-{4-[1-(4'-Isopropyl-2-methyl-biphenyl-4-yl)-5-methyl-hexyloxy]-benzoylamino}-propionic acid, Isomer 2

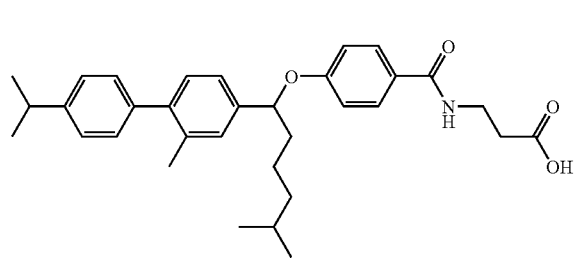

MS (ES): 516.7 [M+H]+, the structure was also confirmed by proton NMR.

Example 162

3-{4-[1-(4'-tert-Butyl-2-methyl-biphenyl-4-yl)-5-methyl-hexyloxy]-benzoylamino}-propionic acid, Isomer 1

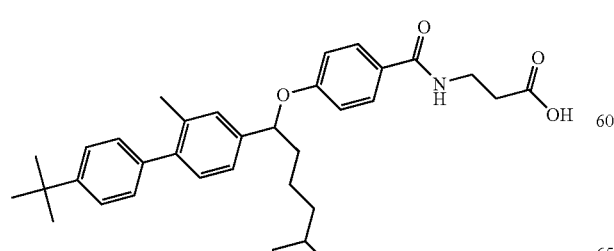

MS (ES): 530.7 [M+H]+, the structure was also confirmed by proton NMR.

Example 163

3-{4-[1-(4'-tert-Butyl-2-methyl-biphenyl-4-yl)-5-methyl-hexyloxy]-benzoylamino}-propionic acid, Isomer 2

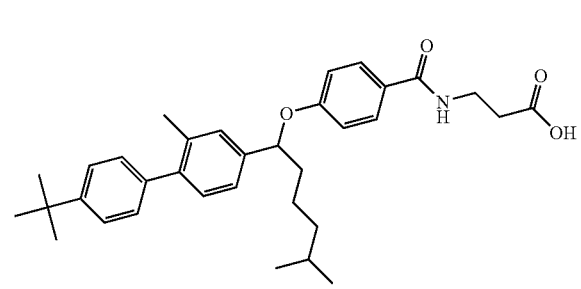

MS (ES): 530.7 [M+H]+, the structure was also confirmed by proton NMR.

Example 164

(R,S)-3-{3-Fluoro-4-[1-(4'-trifluoromethyl-biphenyl-4-yl)-heptyloxy]-benzoylamino}-propionic acid

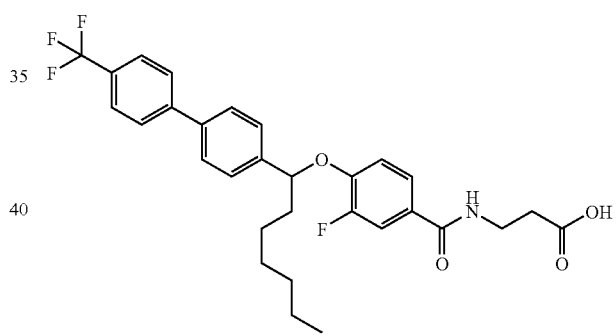

Step A. 1-(4'-Trifluoromethyl-biphenyl-4-yl)-heptan-1-ol

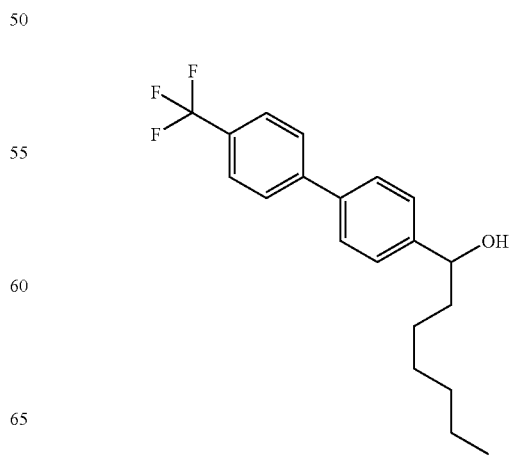

Add hexyl magnesium bromide (2.0M in ethyl ether, 8 mL, 16 mmol) to 4'-trifluoromethyl-biphenyl-4-carbaldehyde (2.0 g, 8 mmol) (prepared in a manner substantially similar to preparation 25, or other methods known in the art) in tetrahydro-furan (30 mL) at 0° C. under inert atmosphere. Stir 1.5 hours. Quench reaction with saturated solution of ammonium chloride, dilute with ethyl acetate. Wash organic phase with water then saturated sodium chloride solution. Dry organic fraction with $Na_2SO_4$, filter, and concentrate under reduced pressure. Purify on silica gel chromatography (0-30% Ethyl acetate/hexanes gradient) to provide 1.95 g of title compound (73%).

Step B.
3-(3-Fluoro-4-hydroxy-benzoylamino)-propionic acid ethyl ester

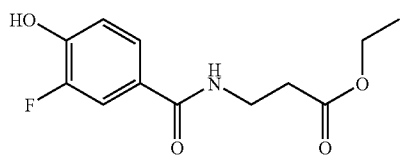

Combine 3-Fluoro-4-hydroxy-benzoic acid (1.0 g, 6.4 mmol), PyBOP (4.0 g, 7.69 mmol), 3-amino-propionic acid ethyl ester hydrochloride (1.47 g, 9.6 mmol) and ethyl-diisopropyl-amine (4.55 mL, 25.6 mmol) in N,N-dimethyl-formamide (20 mL). Stir for sixty-six hours at room temperature. Dilute reaction with ethyl acetate and water. Wash organic layer with saturated solution of ammonium chloride and water. Extract combined aqueous fraction with ethyl acetate. Wash combined organic fractions with saturated sodium chloride solution. Dry organic fraction with $Na_2SO_4$, filter and concentrate under reduced pressure. Purify on silica gel chromatography (20-80% Ethyl acetate/hexanes gradient) to provide 1.24 g of title compound (76%).

Step C. 3-{3-Fluoro-4-[1-(4'-trifluoromethyl-biphenyl-4-yl)-heptyloxy]-benzoylamino}-propionic acid ethyl ester

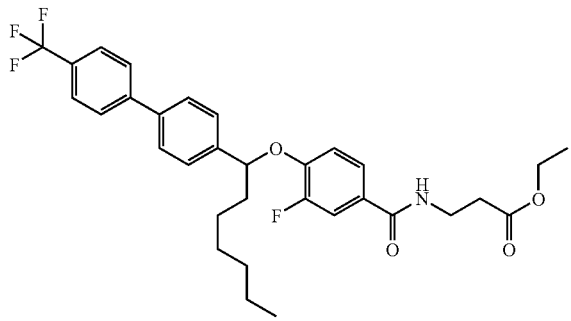

Combine 1-(4'-trifluoromethyl-biphenyl-4-yl)-heptan-1-ol (0.257 g, 0.76 mmol) and 3-(3-Fluoro-4-hydroxy-benzoylamino)-propionic acid ethyl ester (0.150 g, 0.59 mmol) in toluene (3.0 mL). Add 1,1'(diazocarbonyl)dipiperidine (0.223 g, 0.88 mmol) followed by tributyl-phosphane (0.22 mL, 0.88 mmol) under inert atmosphere. Stir at room temperature for 18 hours. Dilute reaction with ethyl acetate filter and remove solvent under reduced pressure. Purify on silica gel chromatography (0-70% Ethyl acetate/hexanes gradient) to provide 0.305 g of title compound (90%).

Step D. 3-{3-Fluoro-4-[1-(4'-trifluoromethyl-biphenyl-4-yl)-heptyloxy]-benzoylamino}-propionic acid Add sodium hydroxide (5.0N, 0.03 mL, 0.15 mmol) to 3-{3-fluoro-4-[1-(4'-trifluoromethyl-biphenyl-4-yl)-heptyloxy]-benzoylamino}-propionic acid ethyl ester (0.0172 g, 0.03 mmol) in ethanol (0.5 mL) and stir for three hours. Acidify with 1.0 N HCl and extract desired compound with ethyl acetate three times. Dry organic fractions with $Na_2SO_4$, filter and concentrate under reduced pressure to provide 0.015 g (92%) of title compound. MS (ESI) m/z 546.3 $[M+H]^+$.

Example 165

(R,S)-3-{3-Fluoro-4-[1-(2-methyl-4'-trifluoromethyl-biphenyl-4-yl)-heptyloxy]-benzoylamino}-propionic acid

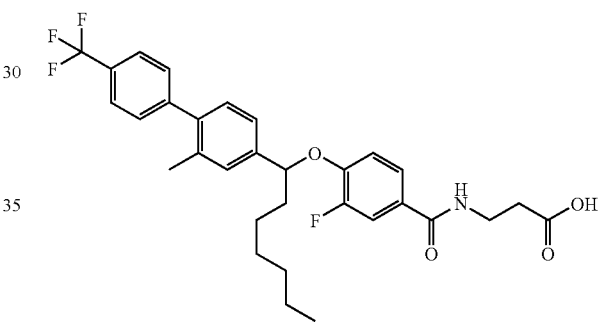

Step A. 2-Methyl-4'-trifluoromethyl-biphenyl-4-carboxylic acid methyl ester

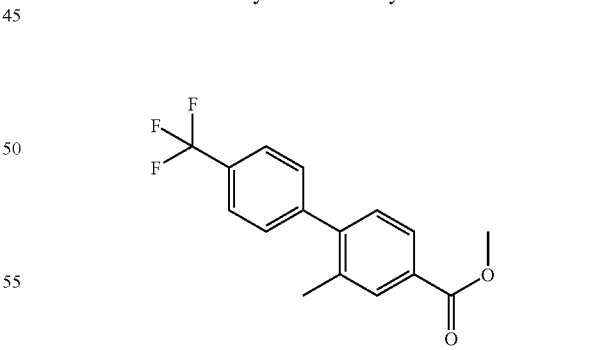

Combine 4-bromo-3-methyl-benzoic acid methyl ester (2.01 g, 8.8 mmol) 4-(trifluoromethyl)phenyl boronic acid (2.0 g, 10.53 mmol), (tetrakis(triphenylphospine)palladium (0) (0.608 g, 0.53 mmol), and cesium fluoride (3.2 g, 21.06 mmol) in acetonitrile (30 mL) and stir for 18 hrs at 80° C. under inert atmosphere. Filter reaction with filter agent and rinse with ethyl acetate. Purify on silica gel chromatography (0-20% Ethyl acetate/hexanes gradient) to provide 2.53 g of title compound (98%).

Step B. 2-Methyl-4'-trifluoromethyl-biphenyl-4-carboxylic acid

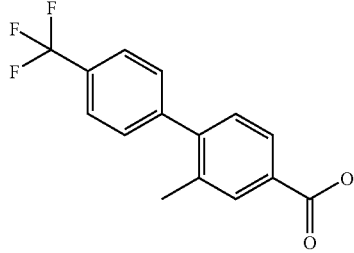

Add sodium hydroxide (5.0N, 0.03 mL, 0.15 mmol) to 2-methyl-4'-trifluoromethyl-biphenyl-4-carboxylic acid methyl ester (2.52 g, 8.6 mmol) in methanol (15 mL) and stir for two hours. Acidify with 1.0 N HCl and extract desired compound with ethyl acetate three times. Wash organic phase with saturated sodium chloride solution, dry over $Na_2SO_4$, filter and concentrate under reduced pressure to provide 2.31 g (96%) of title compound.

Step C. 2-Methyl-4'-trifluoromethyl-biphenyl-4-carboxylic acid methoxy-methyl-amide

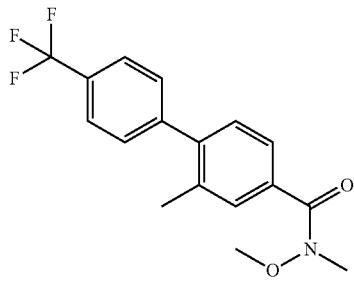

Combine 2-methyl-4'-trifluoromethyl-biphenyl-4-carboxylic acid (2.31 g, 8.25 mmol) and di-imidazol-1-yl-methanone (1.47 g, 9.08 mmol) in tetrahydro-furan (15 mL) and stir twenty minutes. In a separate reaction vessel, combine O,N-dimethyl-hydroxylamine hydrochloride (0.885 g, 9.08 mmol) and triethyl-amine (1.3 mL, 9.08 mmol) in N,N-dimethyl-formamide (20 mL). Add O,N-dimethyl-hydroxylamine solution to the 2-methyl-4'-trifluoromethyl-biphenyl-4-carboxylic acid solution and stir sixteen hours. Dilute reaction with ethyl acetate, wash with 0.5 N HCl, 0.1N NaOH, and saturated sodium chloride solution. Dry organic fraction with $Na_2SO_4$, filter and concentrate under reduced pressure to provide 0.6 g (23%) of title compound.

Step D. 1-(2-Methyl-4'-trifluoromethyl-biphenyl-4-yl)-heptan-1-one

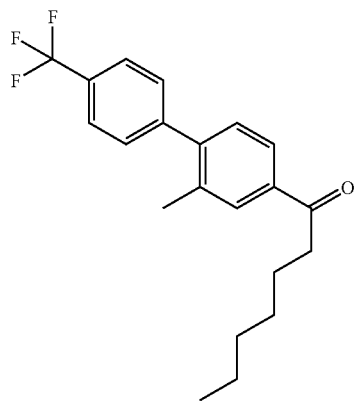

Dissolve 2-methyl-4'-trifluoromethyl-biphenyl-4-carboxylic acid methoxy-methyl-amide (0.58 g, 1.8 mmol) in tetrahydro-furan (10 mL). Add hexyl magnesium bromide (2.0M ethyl ether, 2.69 mL, 5.39 mmol) at 0° C. under inert atmosphere and stir 1.5 hours. Quench reaction with saturated solution of ammonium chloride, dilute with ethyl acetate. Wash organic phase with water then saturated sodium chloride solution. Dry organic fraction with $Na_2SO_4$, filter and concentrate under reduced pressure. Purify on silica gel chromatography (0-30% Ethyl acetate/hexanes gradient) to provide 0.518 g of title compound (83%).

Step E. 1-(2-Methyl-4'-trifluoromethyl-biphenyl-4-yl)-heptan-1-ol

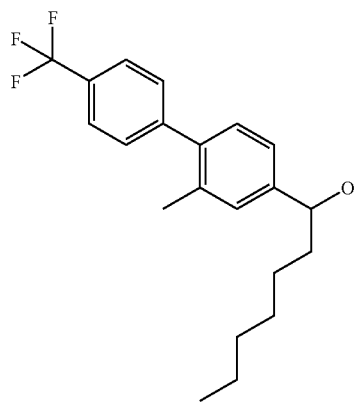

Dissolve 1-(2-methyl-4'-trifluoromethyl-biphenyl-4-yl)-heptan-1-one (0.516 g, 1.48 mmol) in ethanol (5 mL). Add sodium borohydride (0.224 g, 5.93 mmol) at 0° C. under inert atmosphere and stir three hours. Quench reaction with saturated solution of ammonium chloride, dilute with ethyl acetate. Wash organic phase with saturated sodium bicarbonate solution, then saturated sodium chloride solution. Dry organic fraction with $Na_2SO_4$, filter and concentrate under reduced pressure. Purify on silica gel chromatography (0-30% Ethyl acetate/hexanes gradient) to provide 0.5 g of title compound (97%).

Step F. 3-{3-Fluoro-4-[1-(2-methyl-4'-trifluoromethyl-biphenyl-4-yl)-heptyloxy]-benzoylamino}-propionic acid ethyl ester

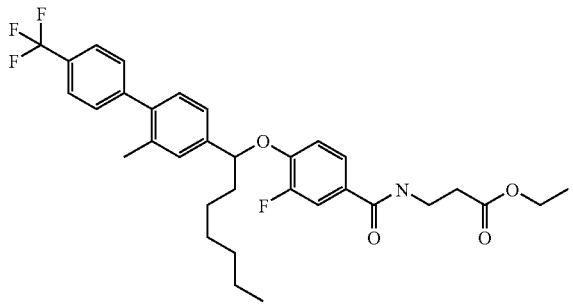

Combine 1-(2-methyl-4'-trifluoromethyl-biphenyl-4-yl)-heptan-1-ol (0.090 g, 0.25 mmol) and 3-(3-fluoro-4-hydroxy-benzoylamino)-propionic acid ethyl ester (0.050 g, 0.20 mmol) in toluene (1.0 mL). Add 1,1'(diazocarbonyl)dipiperidine (0.076 g, 0.3 mmol) followed by tributyl-phosphane (0.074 mL, 0.3 mmol) under inert atmosphere. Stir at room temperature for 16 hours. Dilute reaction with ethyl acetate filter and remove solvent under reduced pressure. Purify on silica gel chromatography (0-50% Ethyl acetate/hexanes gradient) to provide 0.105 g of title compound (90%).

Step G. 3-{3-Fluoro-4-[1-(2-methyl-4'-trifluoromethyl-biphenyl-4-yl)-heptyloxy]-benzoylamino}-propionic acid Add sodium hydroxide (5.0N, 0.03 mL, 0.15 mmol) to 3-{3-Fluoro-4-[1-(2-methyl-4'-trifluoromethyl-biphenyl-4-yl)-heptyloxy]-benzoylamino}-propionic acid ethyl ester (0.024 g, 0.041 mmol) in ethanol (5 mL) and stir for three hours. Acidify with 1.0 N HCl and extract desired compound with ethyl acetate three times. Wash organic phase with saturated sodium chloride solution, dry over $Na_2SO_4$, filter, and concentrate under reduced pressure to provide 0.019 g (83%) of title compound. MS (ESI) m/z 560.2 $[M+H]^+$.

The compound of Formula I is preferably formulated in a unit dosage form prior to administration. Therefore, yet another embodiment of the present invention is a pharmaceutical composition comprising a compound of Formula I and one or more pharmaceutically acceptable carriers, diluents or excipients.

The present pharmaceutical compositions are prepared by known procedures using well-known and readily available ingredients. In making the formulations of the present invention, the active ingredient (Formula I compound) will usually be mixed with a carrier, or diluted by a carrier, or enclosed within a carrier which may be in the form of a capsule, sachet, paper or other container. When the carrier serves as a diluent, it may be a solid, semisolid or liquid material that acts as a vehicle, excipient, or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions of the present invention may be formulated in sustained release form to provide the rate controlled release of any one or more of the components or active ingredients to optimize the therapeutic effects, i.e., antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration, Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as a re conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

There is increasing evidence that glucagon plays an important role in glucose homeostasis. Compounds of Formula I are effective as antagonists or inverse agonists of the glucagon receptor, and thus inhibit the activity of the glucagon receptor. More particularly, these compounds are selective antagonists or inverse agonists of the glucagon receptor. As selective antagonists or inverse agonists, the compounds of Formula I are useful in the treatment of diseases, disorders, or conditions responsive to the inactivation of the glucagon receptor, including but not limited to diabetic and other glucagon related disorder. It is postulated that selective antagonists or inverse agonists of the glucagon receptor will lower plasma glucose levels and thus prevent or treat diabetic and other glucagon related metabolic disorders.

Pharmacological Methods

In the following section binding assays as well as functional assays useful for evaluating the efficiency of the compounds of the invention are described.

Binding of compounds to the glucagon receptor may be determined in a competition binding assay using the cloned human glucagon receptor, and selectivity against the hGlp1 receptor. Antagonism may be determined as the ability of the compounds to inhibit the amount of cAMP formed in in the assay in the presence of 5 nM glucagon.

Glucagon Receptor (hGlucR) Binding Assay

The receptor binding assay used cloned human glucagon receptor (Lok S, Kuijper J L, Jelinek U J, Kramer J M, Whitmore T E, Sprecher C A, Mathewes S, Grant F J, Biggs SH, Rosenberg GB, et al. Gene 140 (2), 203-209 (1994)) isolated from 293HEK membranes. The hGlucR cDNA was subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA was transfected into 293 HEK cells and selec ted with 200 ug/mL Hygromycin.

Crude plasma membranes are prepared using cells from suspension culture. The cells are lysed on ice in hypotonic buffer containing 25 mM Tris HCL, pH 7.5, 1 mM MgCl2, DNAse1, 20 u/mL, and Roche Complete Inhibitors-without EDTA. The cell suspension is homogenized with a glass dounce homogenizer using a Teflon pestle for 25 strokes. The homogenate is centrifuged at 4° C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4° C. The membrane pellet is resuspended in homogenization buffer and stored as frozen aliquots at −80° C. freezer until needed.

Glucagon is radioiodinated by I-125-lactoperoxidase procedure and purified by reversed phase HPLC at Perkin-Elmer/NEN (NEX207). The specific activity is 2200 Ci/mmol. Kd determination is performed by homologous competition instead of saturation binding due to high propanol content in the I-125 glucagon material. The Kd is estimated to be 3 nM and is used to calculate Ki values for all compounds tested.

The binding assays are carried out using a Scintillation Proximity Assay (Amersham) with WGA beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon is dissolved in 0.01 N HCl at 1 mg/mL and immediately frozen at −80° C. in 30 ul aliquots. The glucagon aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon (NSB at 1 uM final). 50 ul of I-125 glucagon (0.15 nM final in reaction), 50 ul of membranes (300 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon binding in the presence of compound. The absolute EC50 dose of compound is derived by non-linear regression of percent specific binding of I-125-glucagon vs. the dose of compound added. The EC50 dose is converted to Ki using the Cheng-Prusoff equation (Cheng Y., Prusoff W. H., Biochem. Pharmacol. 22, 3099-3108, 1973).

Glucagon—Like—Peptide 1 (Glp1-R) Receptor Binding Assay

The receptor binding assay used cloned human glucagon-like peptide 1 receptor (hGlp1-R). (Graziano M P, Hey P J, Borkowski D, Chicchi G G, Strader C D, Biochem Biophys Res Commun. 1993 Oct. 15; 196(1):141-6) isolated from 293HEK membranes. The hGlp1-R cDNA was subcloned into the expression plasmid phD (Trans-activated expression of fully gamma-carboxylated recombinant human protein C, an antithrombotic factor. Grinnell, B. W., Berg, D. T., Walls, J. and Yan, S. B. Bio/Technology 5: 1189-1192 (1987)). This plasmid DNA was transfected into 293 HEK cells and selected with 200 ug/mL Hygromycin.

Crude plasma membrane is prepared using cells from suspension culture. The cells are lysed on ice in hypotonic buffer containing 25 mM Tris HCl, pH 7.5, 1 mM MgCl2, DNAse, 20 u/mL, and Roche Complete Inhibitors without EDTA. The cell suspension is homogenized with a glass dounce homogenizer using a Teflon pestle for 25 strokes. The homogenate is centrifuged at 4° C. at 1800×g for 15 mins. The supernate is collected and the pellet is resuspended in hypotonic buffer and rehomogenized. The mixture is centrifuged at 1800×g for 15 mins. The second supernate is combined with the first supernate. The combined supernates are recentrifuged at 1800×g for 15 mins to clarify. The clarified supernate is transferred to high speed tubes and centrifuged at 25000×g for 30 minutes at 4° C. The membrane pellet is resuspended in homogenization buffer and stored as frozen aliquots in −80° C. freezer until use.

Glucagaon-like peptide 1 (Glp-1) is radioiodinated by the I-125-lactoperoxidase procedure and purified by reversed phase HPLC at Perkin-Elmer/NEN (NEX308). The specific activity is 2200 Ci/mmol. Kd determination is performed by homologous competition instead of saturation binding due to high propanol content in the I-125 Glp-1 material. The Kd is estimated to be 3 nM and is used to calculate Ki values for all compounds tested.

The binding assays are carried out using a Scintillation Proximity Assay (Amersham) with wheat germ agglutinin (WGA) beads previously blocked with 1% fatty acid free BSA (ICN). The binding buffer contains 25 mM Hepes, pH 7.4, 2.5 mM CaCl2, 1 mM MgCl2, 0.1% fatty acid free BSA, (ICN), 0.003% tween-20, and Roche Complete Inhibitors without EDTA. Glucagon-like peptide 1 is dissolved in PBS at 1 mg/mL and immediately frozen at −80° C. in 30 ul aliquots. The glucagon-like peptide aliquot is diluted and used in binding assays within an hour. Test compounds are dissolved in DMSO and serially diluted in DMSO. 10 ul diluted compounds or DMSO is transferred into Corning 3632, opaque clear bottom assay plates containing 90 ul assay binding buffer or cold glucagon-like peptide 1 (NSB at 1 uM final). 50 ul of I-125 glucagon-like peptide 1 (0.15 nM final in reaction), 50 ul of membranes (600 ug/well), and 40 ul of WGA beads (150 ugs/well) are added, covered, and mixed end over end. Plates are read with a MicroBeta after 14 hours of settling time at room temp.

Results are calculated as a percent of specific I-125-glucagon-like peptide 1 binding in the presence of compound. The absolute EC50 dose of compound is derived by non-linear regression of percent specific binding of I-125-glucagon-like peptide 1 vs. the dose of compound added. The EC50 dose is converted to Ki using the Cheng-Prusoff equation (Cheng Y., Prusoff W. H., Biochem. Pharmacol. 22, 3099-3108, 1973).

Glucagon-Stimulated cAMP Functional Antagonist Assay

The cAMP functional assay uses the same cloned human glucagon receptor cell line isolated for the hGlucR binding assay described above. Cells are stimulated with a mixture of an EC80 dose of glucagon in the presence of compound. The cAMP generated within the cell is quantitated using an Amplified Luminescent Proximity Homogeneous Assay, Alpha Screen, from Perkin Elmer (6760625R).

Briefly, cAMP within the cell competes for binding of biotinylated cAMP from the kit to a coated anti-cAMP antibody Acceptor bead and a strepavidin coated Donor bead. As the cAMP level within the cell increases, a disruption of the Acceptor bead-biotinlyated cAMP -Donor bead complex occurs and decreases the signal.

Glucagon is dissolved in 0.01 N HCl at 1 mg/mL and immediately frozen at −80° C. in 30 ul aliquots. The glucagon aliquot is diluted and used in the functional assay within an hour. Cells are harvested from sub-confluent tissue culture dishes with Enzyme-Free Cell Dissociation Solution, (Specialty Media 5-004-B). The cells are pelleted at low speed and washed 3 times with assay buffer [25 mM Hepes in HBSS-with Mg and Ca (GIBCO, 14025-092) with 0.1% Fatty Acid Free BSA (ICN)] then diluted to a final concentration of 250,000 cells per mL. Compounds are serially diluted into DMSO then diluted into assay buffer with a 3× concentration of glucagon and 3% DMSO. The EC80 of glucagon is predetermined from a full glucagon dose response and represents the dose at which glucagons produces an 80% of the maximal glucagon response. A mixture of biotinylated cAMP (1 unit/well final) from the Alpha Screen Kit and 3×IBMX (1500 uM) is prepared in Assay Buffer.

The functional assay is performed in 96 well, low-volume, white, poylstyrene Costar Plates (3688). The biotinylated cAMP/IBMX mixture, 0.02 mLs, is placed into each well, followed by addition of 0.02 mLs of glucagon dose response, cAMP standard curve, or compound/glucagon mixtures. The reaction is started by addition of 0.02 mLs of cells (5000/well final). After 60 minutes at room temperature, the reaction is stopped by the addition of 0.03 mLs of Lysis Buffer [10 mM Hepes, pH 7.4, 1% NP40, and 0.01% fatty acid free BSA (ICN) containing 1 unit each/well of Acceptor and Donor beads from the Alpha Screen Kit]. Lysis Buffer addition is performed under a green light to prevent bleaching of the detection beads. The plates are wrapped in foil and left to equilibrate overnight at room temperature. The plates are read on a Packard Fusion™-α Instrument.

Alpha screen units are converted to pmoles cAMP generated per well based upon the cAMP standard curve. The pmoles cAMP produced in the presence of compound are converted to % of a maximal response with the EC80 dose of glucagon alone. With each experiment, the dose of glucagon needed to produce a 50% response of pmoles cAMP is determined. This EC50 dose is used to normalize results to a Kb using a modified Cheng-Prusoff equation (Cheng Y., Prusoff W. H., Biochem. Pharmacol. 22, 3099-3108, 1973), where Kb=(EC50 compound)/[1+(pM glucagon used/EC50 in pM for glucagon dose response)].

The compounds according to the invention preferably have a Ki value of no greater than 50 μM as determined by the Glucagon Receptor (hGlucR) Binding Assay disclosed herein. More preferably, the compounds according to the invention have a Ki value of less than 5 μM, preferably of less than 500 nM and even more preferred of less than 100 nM as determined by the Glucagon Receptor (hGlucR) Binding Assay disclosed herein. Generally, the compounds according to the invention show a higher affinity for the glucagon receptor compared to the GLP-1 receptor, and preferably have a higher binding affinity to the glucagon receptor than to the GLP-1 receptor.

The results are given below for the indicated compound.

TABLE 2

| Example | Ki (nM) |
| --- | --- |
| racemic | 951 |

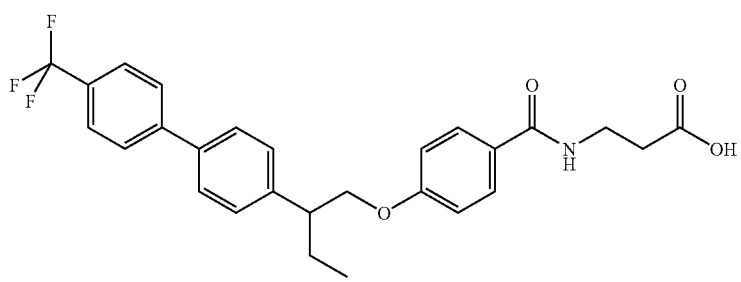

TABLE 2-continued

| Example | Ki (nM) |
| --- | --- |
| racemic | 801 |

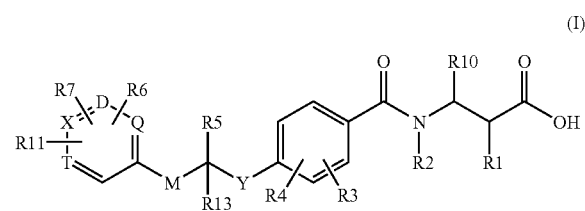

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

What is claimed:

1. A compound structurally represented by Formula I (I)

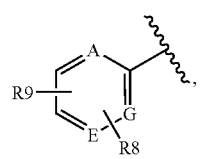

or a pharmaceutically acceptable salt thereof wherein:

Y is —O—;

M is a bond;

Q and X independently represent carbon and D and T represent nitrogen;

R1 is —H; R2 is —H; R3 and R4 are —H;

R5 is —H or —($C_1$-$C_7$) alkyl(optionally substituted with 1 to 3 halogens);

R6 and R7 are independently at each occurrence —H or -halogen, provided R6 or R7 are not attached to D or T;

R8 and R9 are independently at each occurrence selected from -hydrogen or —($C_1$-$C_7$)alkyl(optionally substituted with 1 to 3 halogens);

R10 is —H;

R11 is independently wherein A, G, and E independently represent carbon wherein the zig-zag marks show the point of attachment to the parent molecule, and provided R11 is not attached to D or T; and R13 is —H.

2. A compound or salt of claim 1 wherein R5 is hydrogen, methyl, ethyl, propyl, isopropyl, butyl, pentyl, hexyl, octyl, decyl, 3,3-dimethylbutyl, 2-methylpropyl, 4-methylpentyl, 2,2-dimethylpropyl, trifluoropropyl, trifluorbutyl; R6 and R7 are hydrogen; R8 and R9 are independently hydrogen, fluoro, methyl, ethyl, pentyl, isopropyl, tert-butyl, 2-methylpropyl, or trifluoromethyl; R10 is hydrogen; and R11 is phenyl (substituted independently once with R8 and once with R9).

3. A pharmaceutical composition which comprises a compound or salt of claim 1 and a pharmaceutically acceptable carrier.

4. A method for treatment of type 2 diabetes which comprises administering to a mammal in need of such treatment an effective amount of a compound or salt of claim 1.

5. A method for treatment of type 2 diabetes which comprises administering to a mammal in need of such treatment an effective amount of a pharmaceutical composition of claim 3.

6. A compound or salt of claim 1 selected from the group consisting of:

(R,S)-3-(4-{1-[2-(4-Trifluoromethyl-phenyl)-pyrimidin-5-yl]heptyloxy}-benzoylamino)-propionic acid;

(R,S)-3-(4-{4,4,4-Trifluoro-1 -[2-(4-trifluoromethyl-phenyl)-pyrimidin-5-yl] -butoxy}-benzoylamino)-propionic acid;

3-(4-{1[2-(4-Trifluoromethyl-pheny)-pyrimidin-5-yl]-heptyloxy}-benzoylamino)-propionic acid, isomer 1;

3-(4-{1[2-(4-Trifluoromethyl-phenyl)-pyrimidin-5-yl]-heptyloxy}-benzoylarnino)-propionic acid, isomer 2;

3-(4-{4,4,4-Trifluoro-1-[2-(4-trifluoromethyl-phenyl)-pyrimidin-5-yl]-butoxy}-benzoylamino)-propionic acid, isomer 1;

3-(4-{4,4,4-Trifluoro-1-[2-(4-trifluoromethyl-phenyl)-pyrimidin-5-yl]-butoxy}-benzoylamino)-propionic acid, isomer 2;

or a pharmaceutically acceptable salt thereof.

* * * * *